US010428334B2

(12) United States Patent
Fox et al.

(10) Patent No.: US 10,428,334 B2
(45) Date of Patent: Oct. 1, 2019

(54) METHOD OF CREATING INDUSTRIAL STREPTOMYCES WITH CAPABILITY TO GROW ON CELLULOSIC POLYSACCHARIDE SUBSTRATES

(71) Applicant: Wisconsin Alumni Research Foundation, Madison, WI (US)

(72) Inventors: Brian Grant Fox, Madison, WI (US); Robert Joseph Stankey, Madison, WI (US); Cameron Robert Currie, Madison, WI (US); Emily Beebe, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 15/478,871

(22) Filed: Apr. 4, 2017

(65) Prior Publication Data

US 2017/0283812 A1 Oct. 5, 2017

Related U.S. Application Data

(60) Provisional application No. 62/318,399, filed on Apr. 5, 2016.

(51) Int. Cl.

| | |
|---|---|
| ***C07H 21/04*** | (2006.01) |
| ***C12N 9/42*** | (2006.01) |
| ***C12N 9/24*** | (2006.01) |
| ***C12N 15/09*** | (2006.01) |
| ***C12N 15/74*** | (2006.01) |
| ***C12P 19/14*** | (2006.01) |
| ***C12P 19/02*** | (2006.01) |
| ***C12N 15/76*** | (2006.01) |
| ***C12N 15/52*** | (2006.01) |

(52) U.S. Cl.

CPC ........... *C12N 15/76* (2013.01); *C12N 9/2434* (2013.01); *C12N 9/2437* (2013.01); *C12N 15/52* (2013.01); *C12P 19/02* (2013.01); *C12P 19/14* (2013.01); *C12Y 302/01004* (2013.01); *C12Y 302/01091* (2013.01); *C12Y 302/01176* (2013.01); *C12P 2203/00* (2013.01)

(58) Field of Classification Search

CPC .... C12N 15/80; C12N 9/2437; C12N 9/2448; C12Y 302/01091; C12Y 302/01004

USPC .......... 435/209, 254.11, 254.3, 320.1, 252.2; 536/23.2

See application file for complete search history.

(56) References Cited

U.S. PATENT DOCUMENTS

2010/0184138 A1* 8/2010 Bower et al.

2016/0032340 A1* 2/2016 Fox ..................... C12N 9/2437 435/99

OTHER PUBLICATIONS

Tomotsune et al. Int J mat ENG Resour, 2014, 20, pp. 213-218.*

Elena et al. Frontiers of Microbiol, 2014, vol. 5, p. 1-8.*

Adams AS, et al. Cellulose-degrading bacteria associated with the invasive woodwasp *Sirex noctillo*. ISME J. 2011;5 (8):1323-31.

Bibb MJ, et al. (1986) Cloning and analysis of the promoter region of the erythromycin-resistance gene (ermE) of *Streptomyces erythraeus*. Gene 41:E357.

Bierman M , et al. Plasmid cloning vectors for the conjugal transfer of DNA from *Escherichia coli* to *Streptomyces* spp. Gene. 1992;116(1):43-9.

Book AJ, et al. 2016. Evolution of high cellulolytic activity in symbiotic Streptomyces through selection of expanded gene content and coordinated gene expression.

Book AJ, et al. (2014) Cellulolytic Streptomyces strains associated with herbivorous insects share a phylogenetically linked capacity to degrade lignocellulose. Appl Environ Microbiol 80: 4692-4701.

Cambray G, et al. (2013) Measurement and modeling of intrinsic transcription terminators. Nucleic Acids Res 41: 5139-5148.

Espah Borujeni A, et al. (2014) Translation rate is controlled by coupled trade-offs between site accessibility, selective RNA unfolding and sliding at upstream standby sites. Nucleic Acids Res 42: 2646-2659.

Forsberg Z, et al. Cleavage of cellulose by a CBM33 protein. Protein Sci. 2011;20(9):1479-83.

Gibson DG et al. (2009) Enzymatic assembly of DNA molecules up to several hundred kilobases. Nature methods 6:343-345.

Khadempour L, et al. (2016) The fungal cultivar of leaf-cutter ants produces specific enzymes in response to different plant substrates. Mol. Ecol. 25:5795-5805.

Langmead et al. (2012) Fast gapped-read alignment with Bowtie 2. Nature methods 9:357-359.

Miller GL (1959) Use of dinitrosalicylic acid reagent for determination of reducing sugar. Analytical Chemistry 31: 426-428

Richardson SM, et al. (2012) Design-A-Gene with GeneDesign. Methods in Molecular Biology 852:235-247.

Schmitt-John T, et al. (1992) Promoter constructions for efficient secretion expression in Streptomyces lividans. Applied Microbiology and Biotechnology 36:493-498.

Siegl T, et al. (2013) Design, construction and characterisation of a synthetic promoter library for fine-tuned gene expression in actinomycetes. Metab Eng 19: 98-106.

Takasuka TE, et al. (2013) Aerobic deconstruction of cellulosic biomass by an insect-associated Streptomyces. Sci Rep 3: 1030.

Takasuka TE, et al. (2014) Cell-free translation of biofuel enzymes. Methods Mol. Biol. 1118:71-95.

(Continued)

*Primary Examiner* — Robert B Mondesi
*Assistant Examiner* — Mohammad Y Meah
(74) *Attorney, Agent, or Firm* — Quarles & Brady LLP

(57) ABSTRACT

A heterologous gene cassette useful for creating *Streptomyces* species with enhanced capability of growing on a cellulosic polysaccharide substrate, wherein the cassette comprises at least two members of the following categories: a) a GH6 gene, b) an AA10 gene, c) a GH48 gene, d) a GH5 gene and e) either (i) a GH9 gene, (ii) a GH9 gene and a GH12 gene, or (iii) a GH12 gene is disclosed.

20 Claims, 27 Drawing Sheets
(12 of 27 Drawing Sheet(s) Filed in Color)
Specification includes a Sequence Listing.

(56) References Cited

OTHER PUBLICATIONS

Tian et al. (2015) A predictive biophysical model of translational coupling to coordinate and control protein expression in bacterial operons, Nucleic Acids Research 43:7137-7151.
Hanshew et al. (2014) Characterization of Actinobacteria Associated with Three Ant-Plant Mutualisms, Invertebrate Microbiology.
Noda et al. (2013) Creation of endoglucanase-secreting Streptomyces lividans for enzyme production using cellulose as the carbon source. Biotechnological Products and Process Engineering. Appl. Microbiotechnol, 97:5711-5720.

* cited by examiner

| | ID | ApraR | Promoter | GH6 | LPMO | GH48 | GH5 | GH9 | GH12 | Terminator |
|---|---|---|---|---|---|---|---|---|---|---|
| 1-2 | 1 | ■ | X | X | X | X | X | X | X | X |
| 1.5-1 | 6 | ■ | X | X | X | X | X | X | B6 | ■ |
| 1.5-4 | 8 | ■ | X | X | X | X | ActE | B6 | B6 | ■ |
| 1.5-8 | 9 | ■ | X | X | X | X | X | X | B6 | ■ |
| 2-3 | 15 | ■ | X | X | X | X | X | B6 | B6 | ■ |
| 2-5 | 16 | ■ | X | X | X | X | X | 95 | B6 | ■ |
| 2-9 | 17 | ■ | X | X | X | X | X | B6 | B6 | ■ |
| 2-10 | 18 | ■ | X | X | X | X | X | B6 | B6 | ■ |
| 2-12 | 19 | ■ | X | X | X | X | X | 95 | B6 | ■ |
| 2-13 | 20 | ■ | X | X | X | X | ActE | B6 | B6 | ■ |

FIG. 11

Example 2 protein sequences

>95GH5 (SEQ ID NO:1)

MLHPLRTFRRAARTVAVATAALLLPLAGAHPASADAARAAAAGSGYWHTSGRQILDAANQ
PVRIAGINWFGFETANYVPHGLWSRDYKSMIDQMRSLGYNTIRLPYSDDIFAGTEPASIN
YSAGMNTDLAGLNSLQVMDRIVDHAGSFGMKVILDRHRPDSAGQSALWYTSAVPESTWLA
HLKSLAARYAGNDAVVGIDLHNEPHDPACWGCGDTTKDWRLAAQRGGNAALSANPDLLIF
VEGVQTVDGVSGWWGGNLMGVGQYPVELSVPHKVVYSAHDYATSVAQQPWFTDSSFPDNM
PGVWDKYWGYIFKQNIAPVWVGEFGTTLQSTTDQKWLKALADYLRPTSQYGADSFSWTFW
SWNPNSGDTGGILKDDWTSVDTVKDGYLASIKAPDFGNGGGSGGDDDTQAPTAPTGLAVT
GTTGTSVSLSWKAASDDTGVTAYDVYRGSTKAGTATGTTFTDTGVTSGTSYTYTVRARDA
AGNTSAPSASVTATTTGSGGNTGCKAVYTVNGDWGSGFGVDITVTNTGTAPATSWKLTWT
YGGSQKITNMWNASYTQSGASVTVTSTDYNGGLAAGAHTGFGFQGTPAAGAVPTVSCTLS
*

>95GH6 (SEQ ID NO:3)

MSTRGTIKQGLRRRLAAASALAMGAALAVAIPTTADAAAARVDNPYVGAKAYVNPDWSAK
AAAEPGGAAIADTPAFVWMDRIAAIGGTPGAMSLREHLDTALDQGANLFQVVIYDLPGRD
CAALASNGELGPTELDRYKSEYIDPISEILADPAYANLRIVTIIEPDSLPNIVTNAGGTA
GSTDACATMKANGNYEKGVGYALHTLGAIPNVYNYVDAAHHGWLGWDSNMVPAGVEFKKA
ATSEGATVDDVAGFIVNTANYSALKEPNFKITDSVNGTTVRQSKWVDWNYYTDELSFAQA
LRTQLVGQGFNSNIGMLIDTARNGWGGSDRPTSAGPLTSVDDYVNGGRVDRRIHAGNWCN
QSGAGIGERPTSAPEAGIDAYVWAKPPGESDGSSQAEDNDEGKGFDRMCDPTYEGNGRNG
NSKTGALPNSPVAGHWFSAQFQELVRNAYPPIDGSGENPGGGGDDDTQAPTAPTGLTSSA
KTSSSVSLSWTASSDNKAVTGYDVYRGGTKVGSTTTTSYTDTGLSASTAYSYTVKAKDAA
GNVSAASSALSVTTSAGGGTGTGSLKVQYKNNDNSPTDNQIRFGLQLVNTGSSAVDLSTV
KLRYWFTPESGSSTFGTACDYAVLGCGKLSLAVQSGGSAAGASHYLEVSFGSGSLAAGAS
TGEMQLRLNKSDWSNFNEADDYSHGTGTSFADASKIGVYTAGALSWGTAP*

>95GH9 (SEQ ID NO:4)

MRSFPLPALRRRSRRPGRPLGAVALALAVGAGLLLPLSLPAGAAAAPAFDYGEALQKSVL
FYEAQQSGKLPDTNRVSWRGDSALDDGKDAGLDLTGGWYDAGDHVKFGLPMAYSATMLAW
GGTEQRAAYEASGQLPHLRNNLRFVDDYLLKAHPSPNVLYGQVGNGGDDHKWWGPAEVMP
MKRPAYKIDASCPGSDLAGQTAAALASSSMVFSDSDPAYAAKLITHAKQLYTFADTYRGK
YSDCITDAQSYYNSWSGYNDELVWGAIWLYKATGDTAYLAKAESYYDNLSTEPQTTTRSY
RWTLSWDDTSYGAYVLLAQLTGKQKYIDDANRWLDWWTVGVNGQRVPYSPGGQAVLDSWG
SLRYAANTAFVALSYSDWLTGDATRKARYHDFAVRQIDYALGDNPRGSSYVVGFGENPPT
KPHHRTAHGSWTDQMTNPVETRHTLYGALVGGPSAPDDTYTDDRGNYVNNEVATDYNAAF
TGALARLYAEYGGSPLTDFPQPEEPDGPEMSVQASVNAAGANFTEVKAYLINRSAWPARA

FIG. 13

Example 2 protein sequences

LTDASVRYYFTLEPGVAPGDISFTTNYNQCGEVTGPTHLTGDVYYATVDCSDTDIAPAGQ
SAYRKEVQFRISSAGAWDPSNDWSYPSTATTPGGTPVDAPHMVLLEGSAPQWGTAPDGTD
PGPGPDPTTTPEPSPTPDPTDTPDPEPGACDVTYRVSQAWGTGFTADVTVKNTGPTPLDG
WQLAFDFQGAESVSNAWNATATQSGTRVTLKNAGHNGSVPAGGSASFGFQANGAPGADPH
SFTLNGKECG*

>95GH12 (SEQ ID NO:5)

MTGRPLPALAGAAAALVLAAASMLTGASSASASPVTDCTPWGTTELLGGEYLYQQNEWNS
DSEQCVGVDPDTGAWSVTTSSFNLPTNGAPATYPSSYKGCHWGACTSDSGLPLRVDELGS
VHTDWSTTQVGSGAYNVSMDVWFNSAPVTDDQPDGTELMIWMNHRGGVQPIGSRTATVQL
DGRTWDVWTGPGASGWKVISYVLQGGATELTGFDVKSLIDDGVGRGQIDPAHYLIDAEAG
FEIWQGGQGLGMKEFSFEASAGTDGGDDGGDGDPGGGGTTGALKAQYKNNDSSATDNQIR
PGLQLVNTGSTAVDLSTVKLRYWFTPESGAAGFGTACDYAVVGCGNVTHTVKQAGTAAGA
SHYLEVGFTGGSLAPGASTGEIQLRFNKSDWSAFDEADDYSRAANTAFTDASKVGVYVNG
ALSSGTAP*

>95GH48 (SEQ ID NO:6)

MLAVGLAQGTAIARPASAQAGTGARAAAAGDDPYTQAFLTQYGKLKDAANGYFSPDGLPY
HSVETLMVEAPDHGHQTTSEAVSFWMWLEAAYGRVTGDWAPFNAAWAVAEKTIIPQHADQ
STSDSYNPSAPATYAPEHPLPSGYPSALDGTVPVGTDPLSAELASSYGTMDVYGMHWLMD
LDNVYGYGNKPGTGGESGPGAGASFINTYQRGAQESVWETVPQPTTDLFKYGGPNGYLDL
FVGDSSYAKQWKYTNAPDADARAVQAAYWAYRWASEQGKESQVAASVAKAAKMGDYLRYA
MFDKYFKRVGDCTDPNSCPAASGRDSQHYLLSWYYAWGGAAAGSGGGWAWRIGDGASHQG
YQNPLAAWALSNVPSLTPKSATARSDWSKSLTRQLEFLTWLQSSEGALAGGCTNSWEGSY
STPPAGTPTFYGMAYDWQPVYHDPASNNWFGFQAWGMERVAAYYYVTGNATAEAVLSKWV
AWASSETTIGSDGSFRFPSTLNWTGEPDTWNAASPGDNAGLHVSVVDYANDVGVGAAYVK
TLTYYAAKSGDEDAAALAKALLDAMALNTTDKGISVPETRLDYNRFDDEVYIPSGWSGTM
PNGDPVRPGSTFISIRSWYKDDPDWPKVQAYLDGGDAPVFTYHRFWAQAALALAFAIYAE
LLVEGGGGEPGGDTEPPTAPGGLTVTATTKDSVSLSWSASTDNTAVTGYDVYRNGVLAGN
ATGRTFTDSGLAANTEYTYAVAARDAGGNTSALSDAVLAKTKTGGSTGTGAVKVQYKSTD
SSATDNQIRMGLQVVNTGSAPVDLSTVKVRYWFTADGGPSTFGTYCDYAALGSSTITHTV
VAVSSPKTGADRYLEVGFTGGAGTLAAGASTGEIQLRLNKSDWSNFNEADDYSRATNTAY
ADSSKVGAYVAGALAWGVEP*

>95LPMO (SEQ ID NO:7)

MARRRTQLASLAAVLATLLGGIAFTLLGQGSAQAHGVTMSPGSRTYLCWLDAKTSTGSLD
PTNPACKAALAESGASSLYNWFAVLDSNAGGRGAGYVPDGTLCSAGDRSPYNFTGYNAAR

FIG. 13 (continued)

Example 2 protein sequences

GDWPRTHLTSGAKIEVDHSNWAAHPGEFRVYMSKPGYSPTTELGWDDLDLIQTVSNPPQV
GSPGTDGGHYYWDLTLPSGRSGDAVMFIQWVRSDSQENFFSCSDIVFDGGNGEVTGIRGS
GSTPDPDPTDPTPDPTDPTDPTDPHTGCMAVYNVTNSWSGGFQGSVEVMNHNTTALDGWA
VQWKPGTGTTVSSVWSGVLSTGSDGTLTVKNADYNRSIPPDGSVTFGFTATSTGNDFPVG
SIGCVSP*

>ActE236GH48 (SEQ ID NO:8)
MAALALPLGMTAAAGTEAQAAAVACSVDYTTSDWGSGFTTELTLTNRGSAAIDGWTLTYD
YAGNQQLTSGWSGTWSQSGKTVSVKNAAWNGAIAAGAAVTTGAQFTYSGANTAPTTFAVN
GTVCAGAHQPPIAVLTSPAAGAVFSAGDPVPLAATAAAADGATISKVEFYDDTTLLGTDT
TSPYSYEAGQLAAGSHSVYARAYDSLGASADSPPAGITVVTGPAVVVSPAQLGVQQGRSG
TFDVSLSTAPAADVTVTAARSAGNTGLSVTGGSTLTFTPANWSTPQKVTVTADGSGTGAA
TFTVTAPGHGKAEVTVTQLAAAKEYDARFLDLYGKITDPANGYFSPEGIPYHSVETLIVE
APDHGHETTSEAYSYLIWLQAMYGKITGDWTKFNGAWDTMETYMIPTHADQPTNSFYDAS
KPATYAPEHDTPNEYPAVLDGSASSGSDPIAAELKSAYGTDDIYGMHWIQDVDNVYGYGN
APGTCAAGPTQAGPSYINTFQRGSQESVWETVTHPTCDNFTYGGANGYLDLFTGDSSYAK
QWKFTNAPDADARAVQAAYWADVWAKEQGKAGEVADTVGKAAKMGDYLRYSMFDKYFKKI
GDCVGPTTCPAGSGKDSAHYLMSWYYAWGGATDTSAGWSWRIGSSHAHGGYQNPMAAYAL
SSVADLKPKSATGAQDWAKSLDRQLDFYQWLQSDEGAIAGGATNSWKGSYAQPPAGTPTF
YGMYYDEKPVYHDPPSNQWFGFQAWSMERVAEYYHESGDAQAKAVLDKWVDWALSETTVN
PDGTYLMPSTLQWSGAPDTWNASNPGANAQLHVTVADYTDDVGVAGAYARTLTYYAAKSG
DTEAEATAEALLDGMWQHHQDDAGVAVPETRADYNRFDDPVYVPGGWTGAMPNGDTVDED
STFLSIRSFYKDDPNWPQVQAYLDGGAAPVFTYHRFWAQADIALALGAYADLLE*

>ActE237GH6 (SEQ ID NO:9)
MSRTSRTTLRRSRTALMAAGALVAAAAGSAAAAAPFGATAAAAAGCTVDYKIQNQWNGGL
TASVSVTNNGDAISGWQLQWSFAGGEQVSQGWNATVSQSGSAVTAKDAGYNAALATGASA
SFGFNATGNGNSVVPATFKLNGVTCNGGTTGPTDPTDPTDPTDPTDPPAGNRVDNPYQGA
KVYVNPEWSANAAAEPGGDRIADQPTGVWLDRIAAIEGANGSMGLRDHLDEALTQKGSGE
LVVQVVIYNLPGRDCAALASNGELGPTEIGRYKTEYIDPIAEILGDPKYAGLRIVTTVEI
DSLPNLVTNAGGRPTATPACDVMKANGNYVKGVGYALNKLGDAPNVYNYIDAGHHGWIGW
DDNFGASAEIFHEAATAEGATVNDVHGFITNTANYSALKEENFSIDDAVNGTSVRQSKWV
DWNRYTDELSFAQAFRNELVSVGFNSGIGMLIDTSRNGWGGANRPSGPGANTSVDTYVDG
GRYDRRIHLGNWCNQAGAGLGERPQAAPEPGIDAYVWMKPPGESDGSSSEIPNDEGKGFD
RMCDPTYTGNARNNNNMSGALGGAPVSGKWFSAQFQELMKNAYPAL*

>ActE3159LPMO (SEQ ID NO:10)

FIG. 13 (continued)

Example 2 protein sequences

MARRSRLISLAAVLATLLGALGLTALWPGKAEAHGVAMTPGSRTYLCQLDALSGTGALNP
TNPACRDALSQSGANALYNWFAVLDSNAGGRGAGYVPDGSLCSAGDRSPYDFSAYNAARA
DWPRTHLTSGATLKVQYSNWAAHPGDFRVYLTKPGWAPTSELAWDDLQLVQTVSNPPQQG
GAGTNGGHYYWDLALPSGRSGDALMFIQWVRSDSQENFFSCSDIVFDGGNGEVTGIGGTG
TPTPTPTPTPTPTPTDPEHSGSCMAVYNVVSSWAGGFQASVEVMNHGTEPRNGWAVQWKP
GSGTQINSVWNGSLSTGSDGTVTVRDVDHNRVIAPDGSVTFGFTATSTGNDYPAGTIGCV
TS*

>ActE3717GH9 (SEQ ID NO:11)
MWCHPYLRLRTSGRKVSSVNALPPPARPAPVRPRSRYGRRVLGMSAAALLCAGALAVPGT
AMADDAEPGPGPEQITNGDFATGTSAPWWTPNASAAVSEGRLCVEVPAGTANAWDVIVG
QNDVPIVAGESYELSYTARSTVPLTVQTRVQEAVEPYTTVLATADPVGAEDTRVARTFTA
SVDQPAASVQLQIGGGERATTFCLDDVSLRGGAEPPVYVPDTGSPVRVNQVGYLPRGPKS
GTVVTDAEAPLTWTVKAEDGSTAATGTTVPRGEDPSSRRRVHTFDFGDLTTAGDGYTVEV
DGEVSEPFSIRGDLYDSLRSDALAYFYHNRSGIEIDADLVGEQYARPAGHIGVAPNKGDT
DVPCRPGVCDYRLDVSGGWYDAGDHGKYVVNGGISVAQLMATYERTLTAPDAESAELGDG
ALRVPERDNGVPDILDEARWEMDFLIKMQVPAGEQLAGMVHHKMHDAEWTGLPMKPHLDP
QQRELHPPSTAATLNLAATAAQCARLYAPFDADFADRCLRAAETAWDAAKRHPDVLADPN
DGIGGGAYNDDDVSDEFYWAAAELFTTTGKDIYRQAVLSSAWHGDAGAVFPAGGGISWGS
TAGLGVLTLATVPNALTSDQLAQVRTVVTEGADRYAAQSREQAYGLPYAPRGEDYVWGSN
SQVLNNMVVLATAHDLTGDAAYQDAVLRGADYLLGRNPLNQSYVTGYGERDSHNQHHRFW
AHQNDPSLPNPAPGSIAGGPNLTAIASGDPVAAEKLSGCAPAMCYVDDIGSWATNEITIN
WNAPLAFIASYLDDAGEGGQTAAARTCQVTYSSHPWNSGSTVTVRVENTGSDPVSPWALT
WLLPGEQRLSHTWSAEFDQHGRTVSARPLSWNRTLAPGAAVDFGFNTSAAGSSPEPGAFK
LNGRACSAG*

>ActeE482GH5 (SEQ ID NO:12)
MKRFLALLATCATVLGLTALTGPQAVAAAGCTADYTITSQWQGGFQAAVKVTNLGTPVTG
WKLTFTLPDAGQKVVQGWNAAWSQSGSAVTAAGADWNGTLATGASAEAGFVGSFTGANPP
PTAFALNGVACTGSTGEPPAGSDGGTPVDVNGQLHVCGVNLCNQYDRPVQLRGMSTHGIQ
WFDACYDAASLDALANDWKSDLLRIAMYVQEDGYETDPAGFTRRVNDLVDMAEARGMYAL
IDFHTLTPGDPNVNLDRAKTFFASVAARNAGKKNVIYEIANEPNGVTWTAVKSYAEQVIP
VIRAADPDAVVIVGTRGWSSLGVSDGSDESEVVNSPVNATNIMYAFHFYAASHKDAYRST
LSRAAARLPLFVTEFGTVSATGGGAMDRASTTAWLDLLDQLKISYANWTYSDAPESSAAF
RPGTCGGGDYSGSGVLTESGALLKNRISTPDSFPTG*

>B6GH6 (SEQ ID NO:13)

FIG. 13 (continued)

Example 2 protein sequences

MSRTSRTTLRRSRTALIAAGALVAAAAGSAAAAAPFAASAAAATGCTVDYKIENQWNGGL
TAAVNVTNNGAPVTSWQLQWTFNGGEQVSQGWNATISQSGSAVTAKDAGYNGTLATGASA
SFGFNATGNGNSTVPATFKLNGVTCNGDTTGPTDPTDPTDPTDPPAGNRVDNPYQGAKVY
VNPEWSANAAAEPGGSRVANQPTGVWLDRIAAIEGANGSMGLREHLDEALTQKGSGELVV
QLVIYDLPGRDCAALASNGELGPTEIGRYKTEYIDPIAAIVADPKYAGLRIVTTVEIDSL
PNLVTNAGGRETATPACDVMKANGNYVKGVGYALNKLGDAPNVYNYIDAGHHGWIGWDDN
FGASAQIFHEAATAEGATVNDVHGFITNTANYSALKEQNFSINDSVNGTSVRESKWVDWN
RYTDELSFAQAFRNELVSVGFNSGIGMLIDTSRNGWGGSARPSGPGATTSVDTYVDGGRY
DRRIHLGNWCNQAGAGLGERPTAAPEPGIDAYVWMKPPGESDGSSSEIPNDEGKGFDRMC
DPTYTGNPRNNNNPSGALGGAPVSGKWFSAQFQELMKNAYPAL*

>B6GH9 (SEQ ID NO:14)
MNALPPPARPAPVRSRSRYGRRALGISAAALLCAGALAVPGTALADDAAPGPEQITNGDF
SAGTAPWWWTPNASAAVSEGRLCVEVPAGTAEAWDVIVGQNDIPIVAGESYELSYTARST
VPLTVQTRVQEAVEPYGTVLATADPVGTEDTQVTRTFTASVDQPAASVQLQIGGGERATT
FCLDDVSLRGGAEPPVYVPDTGSPVRVNQVGYLPRGVKSGTVVTDAEAPLTWTVKAGDGS
TAATGTTVPRGEDPSSRQRVHTFDFGGLTTPGDGYTVEVDGEVSEPFSIRGDLYDGLRSD
ALAYFYHNRSGIEIDADLVGEEYARPAGHIGVAPNKGDTDVPCKPGVCDYRLDVSGGWYD
AGDHGKYVVNGGISVAQLMSTYERTLTADNAESAQLDDGALRVPERGNGVPDILDEARWE
MDFLIKMQVPAGEPLAGMVHHKMHDAEWTGLPMKPHLDPQQRELHAPSTAATLNLAATAA
QCARLYAPYDEDFADRCLRAAETAWDAAKRHPDVFADPNDGVGGGTYDDNDVSDEFYWAA
AELFTTTGKDTYRQEVLSSDLHGDADAVFPAGGGLSWGATAGLGALTLATVPNNLTTDQL
DGVRATVTTAADRYAAQSRAQAYGLPYAPRGTDYVWGSNSQVLNNMVVLAVAHDLTGEAA
YQDAVLRGADYLFGRNPLNQSYVTGYGERDSHNQHHRFWAHQYDSSLPNPAPGSVAGGPN
LTAAGSGDPVAAEKLSGCAPAMCYIDDIGSWSTNEITVNWNAPLAFIASYLDDAGDGGQT
TASRTCEVTYSSHPWSGGSTVSVRVENTGSAPVEPWSLTWLLPGEQKLSHTWSAEFEQHG
RTVSARPLAWNRTLAPGAAVDFGFNTSATGAAADPGTFKLNGRACASG*

>B6GH12 (SEQ ID NO:15)
MKSLIASLRSAGTAVTASLVALATCAALGALAAPAQAADSICGQYGTTVIQDRYVVQNNR
WGTTDAQCVDVTDDGFTVTRADGSVPTNGAPKSYPSVYNGCHYTNCSPGTELPKRLDSIS
SAPTAITYTYVDGAVYDAAYDIWLDPQPKKDGVNRTEIMIWFNRVGPIQPVGSQTGTATV
AGRGWEVWTGNNGGNDVISFVSPSAISSWSFDVMDFVDATVARGMAQNSWYLTSVQAGFE
PWQNGAGLAVSSFSSSVLTGGGSEGPGEPGTPADGPCAVSYTANAWTDGFTADVKVTNTG
TVPVSGWRLGFTLPQGQTVTQAWNATVTPSSGAVTATGAAFNAEIAAGASQSFGFQGTHS
GTFTKPDRFTLNGAVCTVG*

FIG. 13 (continued)

Example 2 protein sequences

>B6GH48 (SEQ ID NO:16)
MAALALPLGMTAAAGTPAQAAAVACSVDYKANDWGSGFTTELTLTNRGSGAIDGWTLTYD
YAGNQQLTSGWSGVWSQSGKTVTVKNADWNGTVAAGQAVTAGAQFTYSGTNTDPTAFAVN
GTVCAGAHQPPIAVLTSPAAGAVFTAGDPVPLAATAAAADGATISKVEFYDNTTLLGTDT
TSPYSYTAQGLSAGSHSVYARAYDSLGASAESPPAGITVAAGPAVVATPAQLGVQQGKSG
TFNVSLSTAPASNVTATVARTAGNTGLSVTGGASLTFTPANWSTPQKVTVSADGSGTGAA
TFTVSAPGHGKAEVTVTQLAGAKEYDARFLDLYGKVTDPANGYFSPEGIPYHSVETLIVE
APDHGHETTSEAYSYLIWLQAMYGKITGDWTRFNGAWDTMETYMIPTHADQPTNAYYDAS
KPATYAPEHDTPNEYPAVLDGSVSSGSDPIAAELKSAYGTDDIYGMHWIQDVDNVYGYGN
SPGTCAAGPTQTGPSYINTFQRGPQESVWETVTHPTCDNFTYGGANGYLDLFTGDSSYAK
QWKFTNAPDADARAVQAAYWADVWAKEQGKSADVAGTVGKAAKMGDYLRYSMFDKYFKKI
GDCVGPTTCPAGSGKDSSHYLMSWYYAWGGATDTSAGWAWRIGSSHAHGGYQNPMAAYAL
SSVADLKPKSATGQQDWAKSLDRQLDFYQWLQSDEGAIAGGATNSWKGGYAQPPAGTPTF
HGMYYDEKPVYHDPPSNQWFGFQAWSMERVAEYYHESGDAQAKAVLDKWVDWALSETTVN
PDGTYLMPSTLQWSGAPDTWNASNPGSNAGLHVTVADYTNDVGVAGAYARTLTYYAAKSG
DADAKATAEALLDGMWQHYQDDAGVAVPETRADYNRFDDPVYVPGGWTGAMPNGDTVDQD
STFVSIRSFYQDDPNWPKVQAYLDGGAAPVFTYHRFWAQADIALALGAYADLLE*

>B6LPMO (SEQ ID NO:17)
MAGRSRLISLAAVLATLLGALGLTALWQGKAEAHGVAMMPGSRTYLCQVDALSGTGALNP
TNPACRDALSKSGANALYNWFAVLDSNAGGRGAGYVPDGTLCSAGDRSPYDFSAYNAARA
DWPKTHLTSGAGIQLQYSNWAAHPGDFRVYVTKPSWSPTSALGWNDLQLVQTVSNPPQQG
SPGANGGHYYWDLTLPSGRSGDALMFIQWVRSDSQENFFSCSDIVFDGGKGEVTGIGGSG
NGTPTPTPTPTPTDPEHSGSCMAVYNVESSWNGGFQASVEVMNHGTEPRNGWAVQWKPGT
GTQINSVWNGTLSTGSDGTVTVRNVDHNRVIAPDGSVTFGFTANSTGNDFPAGTIGCVTS
*

FIG. 13 (continued)

Example 2 DNA sequences

>ActE GH6 (SEQ ID NO:2)

ATGAGTCGTACGTCCCGCACCACACTGCGTCGCAGTCGGACGGCGCTGATGGCAGCAGGTGCACTCGTCGCGGCAGCCGCAGGGAGCGCAGCAGCAGCCGCTCCGTT
CGGAGCAACGGCAGCGGCCGCAGCAGGATGCACGGTCGACTATAAGATCCAGAACCAGTGGAATGGCGGTCTGACAGCATCAGTCTCCGTGACAAACAACGGGGACG
CCATCTCAGGTTGGCAGCTGCAGTGGAGCTTCGCAGGCGGAGAGCAGGTCAGCCAGGGTTGGAATGCCACAGTATCCCAGAGCGGATCGGCAGTCACGGCCAAGGAC
GCAGGTTATAACGCAGCGCTCGCCACCGGAGCCTCGGCCAGCTTCGGTTTCAATGCAACGGGCAATGGAAACAGCGTCGTTCCGGCAACCTTCAAGTTGAATGGTGT
AACCTGCAACGGGGGTACGACAGGACCGACGGACCCGACAGACCCGACCGACCCCACCGACCCGACAGACCCCCCGGCAGGTAATCGAGTGGACAACCCTTACCAGG
GAGCAAAGGTTTATGTCAACCCGGAATGGTCCGCCAACGCCGCAGCCGAACCCGGCGGTGACCGCATAGCGGACCAGCCGACAGGTGTCTGGTTGGATCGTATAGCG
GCCATCGAGGGGGCCAATGGAAGTATGGGCCTTCGCGACCACCTGGACGAAGCGTTGACGCAAAAAGGAAGCGGAGAGCTGGTGGTCCAAGTGGTCATCTACAATCT
CCCAGGTCGTGACTGTGCCGCACTGGCCTCGAACGGAGAACTCGGGCCGACCGAGATCGGACGCTACAAAACAGAATATATCGATCCGATAGCGGAGATCCTGGGTG
ACCCGAAGTACGCAGGGCTCCGGATCGTGACGACGGTAGAAATCGATAGTCTGCCGAATTTGGTCACTAATGCCGGAGGACGTCCAACGGCAACACCGGCGTGCGAC
GTCATGAAAGCCAACGGTAATTATGTGAAGGGTGTCGGATATGCACTGAACAAGCTCGGGGATGCGCCGAATGTGTACAATTATATCGACGCAGGCCATCACGGATG
GATCGGATGGGATGACAACTTCGGCGCCTCTGCAGAGATCTTCCACGAAGCGGCCACCGCAGAGGGGGCAACGGTCAACGACGTCCATGGTTTCATCACCAACACAG
CGAACTACTCAGCGCTGAAGGAAGAGAACTTCTCGATCGATGATGCAGTAAACGGCACCAGCGTCCGCCAGTCTAAGTGGGTGGACTGGAATCGATACACAGACGAG
CTCAGCTTCGCCCAGGCATTCCGCAATGAACTCGTGAGTGTGGGTTTCAACTCCGGTATCGGAATGCTGATTGACACGTCGCGGAACGGTTGGGGCGGAGCAAATCG
TCCGTCGGGCCCGGGTGCCAATACATCCGTCGACACGTATGTAGACGGAGGCCGCTACGATCGACGGATCCATCTCGGTAACTGGTGTAATCAGGCAGGTGCGGGAC
TCGGTGAACGCCCGCAGGCTGCGCCAGAACCGGGCATCGACGCCTACGTGTGGATGAAGCCCCCGGGAGAGAGTGACGGATCCAGCTCCGAAATTCCGAACGATGAG
GGCAAGGGATTCGACCGTATGTGCGACCCGACATACACGGGCAACGCACGGAATAACAACAATATGAGTGGCGCGCTGGGAGGTGCCCCCGTCTCGGGAAAGTGGTT
CAGTGCCCAATTCCAAGAGCTGATGAAAAATGCGTATCCGGCATTGTGA

>ActE LPMO (SEQ ID NO:18)

ATGGCCCGCCGCAGCCGACTGATCTCACTTGCAGCGGTCTTGGCAACCTTGCTTGGCGCATTGGGTCTGACGGCCCTGTGGCCGGGCAAGGCCGAAGCGCATGGTGT
CGCAATGACACCCGGTAGCCGGACCTACCTGTGCCAGTTGGACGCCCTCAGTGGGACAGGTGCGCTTAACCCGACGAACCCCGCCTGTCGAGATGCACTGAGCCAGT
CGGGTGCCAACGCCCTCTATAATTGGTTCGCAGTACTGGACTCTAACGCCGGCGGAAGGGGAGCGGGCTATGTGCCAGACGGATCCCTGTGCAGTGCAGGGGACCGC
TCCCCCTACGATTTCTCAGCATACAATGCGGCACGTGCCGACTGGCCGCGGACCCACCTGACGAGCGGCGCCACACTCAAGGTCCAATATTCGAACTGGGCAGCACA
CCCCGGTGACTTCCGTGTGTATCTGACAAAACCCGGATGGGCGCCGACCTCAGAGCTGGCCTGGGATGACCTTCAGCTCGTGCAAACCGTCTCGAATCCGCCCCAAC
AAGGAGGAGCAGGCACCAACGGGGGGCACTACTATTGGGATCTGGCGCTGCCGAGCGGGAGAAGTGGAGACGCATTGATGTTCATCCAGTGGGTGCGTTCGGATAGC
CAGGAGAACTTCTTCTCGTGTAGTGATATAGTGTTCGACGGAGGTAATGGGGAGGTAACTGGAATCGGGGGAACGGGAACACCCACACCGACCCCCACGCCGACCCC
CACCCCTACGCCGACAGACCCTGAGCATAGCGGTAGTTGCATGGCAGTCTACAACGTGGTCAGTTCATGGGCCGGGGGATTCCAGGCAAGCGTGGAAGTCATGAACC
ACGGCACGGAGCCGCGCAACGGGTGGGCGGTTCAATGGAAGCCGGGGAGCGGTACCCAGATTAACAGTGTATGGAACGGATCGCTGTCCACCGGTAGCGACGGGACG
GTCACAGTGCGGGACGTCGACCACAACCGTGTAATCGCACCGGATGGTAGTGTGACGTTCGGTTTCACCGCCACATCAACCGGCAATGACTATCCCGCAGGGACGAT
CGGATGCGTGACCTCGTAG

>ActE GH48 (SEQ ID NO:19)

ATGGCAGCACTTGCACTCCCGCTGGGGATGACGGCCGCAGCGGGTACGGAGGCACAGGCCGCAGCGGTAGCCTGTAGCGTCGATTACACCACCAGCGACTGGGGCAG
TGGTTTCACTACAGAGCTCACATTGACCAACCGCGGAAGCGCAGCCATCGATGGCTGGACGCTTACATACGACTATGCGGGTAATCAGCAGCTGACGAGCGGATGGA
GTGGTACCTGGTCCCAGAGCGGCAAAACAGTCTCTGTCAAAAACGCAGCCTGGAATGGAGCAATTGCGGCGGGAGCAGCGGTAACGACAGGTGCCCAATTCACGTAC
AGTGGAGCCAATACCGCCCCGACAACCTTCGCAGTAAACGGAACCGTGTGCGCCGGAGCACATCAGCCGCCAATCGCAGTCCTGACCAGTCCGGCAGCCGGAGCAGT

FIG. 14

Example 2 DNA sequences

TTTCTCGGCGGGGGATCCAGTGCCCTTGGCGGCGACAGCGGCAGCCGCAGACGGTGCAACAATCTCGAAGGTCGAATTTTACGACGACACGACGCTGCTCGGTACCG
ACACAACATCGCCGTACAGTTATGAGGCCGGACAGCTCGCCGCAGGTTCTCACAGTGTATACGCAAGAGCCTACGACTCTCTGGGAGCCTCAGCAGATAGTCCTCCG
GCGGGCATAACGGTCGTCACAGGACCGGCGGTCGTAGTATCACCAGCGCAGCTGGGTGTGCAGCAAGGTAGGAGCGGAACGTTCGACGTATCCCTGAGCACGGCCCC
CGCAGCTGACGTGACCGTGACAGCCGCACGTTCGGCAGGTAATACGGGCTTGTCGGTGACCGGGGGCAGCACGCTTACCTTCACACCCGCCAACTGGTCGACGCCGC
AAAAAGTGACAGTCACAGCAGACGGATCGGGAACGGGTGCGGCAACATTCACGGTCACTGCACCGGGTCACGGCAAGGCAGAGGTGACCGTCACGCAGCTGGCGGCA
GCGAAGGAGTACGACGCCCGCTTCCTTGACCTCTACGGAAAAATCACGGACCCCGCGAACGGGTATTTCAGCCCGGAGGGTATTCCCTATCACTCGGTGGAAACCTT
GATCGTTGAAGCCCCGGACCACGGACATGAAACCACGTCGGAAGCATATTCCTACCTGATATGGCTGCAGGCAATGTATGGGAAAATCACAGGAGACTGGACGAAGT
TCAACGGAGCATGGGATACCATGGAAACGTACATGATCCCGACCCACGCAGACCAACCGACTAATAGCTTCTATGATGCGAGTAAGCCCGCAACATACGCCCCGGAG
CACGACACCCCCAATGAATATCCGGCAGTCCTGGACGGTTCGGCAAGTTCCGGAAGCGACCCCATAGCCGCAGAGCTCAAATCGGCATATGGTACGGATGACATCTA
CGGCATGCACTGGATCCAGGATGTGGACAATGTCTATGGTTACGGAAACGCCCCGGGCACCTGTGCAGCGGGGCCCACACAGGCAGGTCCAAGCTACATCAACACGT
TCCAACGGGGGTCCCAGGAGAGCGTATGGGAGACGGTCACCCACCCGACATGCGACAATTTCACGTATGGAGGCGCAAACGGTTACCTCGATCTGTTCACCGGCGAT
TCGTCGTACGCGAAGCAGTGGAAGTTCACAAATGCCCCGGACGCAGACGCCCGCGCCGTGCAAGCAGCATATTGGGCGGACGTGTGGGCCAAGGAACAAGGCAAGGC
AGGAGAGGTCGCAGACACAGTGGGAAAGGCAGCGAAGATGGGTGACTATCTGCGCTACAGCATGTTCGACAAGTATTTCAAGAAGATTGGCGATTGCGTAGGACCGA
CCACATGCCCCGCAGGTTCGGGCAAGGACTCCGCACACTATCTTATGAGCTGGTACTATGCATGGGGCGGCGCCACGGACACTTCGGCAGGCTGGTCCTGGCGCATC
GGTTCCAGCCATGCACATGGTGGCTATCAGAACCCGATGGCAGCGTACGCACTGTCCTCCGTAGCAGATCTCAAGCCGAAGAGCGCCACGGGTGCACAAGATTGGGC
AAAGAGTCTGGACCGGCAGTTGGACTTCTACCAGTGGCTGCAGTCCGACGAGGGCGCGATCGCGGGGGGTGCAACCAATAGCTGGAAGGGATCGTATGCACAACCGC
CCGCGGGCACGCCCACCTTCTATGGAATGTACTATGACGAAAAGCCGGTGTATCACGACCCGCCGAGCAACCAATGGTTCGGGTTCCAGGCATGGAGCATGGAGCGA
GTCGCAGAATACTACCATGAGTCGGGCGACGCACAGGCAAAGGCAGTCCTGGATAAGTGGGTGGACTGGGCCCTCTCAGAAACGACAGTCAACCCCGACGGAACGTA
TCTCATGCCCAGCACATTGCAGTGGTCGGGTGCGCCGGATACATGGAATGCAAGTAACCCGGGTGCAAACGCCCAACTCCACGTGACCGTGGCAGACTATACAGACG
ATGTCGGCGTGGCCGGGGCATACGCCCGCACGCTTACGTATTATGCCGCAAAAAGCGGCGACACGGAAGCAGAGGCGACCGCCGAGGCACTGCTGGATGGTATGTGG
CAACATCACCAGGACGACGCGGGTGTGGCAGTCCCCGAAACCCGCGCGGACTATAATCGATTTGACGATCCGGTGTATGTCCCGGGAGGTTGGACTGGCGCCATGCC
GAACGGAGACACAGTGGATGAGGACAGTACGTTCTTGTCAATCCGTTCGTTTTATAAAGACGATCCCAACTGGCCGCAGGTCCAGGCATATCTGGACGGTGGTGCCG
CACCGGTCTTCACTTACCATAGATTCTGGGCACAAGCAGATATTGCACTGGCCCTGGGTGCATACGCAGACCTCCTCGAATGA

>ActE GH5 (SEQ ID NO:20)

ATGAAGCGCTTCCTGGCACTCCTCGCCACCTGTGCAACGGTCCTCGGGCTGACCGCCCTTACAGGACCCCAAGCAGTAGCCGCGGCGGGATGCACCGCCGATTATAC
CATAACGTCGCAGTGGCAGGGCGGATTCCAAGCAGCAGTAAAAGTGACCAATCTGGGTACACCGGTCACCGGTTGGAAGCTCACATTCACATTGCCGGATGCAGGGC
AGAAAGTGGTGCAGGGCTGGAACGCAGCGTGGAGCCAATCGGGATCGGCGGTGACAGCCGCAGGGGCCGACTGGAATGGTACCCTTGCAACCGGTGCGAGTGCAGAG
GCGGGCTTCGTCGGTTCGTTCACAGGGGCCAACCCGCCACCGACAGCGTTCGCACTCAATGGAGTCGCCTGTACCGGTTCAACCGGTGAGCCACCGGCGGGAAGCGA
TGGCGGCACACCGGTCGATGTAAACGGTCAGCTCCATGTATGTGGAGTCAACCTGTGTAACCAGTACGACCGTCCAGTGCAATTGCGCGGTATGTCCACCCACGGTA
TCCAGTGGTTCGACGCATGCTATGACGCGGCAAGTCTGGACGCGCTGGCCAACGACTGGAAGTCCGACCTCCTGCGAATTGCAATGTATGTGCAGGAAGACGGATAC
GAGACAGACCCGGCCGGATTCACGCGTCGGGTCAATGACCTGGTAGACATGGCAGAAGCCCGCGGCATGTATGCCCTGATAGATTTCCACACGCTGACTCCCGGTGA
CCCGAATGTCAACCTTGATCGTGCCAAGACCTTCTTCGCGAGCGTGGCCGCAAGAAATGCCGGTAAAAAGAACGTCATCTATGAGATCGCAAACGAGCCGAACGGAG
TAACCTGGACAGCAGTCAAGTCGTATGCCGAGCAGGTGATACCCGTCATCCGCGCAGCAGACCCGGACGCAGTGGTAATCGTGGGAACCAGGGGTTGGAGCAGTCTC
GGTGTCAGCGACGGATCGGACGAGAGTGAAGTGGTCAACAGTCCGGTGAATGCCACCAACATTATGTACGCATTCCACTTTTATGCCGCGAGCCACAAAGACGCGTA
CAGAAGTACGCTCAGCAGGGCGGCAGCACGTCTTCCCCTGTTCGTCACAGAATTCGGTACCGTAAGTGCCACCGGTGGAGGAGCCATGGATCGGGCAAGCACCACCG
CGTGGCTGGACCTGCTCGATCAGCTCAAAATCTCGTATGCAAACTGGACATACAGTGACGCACCGGAGAGCTCCGCGGCCTTCCGCCCGGGGACCTGTGGTGGAGGT

FIG. 14 (continued)

Example 2 DNA sequences

GACTATTCCGGATCAGGTGTATTGACGGAGAGCGGCGCACTTCTCAAGAATCGTATAAGTACACCGGATTCATTCCCGACTGGTTAA

>ActE GH9 (SEQ ID NO:21)

ATGTGGTGCCACCCCTACCTGCGTCTCCGCACCAGCGGACGAAAGGTATCCAGTGTAAATGCTTTGCCTCCCCCAGCACGTCCTGCACCTGTGCGGCCACGGTCCCG
GTACGGTCGCCGGGTCCTCGGAATGTCGGCGGCCGCACTCCTGTGTGCCGGAGCACTCGCAGTACCGGGTACAGCGATGGCAGATGATGCCGAACCGGGGCCGGGTC
CAGAGCAGATCACGAACGGTGACTTCGCCACCGGAACGTCGGCACCGTGGTGGTGGACGCCCAACGCGTCCGCAGCCGTGTCGGAAGGTCGTCTGTGCGTAGAGGTG
CCGGCAGGCACGGCCAATGCATGGGATGTAATAGTCGGCCAGAACGACGTACCCATCGTCGCGGGTGAAAGTTACGAGCTCAGTTACACCGCCCGCTCGACAGTCCC
GCTCACGGTGCAAACCCGGGTCCAAGAGGCAGTGGAGCCGTACACCACGGTACTGGCCACCGCAGACCCCGTAGGTGCGGAGGATACACGCGTGGCACGCACGTTCA
CGGCGTCCGTCGACCAACCGGCGGCATCAGTACAGCTGCAGATAGGCGGAGGAGAACGGGCAACCACCTTCTGTTTGGACGACGTGTCTCTGCGCGGAGGCGCAGAG
CCCCCGGTGTATGTCCCGGATACAGGGAGTCCGGTGCGCGTGAACCAGGTAGGTTACCTTCCCAGGGGACCAAAGTCGGGCACAGTGGTCACCGACGCAGAAGCGCC
CCTGACGTGGACCGTGAAGGCAGAGGACGGTTCGACCGCGGCCACCGGTACGACCGTCCCGCGGGGAGAAGACCCGAGCTCGCGCCGACGTGTGCACACATTCGATT
TCGGTGACCTCACCACAGCCGGCGACGGATATACCGTAGAGGTCGACGGTGAGGTAAGCGAGCCCTTCTCAATTCGCGGTGATCTGTACGACTCGCTGCGTAGCGAC
GCCCTCGCGTATTTCTATCATAACCGATCGGGAATCGAGATCGACGCCGACCTGGTCGGGGAGCAATACGCACGTCCCGCAGGTCACATTGGCGTCGCACCGAATAA
GGGAGACACCGACGTCCCGTGTCGCCCTGGAGTGTGTGATTACCGCCTCGACGTCTCCGGGGGATGGTACGACGCGGGCGATCACGGGAAATATGTAGTGAACGGAG
GTATCAGCGTGGCCCAGCTTATGGCAACGTACGAACGTACCCTCACGGCGCCGGATGCGGAGTCGGCCGAACTCGGAGATGGTGCACTCCGCGTCCCGGAGCGCGAC
AATGGAGTGCCTGACATTTTGGACGAAGCACGGTGGGAGATGGATTTCCTGATCAAGATGCAGGTACCGGCTGGCGAACAACTCGCAGGCATGGTGCACCACAAAAT
GCACGACGCCGAATGGACCGGACTCCCAATGAAGCCCCATCTCGACCCCCAGCAGCGCGAGCTGCATCCTCCGTCCACGGCAGCAACACTCAATTTGGCAGCCACCG
CAGCACAGTGTGCACGTCTGTATGCCCCATTCGACGCAGACTTCGCCGATCGCTGTCTGAGGGCCGCAGAAACCGCCTGGGACGCAGCCAAAAGGCACCCGGACGTC
CTCGCAGATCCCAACGACGGAATCGGTGGCGGTGCATATAATGACGACGATGTATCAGACGAGTTCTACTGGGCAGCGGCCGAGTTGTTCACCACGACAGGGAAGGA
TATTTACCGTCAGGCGGTCTTGTCGAGCGCCTGGCATGGAGACGCAGGTGCCGTATTCCCGGCGGGCGGAGGTATCTCGTGGGGTAGCACGGCAGGCCTCGGTGTCC
TTACCCTGGCAACAGTCCCCAACGCTTTGACCTCGGATCAGCTCGCACAGGTGCGAACCGTAGTGACCGAGGGAGCCGACCGCTATGCAGCCCAGTCAAGGGAACAA
GCATACGGGCTCCCGTATGCGCCCCGTGGCGAGGACTATGTATGGGGCAGCAATTCGCAGGTCCTGAATAACATGGTGGTCTTGGCCACGGCACACGACCTGACAGG
TGACGCAGCGTACCAGGATGCAGTGCTCCGGGGCGCCGACTATCTCCTGGGCAGGAATCCTCTTAACCAAAGCTACGTAACCGGGTATGGTGAACGTGACAGCCACA
ATCAGCACCATCGTTTTTGGGCGCACCAAAACGATCCGTCGTTGCCCAACCCGGCCCCCGGCTCGATTGCCGGCGGACCCAACCTCACAGCAATCGCAAGTGGCGAT
CCCGTAGCAGCGGAGAAGCTGAGCGGTTGTGCACCCGCAATGTGCTACGTGGACGATATTGGAAGTTGGGCAACCAACGAAATCACGATCAACTGGAACGCGCCCTT
GGCCTTCATCGCCTCCTATCTGGACGACGCAGGTGAGGGAGGGCAGACAGCCGCAGCCCGCACGTGCCAAGTCACCTATTCGAGCCACCCGTGGAACAGTGGATCAA
CAGTAACGGTCCGTGTGGAGAATACCGGTTCGGATCCGGTGTCGCCCTGGGCCCTCACGTGGTTGCTGCCGGGGGAACAGCGCCTCAGTCACACTTGGTCAGCCGAG
TTCGACCAACATGGCCGTACGGTCAGCGCACGCCCCCTGTCGTGGAATCGTACACTGGCACCGGGAGCGGCAGTGGACTTCGGATTCAACACGTCAGCCGCAGGCTC
GAGTCCGGAGCCGGGGGCATTCAAGCTCAACGGAAGGGCATGTAGCGCAGGTTGA

>B6 GH6 (SEQ ID NO:22)

ATGAGTCGTACGAGCCGAACCACGCTGCGCCGGTCGCGCACAGCCCTGATCGCAGCAGGAGCCCTCGTAGCAGCAGCAGCGGGCAGTGCAGCCGCAGCCGCACCTTT
CGCAGCGTCCGCAGCAGCCGCAACCGGATGCACCGTAGACTATAAAATCGAGAACCAGTGGAACGGAGGACTGACAGCCGCAGTCAACGTCACCAACAACGGCGCGC
CGGTAACGTCATGGCAGCTGCAGTGGACCTTCAATGGGGGAGAACAAGTCTCCCAGGGATGGAACGCAACAATCAGCCAGAGCGGGTCAGCAGTAACTGCAAAAGAT
GCCGGTTACAATGGTACACTGGCAACAGGCGCCAGCGCATCGTTTGGATTCAACGCCACAGGTAATGGCAACAGTACCGTCCCGGCGACATTCAAACTGAACGGAGT
GACCTGTAACGGGGATACCACCGGACCCACAGACCCAACGGATCCTACGGACCCGACGGATCCCCCGGCAGGGAATCGCGTGGACAACCCGTATCAGGGCGCAAAGG
TATACGTGAATCCGGAGTGGAGCGCGAACGCCGCAGCGGAACCTGGGGGTTCCCGTGTCGCAAACCAACCCACCGGAGTGTGGCTCGACCGCATAGCAGCGATCGAG

FIG. 14 (continued)

Example 2 DNA sequences

GGTGCCAATGGATCGATGGGTTTGCGTGAGCATCTGGACGAAGCCTTGACCCAGAAGGGTAGCGGAGAGCTGGTCGTACAACTCGTGATTTATGACTTGCCGGGTCG
CGACTGTGCGGCCCTGGCATCCAACGGCGAACTCGGACCGACAGAAATCGGCAGATATAAGACCGAGTACATCGACCCAATCGCGGCCATAGTCGCGGACCCCAAAT
ATGCCGGACTGCGTATCGTAACAACGGTGGAAATAGACAGCCTGCCTAATCTGGTAACGAACGCAGGTGGCCGTGAAACCGCAACACCGGCATGTGATGTCATGAAG
GCAAACGGAAACTATGTCAAGGGCGTGGGATATGCACTGAACAAGCTCGGAGACGCGCCCAATGTCTACAACTATATTGACGCCGGTCACCACGGATGGATCGGGTG
GGACGATAATTTCGGCGCATCGGCGCAAATATTCCACGAAGCAGCAACTGCGGAGGGAGCAACCGTAAACGACGTGCACGGTTTCATCACGAACACGGCGAATTACA
GCGCACTGAAAGAACAGAACTTCAGCATCAACGATAGCGTCAATGGCACTTCCGTGAGGGAATCGAAGTGGGTCGACTGGAACCGCTACACGGACGAGCTCAGCTTC
GCACAAGCGTTCCGGAACGAACTTGTGAGCGTCGGCTTCAATTCGGGTATTGGGATGCTGATCGACACCAGTCGAAACGGCTGGGGAGGTAGCGCACGGCCCAGTGG
ACCAGGGGCTACCACCAGTGTCGACACGTATGTGGATGGTGGCCGCTATGACCGGCGCATCCACCTGGGAAACTGGTGCAATCAAGCCGGAGCAGGTTTGGGGGAAC
GACCAACCGCAGCCCCCGAGCCCGGTATCGACGCATATGTTTGGATGAAGCCGCCGGGAGAGTCGGACGGGTCCAGCTCCGAGATCCCTAATGATGAGGGTAAAGGC
TTCGACCGCATGTGTGACCCGACATACACGGGAAACCCCCGGAACAACAACAATCCGTCGGGCGCATTGGGGGGAGCGCCCGTGAGTGGTAAGTGGTTCTCGGCCCA
GTTCCAGGAGCTCATGAAGAACGCATATCCTGCACTCTGA

>B6 LPMO (SEQ ID NO:23)

ATGGCCGGCAGGTCCCGCCTGATTTCCCTCGCGGCGGTCCTGGCCACATTGCTGGGTGCACTGGGCCTCACCGCCCTCTGGCAGGGTAAGGCGGAAGCACATGGGGT
CGCAATGATGCCCGGAAGCCGGACATATCTGTGCCAAGTGGACGCCCTCTCTGGCACCGGAGCACTGAACCCGACAAACCCGGCATGTCGCGATGCGCTGAGCAAAT
CGGGTGCAAATGCCCTGTACAATTGGTTCGCAGTCCTGGACAGTAACGCCGGCGGAAGAGGTGCAGGCTACGTGCCGGATGGGACCCTGTGCTCCGCCGGCGACAGA
AGCCCGTACGACTTCAGCGCATATAATGCGGCACGTGCCGACTGGCCGAAGACGCACCTGACGAGTGGCGCAGGAATCCAGTTGCAGTATAGCAATTGGGCCGCACA
TCCGGGCGACTTCCGAGTCTACGTCACTAAGCCGTCGTGGTCACCCACAAGCGCGCTCGGATGGAACGACCTGCAGCTGGTACAGACCGTGTCGAATCCGCCGCAGC
AGGGCAGCCCTGGAGCCAACGGTGGTCACTATTATTGGGACCTCACCCTGCCGTCGGGTCGGTCGGGGGACGCACTGATGTTCATCCAGTGGGTCCGTAGCGACAGT
CAGGAGAACTTCTTCTCCTGTTCGGACATAGTATTCGACGGAGGCAAGGGCGAAGTGACCGGTATCGGGGGGTCCGGTAATGGAACACCGACACCCACACCCACCCC
CACGCCCACAGATCCCGAGCACAGCGGGTCGTGTATGGCCGTATATAACGTGGAGTCCTCGTGGAATGGAGGCTTCCAGGCCAGCGTAGAGGTAATGAATCACGGTA
CCGAGCCGCGAAACGGATGGGCGGTCCAGTGGAAGCCGGGAACGGGTACGCAGATCAACAGTGTATGGAACGGTACCCTGTCCACAGGGTCGGACGGTACCGTCACA
GTCAGGAACGTGGACCATAACCGCGTAATAGCACCGGATGGAAGCGTCACTTTCGGCTTCACCGCCAATTCGACAGGAAACGACTTCCCCGCGGGCACGATCGGATG
TGTAACGAGTTGA

>B6 GH48 (SEQ ID NO:24)

ATGGCAGCACTGGCCTTGCCGCTGGGTATGACCGCAGCGGCAGGCACCCCGGCACAGGCAGCAGCGGTAGCATGCTCAGTAGACTACAAGGCCAACGATTGGGGTTC
GGGCTTCACCACCGAACTGACACTCACAAATCGCGGTAGTGGTGCGATCGACGGATGGACACTCACGTACGATTATGCCGGTAACCAGCAGTTGACATCAGGATGGT
CGGGTGTGTGGAGTCAGAGTGGTAAGACGGTAACAGTGAAGAACGCAGACTGGAACGGAACCGTCGCGGCCGGCCAGGCAGTCACAGCCGGTGCACAGTTCACGTAT
AGTGGAACCAATACAGACCCGACAGCGTTCGCAGTGAACGGGACCGTATGCGCGGGAGCACACCAGCCCCCGATAGCCGTCCTCACCAGCCCTGCAGCAGGAGCGGT
CTTCACAGCAGGCGATCCGGTACCGCTGGCCGCAACCGCAGCAGCAGCGGACGGTGCGACCATTTCCAAGGTGGAGTTCTACGACAACACTACACTGCTCGGCACAG
ACACTACCTCACCATACTCATATACAGCGCAAGGACTGTCAGCCGGGAGTCATTCCGTGTATGCACGCGCATACGACTCATTGGGTGCGAGCGCAGAAAGTCCGCCA
GCCGGAATCACCGTCGCAGCGGGTCCGGCAGTAGTCGCAACACCCGCCCAGCTCGGAGTACAGCAGGGAAAGTCGGGCACCTTCAACGTGTCCCTTTCAACTGCACC
GGCCTCAAATGTCACAGCAACCGTCGCACGGACGGCAGGAAATACAGGATTGAGCGTCACCGGAGGCGCGTCACTGACCTTCACGCCCGCCAACTGGTCGACCCCTC
AAAAAGTAACCGTCTCCGCAGATGGTTCGGGAACAGGAGCAGCAACGTTCACAGTGAGTGCGCCTGGTCACGGAAAGGCAGAGGTAACGGTAACGCAGCTCGCGGGT
GCAAAGGAGTATGATGCACGATTCCTGGACTTGTACGGCAAAGTGACCGATCCGGCCAACGGGTACTTCTCTCCGGAGGGAATACCATACCACTCAGTGGAGACGCT
GATTGTCGAAGCGCCGGACCACGGTCATGAGACGACCAGTGAAGCCTATAGCTACTTGATATGGCTGCAAGCAATGTACGGCAAGATCACGGGTGACTGGACCCGCT

FIG. 14 (continued)

Example 2 DNA sequences

TCAACGGCGCGTGGGACACAATGGAAACCTATATGATCCCCACACACGCAGACCAGCCGACCAATGCATATTACGACGCCAGTAAGCCTGCAACATACGCACCCGAG
CACGACACCCCAAACGAATACCCGGCGGTACTTGACGGAAGCGTATCATCGGGCTCAGACCCCATCGCCGCCGAGCTGAAGTCGGCATATGGAACCGATGACATCTA
TGGAATGCACTGGATCCAGGATGTCGACAACGTATACGGCTACGGGAACAGTCCGGGAACGTGTGCTGCAGGGCCAACCCAGACCGGACCGAGCTATATCAACACCT
TCCAGAGGGGTCCCCAGGAGTCGGTGTGGGAGACGGTCACGCACCCAACATGCGACAATTTCACCTACGGGGGAGCAAATGGATATCTCGATCTGTTCACAGGTGAC
TCAAGCTATGCGAAGCAATGGAAGTTCACGAACGCCCCCGACGCGGACGCAAGAGCAGTACAAGCAGCATACTGGGCAGACGTATGGGCCAAAGAACAAGGTAAGAG
TGCAGACGTGGCGGGCACAGTGGGTAAGGCGGCAAAGATGGGAGACTATCTGCGGTACTCAATGTTCGACAAGTATTTCAAGAAGATCGGTGACTGCGTCGGCCCGA
CCACCTGCCCGGCAGGCTCTGGTAAAGATAGTTCTCACTACCTCATGAGTTGGTACTATGCCTGGGGCGGAGCAACCGACACCTCGGCAGGGTGGGCATGGCGTATA
GGAAGTTCACACGCACACGGCGGTTACCAAAACCCTATGGCAGCGTATGCGTTGTCGTCGGTGGCAGACCTGAAGCCAAAGAGTGCAACGGGCCAGCAGGATTGGGC
AAAGAGCCTGGACCGCCAGTTGGACTTCTACCAATGGTTGCAGTCGGACGAAGGGGCGATCGCAGGAGGCGCCACCAACTCGTGGAAGGGTGGGTATGCCCAGCCGC
CGGCGGGTACACCCACGTTCCACGGAATGTACTACGACGAGAAGCCCGTATACCACGACCCGCCCTCCAATCAGTGGTTCGGATTCCAAGCCTGGTCAATGGAACGG
GTCGCAGAGTATTATCATGAGTCAGGTGATGCACAGGCGAAGGCCGTGCTCGACAAGTGGGTCGATTGGGCACTGTCGGAAACTACAGTCAATCCCGACGGAACCTA
CCTGATGCCATCAACACTGCAGTGGAGCGGCGCCCCTGACACCTGGAACGCATCAAACCCGGGATCGAATGCGGGTCTGCACGTGACAGTAGCAGACTATACGAACG
ACGTGGGTGTGGCCGGTGCATACGCGAGGACGCTGACATATTACGCCGCAAAGAGCGGAGACGCCGATGCCAAGGCAACCGCAGAGGCACTGCTCGACGGCATGTGG
CAGCACTACCAAGATGACGCGGGAGTGGCCGTCCCCGAGACGCGCGCAGATTATAACCGGTTCGACGATCCAGTGTACGTCCCCGGTGGCTGGACCGGTGCCATGCC
GAATGGGGATACCGTGGACCAGGACTCGACATTCGTATCCATAAGGTCCTTCTATCAGGATGACCCCAACTGGCCGAAGGTCCAGGCCTACCTTGACGGTGGAGCGG
CGCCGGTCTTCACGTACCACCGTTTTTGGGCCCAGGCAGATATCGCTTTGGCCTTGGGTGCCTATGCAGACCTGCTCGAATGA

>B6 GH12 (SEQ ID NO:25)

ATGAAGAGCCTCATCGCCTCCCTCAGGTCAGCAGGCACGGCAGTCACAGCAAGCCTGGTGGCGCTCGCCACCTGCGCAGCCTTGGGAGCACTGGCAGCACCGGCACA
GGCAGCAGATTCGATCTGTGGCCAGTATGGAACGACGGTAATCCAAGACCGCTATGTCGTCCAAAACAACCGATGGGGAACCACGGACGCGCAGTGTGTGGACGTGA
CCGACGATGGGTTCACCGTAACGCGCGCAGACGGCTCGGTCCCCACCAATGGAGCACCGAAGTCGTATCCGAGCGTCTATAACGGTTGTCATTACACAAATTGTTCG
CCGGGAACCGAGCTCCCGAAGCGGCTGGATAGTATCAGCTCCGCCCCCACAGCGATCACATATACGTACGTCGACGGTGCCGTATACGACGCAGCATATGACATCTG
GCTCGATCCTCAGCCGAAAAAGGACGGCGTGAACAGGACAGAGATCATGATCTGGTTCAATCGGGTGGGGCCCATACAGCCGGTCGGTAGCCAGACGGGTACCGCCA
CGGTGGCAGGTAGAGGGTGGGAAGTCTGGACCGGTAACAACGGAGGTAATGACGTCATTTCCTTCGTATCCCCGTCGGCAATCTCCAGCTGGAGTTTCGACGTCATG
GACTTCGTAGACGCAACGGTGGCGCGCGGAATGGCACAGAACTCATGGTATCTGACCTCGGTGCAGGCGGGCTTCGAACCGTGGCAGAACGGAGCCGGCCTCGCAGT
ATCGTCCTTCTCAAGTTCGGTGTTGACCGGTGGCGGTTCAGAGGGACCCGGCGAGCCGGGAACACCGGCCGATGGTCCGTGCGCAGTCAGCTATACCGCCAACGCAT
GGACAGACGGATTCACGGCAGACGTGAAGGTCACCAATACAGGCACAGTGCCAGTCTCGGGATGGCGGTTGGGTTTCACACTGCCCCAGGGGCAGACGGTCACCCAG
GCATGGAACGCCACGGTAACCCCGTCGAGTGGAGCAGTGACGGCCACCGGTGCAGCGTTCAACGCAGAGATAGCAGCAGGGGCAAGTCAGAGTTTCGGATTTCAAGG
TACCCACTCGGGAACCTTCACAAAGCCCGACCGTTTCACCCTCAACGGTGCGGTCTGTACAGTCGGCTGA

>B6 GH9 (SEQ ID NO:26)

ATGAACGCATTGCCTCCACCGGCGCGGCCTGCCCCAGTACGTTCCCGCTCGCGTTATGGACGACGTGCACTGGGAATCAGTGCAGCGGCGTTGCTCTGTGCAGGCGC
GCTCGCGGTCCCCGGCACAGCACTGGCGGATGATGCAGCCCCTGGTCCCGAACAGATCACCAACGGAGACTTCAGCGCCGGTACAGCGCCATGGTGGTGGACGCCGA
ACGCCTCCGCGGCAGTGAGCGAAGGCCGATTGTGTGTAGAGGTCCCCGCCGGAACCGCAGAAGCCTGGGACGTAATCGTGGGTCAAAACGATATCCCTATAGTCGCA
GGCGAGTCCTACGAGCTGAGTTATACAGCGCGCAGTACGGTACCGCTCACCGTGCAGACGCGCGTCCAGGAAGCAGTAGAGCCATACGGAACTGTGCTCGCCACCGC
AGATCCGGTCGGAACGGAGGATACCCAGGTGACACGTACCTTCACAGCATCCGTCGATCAACCGGCGGCCAGCGTCCAGCTCCAAATTGGGGGGGGAGAACGCGCGA

FIG. 14 (continued)

Example 2 DNA sequences

CGACCTTCTGCCTTGACGACGTCAGCCTCCGTGGCGGAGCAGAGCCTCCCGTATATGTGCCGGACACGGGATCCCCAGTCCGAGTCAACCAAGTGGGATATCTGCCG
CGCGGTGTCAAGAGCGGCACAGTCGTAACAGACGCAGAGGCACCGCTCACCTGGACAGTGAAGGCCGGGGATGGAAGCACCGCAGCAACTGGAACCACAGTGCCGCG
GGGTGAGGACCCCAGTTCCCGACAGCGGGTCCACACATTCGATTTCGGTGGACTGACCACGCCGGGCGATGGTTACACAGTAGAGGTGGACGGAGAGGTATCGGAGC
CCTTCTCGATCCGAGGTGACCTCTATGATGGGTTGCGCTCCGATGCCCTGGCCTACTTCTATCACAACCGGAGCGGTATCGAAATAGATGCAGACCTGGTGGGCGAG
GAATATGCCCGTCCCGCAGGGCACATTGGCGTCGCGCCGAACAAGGGAGACACGGACGTCCCGTGTAAGCCAGGAGTCTGTGACTATCGGCTCGATGTCTCAGGCGG
TTGGTACGACGCCGGCGACCACGGTAAGTACGTAGTCAACGGGGGAATCAGCGTGGCACAGCTTATGTCCACATATGAGCGCACTCTCACCGCGGACAACGCAGAAT
CGGCACAGCTGGACGATGGCGCCCTGAGGGTCCCGGAACGTGGAAATGGAGTGCCGGACATCCTGGATGAGGCACGATGGGAAATGGATTTCCTGATAAAGATGCAG
GTCCCTGCCGGGGAGCCGTTGGCAGGAATGGTGCATCACAAAATGCACGACGCCGAGTGGACCGGACTGCCGATGAAGCCGCACTTGGACCCGCAACAGCGTGAACT
TCATGCACCCTCCACCGCAGCCACCCTCAACCTGGCGGCGACGGCAGCACAGTGCGCCCGACTCTATGCGCCCTATGACGAGGACTTCGCCGACCGTTGTCTCCGAG
CAGCAGAAACCGCATGGGACGCAGCGAAAAGGCACCCGGATGTCTTCGCCGACCCCAATGACGGTGTCGGTGGTGGTACATACGATGATAATGACGTATCCGACGAG
TTCTATTGGGCCGCGGCCGAACTCTTCACCACCACAGGCAAGGACACCTATCGTCAAGAGGTGTTGTCGAGTGATCTTCACGGTGATGCAGATGCCGTCTTCCCCGC
AGGAGGCGGCCTCAGCTGGGGTGCCACAGCAGGGCTCGGGGCGCTCACACTGGCCACGGTACCGAACAACCTGACCACGGACCAGCTCGATGGTGTGCGGGCAACCG
TCACCACCGCAGCAGATCGGTATGCGGCGCAATCCCGCGCCCAGGCATATGGCCTCCCGTACGCACCGCGCGGAACGGATTACGTATGGGGTAGCAACTCCCAGGTA
CTCAATAACATGGTGGTCCTCGCCGTAGCACACGACCTGACCGGAGAAGCGGCATATCAGGACGCGGTACTCCGGGGTGCAGACTACTTGTTCGGGCGCAATCCGCT
GAATCAGTCGTATGTCACGGGATACGGCGAGCGAGACTCTCACAACCAGCACCACAGGTTCTGGGCACATCAATATGATAGCAGTTTGCCTAATCCCGCACCAGGTT
CCGTAGCAGGTGGCCCGAACCTCACGGCAGCAGGAAGTGGTGACCCCGTCGCGGCCGAAAAGCTGTCGGGCTGCGCCCCGGCAATGTGCTACATCGACGACATCGGG
AGTTGGAGCACCAACGAGATTACAGTAAATTGGAACGCGCCGCTCGCATTCATTGCCTCGTACCTTGACGACGCCGGAGATGGTGGCCAGACCACAGCGTCACGTAC
ATGCGAAGTCACGTATAGCTCGCACCCGTGGAGCGGGGGAAGTACCGTCTCGGTGCGAGTAGAGAATACAGGTTCGGCCCCAGTGGAACCCTGGTCACTGACGTGGT
TGCTGCCGGGCGAGCAGAAGCTCTCCCACACCTGGTCAGCCGAATTCGAGCAACACGGGCGCACCGTGTCAGCAAGGCCGCTGGCGTGGAACCGGACCCTTGCACCG
GGAGCCGCAGTAGACTTCGGCTTCAATACGAGCGCGACAGGAGCAGCGGCCGATCCAGGCACGTTCAAGTTGAACGGTCGCGCCTGTGCATCGGGCTGA

>95 GH6 (SEQ ID NO:27)

ATGTCAACCCGTGGAACCATAAAACAGGGTCTGCGCCGTAGACTCGCAGCAGCAAGTGCACTGGCAATGGGAGCGGCACTCGCAGTAGCAATCCCGACAACCGCAGA
CGCCGCAGCCGCCCGAGTCGATAATCCATATGTCGGTGCAAAGGCATACGTGAACCCAGACTGGAGTGCAAAAGCAGCGGCCGAACCGGGCGGAGCAGCGATTGCCG
ATACACCGGCGTTCGTGTGGATGGACCGCATCGCAGCAATCGGTGGTACACCGGGTGCCATGTCGCTCAGGGAACACCTGGACACGGCACTGGATCAGGGTGCAAAT
CTCTTCCAAGTCGTCATCTACGACCTCCCGGGTCGTGACTGCGCAGCCCTTGCAAGTAATGGGGAGCTGGGACCGACGGAGCTCGATAGGTATAAGTCCGAATACAT
CGACCCGATCAGTGAGATCCTCGCGGACCCGGCATACGCGAATCTGCGGATAGTCACAATCATCGAGCCCGACTCGCTGCCGAATATTGTGACGAATGCGGGTGGCA
CCGCAGGATCGACAGACGCGTGTGCAACAATGAAGGCCAACGGTAATTATGAGAAAGGCGTCGGTTATGCACTCCACACCCTCGGTGCCATCCCGAATGTATATAAC
TACGTGGACGCAGCCCACCACGGCTGGTTGGGGTGGGATAGCAACATGGTGCCGGCCGGGGTGGAGTTCAAGAAGGCAGCAACAAGTGAGGGAGCAACCGTGGACGA
TGTCGCAGGATTCATAGTAAATACGGCGAACTACTCCGCACTTAAGGAGCCCAATTTCAAAATAACCGACTCAGTGAACGGCACTACGGTGCGTCAGAGTAAGTGGG
TCGATTGGAACTACTATACTGACGAGCTCAGTTTCGCGCAGGCCCTGCGCACCCAGCTGGTAGGCCAGGGATTCAACTCTAACATCGGTATGCTCATTGACACGGCA
CGCAATGGATGGGGAGGCTCGGATCGTCCGACATCAGCAGGGCCGCTGACGTCGGTCGACGACTACGTCAACGGTGGCCGGGTCGATCGCCGGATCCATGCGGGAAA
CTGGTGCAATCAGTCTGGCGCAGGAATCGGCGAGAGGCCGACCTCAGCGCCCGAAGCGGGAATCGACGCGTATGTATGGGCAAAGCCCCCCGGCGAGTCGGACGGGA
GTAGTCAGGCAGAAGATAACGACGAGGGAAAAGGTTTCGATCGAATGTGTGACCCGACATATGAAGGCAACGGAAGGAACGGAAACAGCAAGACGGGCGCGTTGCCG
AATTCCCCAGTAGCAGGGCACTGGTTCAGTGCACAGTTCCAAGAGCTTGTCCGTAATGCATATCCCCCGATCGACGGTAGCGGAGAGAACCCGGGTGGCGGCGGAGA
CGACGATACCCAGGCGCCGACGGCACCGACAGGGCTCACATCCTCGGCGAAGACCAGTTCAAGCGTCAGTCTCTCATGGACCGCCTCCTCGGACAATAAAGCAGTGA
CCGGTTACGATGTCTACCGGGGAGGAACGAAGGTAGGCAGCACGACCACGACATCGTACACGGACACGGGACTGAGCGCCTCGACGGCATATTCATACACCGTGAAG

FIG. 14 (continued)

Example 2 DNA sequences

GCGAAAGATGCCGCCGGGAACGTGTCGGCAGCATCGTCAGCACTGAGCGTCACAACGTCAGCCGGGGGAGGCACAGGAACGGGAAGCCTGAAGGTCCAATATAAAAA
TAACGACAACAGTCCGACAGACAACCAGATCAGGTTCGGTCTGCAACTCGTGAATACGGGATCCTCGGCCGTGGACCTGAGTACCGTCAAGCTCCGCTACTGGTTCA
CCCCAGAATCCGGCAGCTCCACGTTCGGGACAGCCTGCGATTATGCAGTACTGGGATGTGGTAAGCTGTCCCTTGCCGTACAATCAGGCGGAAGTGCGGCAGGAGCA
AGTCACTACCTCGAGGTCAGCTTCGGGTCGGGGAGCCTTGCGGCAGGTGCATCCACGGGGGAAATGCAGCTGCGACTGAACAAGAGCGATTGGTCGAACTTCAATGA
GGCGGACGACTATAGTCATGGGACCGGAACCTCGTTCGCCGACGCATCCAAAATAGGAGTGTATACCGCCGGCGCGTTGTCCTGGGGTACAGCCCCTTGA

>95 LPMO (SEQ ID NO:28)

ATGGCGCGCAGGCGCACACAGCTGGCAAGCCTTGCGGCCGTCCTGGCCACCCTCCTCGGTGGCATCGCCTTCACTCTGCTGGGACAGGGTTCGGCACAAGCCCACGG
CGTGACCATGTCCCCGGGATCCCGTACATACCTCTGCTGGTTGGACGCAAAGACATCGACCGGTTCACTGGATCCGACCAATCCGGCATGTAAGGCAGCACTTGCCG
AGTCCGGCGCGTCCTCGCTGTATAACTGGTTCGCCGTGCTCGACAGTAACGCAGGTGGACGAGGCGCAGGATACGTACCCGACGGCACCCTTTGTAGCGCTGGAGAC
AGGTCGCCGTACAATTTCACAGGCTATAACGCAGCCCGGGGGGATTGGCCCAGGACTCATCTGACCAGCGGCGCGAAAATCGAGGTAGACCACTCAAATTGGGCAGC
GCACCCGGGAGAGTTCCGTGTGTATATGAGCAAGCCGGGATACTCGCCGACCACGGAACTCGGTTGGGATGACCTCGACCTCATCCAGACCGTCTCTAATCCGCCCC
AAGTGGGGTCCCCGGGAACGGACGGTGGCCATTATTATTGGGATCTGACTTTGCCCTCGGGCAGGTCAGGAGATGCCGTTATGTTCATCCAATGGGTAAGGAGCGAC
AGTCAGGAGAACTTCTTCAGCTGCAGTGACATCGTCTTCGATGGCGGCAATGGTGAAGTAACCGGAATCCGCGGAAGTGGCTCGACCCCAGACCCGGACCCAACCGA
CCCGACCCCGGACCCGACAGACCCTACCGATCCGACAGACCCCCACACAGGATGCATGGCAGTGTACAATGTGACGAATAGCTGGTCAGGTGGATTCCAGGGTAGCG
TTGAAGTAATGAACCATAATACCACGGCGCTCGACGGTTGGGCGGTGCAGTGGAAACCGGGTACCGGTACGACAGTCTCCAGCGTATGGTCGGGCGTATTGTCGACG
GGAAGTGATGGTACCCTCACGGTGAAGAACGCAGACTATAATCGCAGCATCCCACCGGACGGCTCGGTCACCTTCGGTTTCACGGCGACCTCGACGGGGAACGATTT
CCCGGTGGGGTCCATAGGTTGTGTCTCCCCGTGA

>95 GH48 (SEQ ID NO:29)

ATGCTGGCAGTCGGCCTCGCACAGGGTACCGCAATCGCGAGGCCAGCAAGTGCCCAGGCAGGCACGGGTGCACGTGCGGCCGCAGCGGGAGACGATCCCTACACCCA
GGCCTTCCTGACGCAGTACGGTAAGCTGAAGGACGCTGCAAACGGCTATTTTTCACCGGATGGCTTGCCGTACCATTCGGTAGAAACCTTGATGGTGGAGGCACCTG
ATCATGGCCACCAGACGACCTCTGAAGCCGTCTCCTTCTGGATGTGGTTGGAGGCCGCATACGGTCGAGTAACGGGCGACTGGGCCCCGTTCAATGCAGCGTGGGCA
GTCGCAGAAAAGACCATTATCCCCCAGCATGCGGACCAGTCGACATCCGACTCGTATAACCCGTCCGCACCGGCCACGTATGCACCGGAGCACCCTCTGCCGAGCGG
CTACCCGTCGGCATTGGATGGTACCGTCCCGGTCGGTACAGACCCTCTCAGCGCAGAATTGGCGAGTTCGTATGGAACCATGGACGTGTATGGTATGCATTGGCTCA
TGGATCTGGACAACGTGTATGGTTACGGTAACAAGCCGGGTACGGGTGGAGAGAGCGGTCCCGGCGCAGGAGCGTCGTTCATAAATACCTATCAACGTGGTGCACAG
GAGAGCGTGTGGGAGACGGTACCGCAACCGACGACGGATCTCTTCAAGTACGGAGGGCCGAACGGATACCTGGACTTGTTCGTGGGTGACTCCAGCTACGCGAAACA
ATGGAAGTACACCAACGCACCGGACGCCGATGCACGCGCCGTCCAGGCGGCATACTGGGCATATCGGTGGGCAAGTGAGCAAGGCAAGGAATCGCAGGTGGCAGCAT
CGGTGGCGAAAGCCGCAAAAATGGGTGACTACCTCCGCTATGCCATGTTCGACAAGTATTTCAAGCGAGTCGGAGATTGTACGGACCCAAATAGCTGCCCCGCAGCG
TCGGGTCGCGACAGCCAGCACTACCTGTTGTCGTGGTACTATGCCTGGGGTGGCGCAGCGGCAGGTAGTGGAGGCGGATGGGCCTGGCGTATCGGTGACGGGGCATC
GCACCAGGGATATCAGAACCCGCTTGCAGCATGGGCCCTGAGCAACGTCCCGTCGCTGACCCCGAAGAGTGCAACGGCCCGATCGGATTGGTCCAAGTCGCTGACCC
GCCAACTCGAGTTCTTGACATGGCTGCAGTCAAGCGAGGGCGCCCTGGCAGGGGGTTGCACCAACTCATGGGAAGGCAGCTACTCAACACCCCCGGCCGGAACGCCC
ACTTTCTATGGTATGGCATACGACTGGCAGCCGGTGTATCATGACCCGGCGTCGAATAATTGGTTCGGCTTCCAAGCCTGGGGTATGGAAAGGGTGGCGGCATACTA
CTATGTAACGGGGAACGCAACAGCAGAGGCAGTGCTTTCGAAGTGGGTCGCCTGGGCATCATCGGAAACCACTATTGGATCGGACGGTAGCTTCCGTTTCCCTTCGA
CGCTGAATTGGACCGGGGAACCAGACACCTGGAACGCAGCATCCCCGGGTGATAACGCCGGACTGCATGTGTCAGTCGTAGACTATGCAAATGACGTCGGAGTCGGT
GCGGCGTATGTGAAGACACTCACCTACTACGCAGCGAAGAGCGGAGACGAAGATGCAGCCGCATTGGCAAAGGCCCTGCTCGACGCAATGGCACTCAACACAACCGA
CAAGGGAATCAGTGTCCCGGAAACGCGCCTCGACTACAATCGTTTCGATGACGAGGTCTACATCCCGTCGGGCTGGTCTGGTACAATGCCGAACGGTGACCCCGTCC

FIG. 14 (continued)

Example 2 DNA sequences

GTCCGGGAAGTACTTTCATTTCCATACGGAGCTGGTATAAAGATGACCCAGACTGGCCTAAAGTACAGGCATACCTCGACGGCGGGGATGCGCCGGTATTCACCTAC
CACCGGTTCTGGGCCCAAGCCGCCCTGGCATTGGCATTCGCAATTTATGCGGAACTTCTGGTAGAGGGAGGAGGTGGGGAACCTGGTGGTGACACGGAGCCGCCGAC
CGCACCGGGCGGACTCACCGTAACAGCTACAACGAAGGATAGCGTCTCCCTCAGCTGGTCGGCATCAACCGACAACACAGCAGTGACCGGGTATGACGTGTACCGTA
ATGGAGTACTGGCCGGAAACGCAACAGGCCGCACATTCACGGATAGCGGCCTCGCAGCCAATACGGAATATACATATGCGGTCGCAGCCAGGGACGCAGGTGGGAAT
ACATCTGCGCTGAGCGATGCCGTCCTGGCAAAGACAAAAACAGGTGGGAGCACGGGTACCGGCGCAGTAAAGGTCCAGTATAAGTCGACCGATAGCTCGGCAACTGA
CAACCAAATCCGTATGGGACTGCAAGTAGTCAACACCGGCTCGGCACCGGTAGATCTGTCGACAGTGAAGGTGCGCTATTGGTTCACAGCCGACGGTGGACCCTCCA
CCTTCGGAACATACTGCGACTATGCCGCATTGGGGAGCTCGACGATTACCCACACTGTCGTCGCCGTAAGCTCGCCGAAGACAGGAGCAGACCGATACCTGGAGGTC
GGGTTTACCGGTGGTGCGGGCACACTCGCAGCAGGTGCGTCCACGGGGGAGATCCAATTGCGACTGAACAAGTCGGATTGGTCAAATTTCAACGAGGCCGATGACTA
CAGCCGTGCAACCAATACAGCCTATGCAGATTCGTCTAAGGTAGGGGCCTACGTCGCAGGAGCACTCGCATGGGGAGTCGAACCCTAA

>95 GH5 (SEQ ID NO:30)

ATGCTGCACCCCCTTCGCACATTCCGTCGGGCAGCACGAACCGTCGCGGTAGCCACCGCAGCGCTCCTCCTTCCGCTCGCCGGAGCACATCCGGCCAGTGCAGACGC
CGCACGTGCGGCAGCCGCAGGTTCGGGATATTGGCACACGTCAGGTCGCCAGATCCTGGATGCAGCAAACCAGCCCGTGCGCATCGCAGGAATCAATTGGTTCGGAT
TCGAAACCGCAAACTATGTCCCGCATGGCCTCTGGAGCCGTGACTATAAGTCGATGATCGACCAAATGAGGTCCCTGGGTTATAACACGATCCGTCTGCCGTACTCA
GATGACATATTCGCAGGAACCGAGCCGGCAAGCATCAATTATTCGGCGGGTATGAATACGGATCTCGCAGGTCTGAACTCGCTCCAGGTGATGGACCGTATCGTCGA
CCACGCCGGCAGTTTCGGAATGAAAGTAATCTTGGATAGGCACCGTCCCGACTCCGCAGGTCAGTCGGCACTGTGGTATACCTCCGCGGTACCGGAGAGCACGTGGC
TGGCACATCTCAAGTCACTTGCGGCCCGCTACGCGGGCAATGACGCCGTGGTAGGTATCGACCTCCACAACGAGCCGCACGACCCGGCATGTTGGGGCTGTGGAGAT
ACCACGAAGGACTGGCGTCTCGCCGCGCAGCGCGGTGGAAACGCCGCATTGAGCGCCAATCCGGACCTTCTGATATTCGTCGAGGGGGTGCAGACGGTAGATGGAGT
CTCGGGCTGGTGGGGTGGTAACCTGATGGGAGTGGGACAGTATCCCGTGGAACTGTCTGTGCCGCACAAGGTGGTGTACAGCGCACACGATTACGCAACCAGTGTGG
CACAACAGCCTTGGTTCACGGACAGTTCCTTCCCGGACAATATGCCCGGTGTCTGGGATAAGTATTGGGGCTACATCTTCAAACAGAACATTGCCCCCGTATGGGTA
GGTGAATTCGGAACCACACTGCAGAGTACCACCGACCAGAAATGGCTCAAGGCCCTGGCGGACTATCTGCGACCGACAAGCCAGTACGGAGCAGACTCGTTCAGCTG
GACGTTCTGGTCTTGGAATCCCAACTCGGGTGATACAGGAGGTATCCTCAAGGACGATTGGACGAGTGTCGACACAGTCAAGGACGGATACCTGGCGAGTATCAAGG
CGCCGGACTTCGGTAATGGTGGTGGAAGTGGTGGCGATGACGACACACAGGCCCCGACGGCACCAACAGGACTCGCCGTAACAGGGACAACCGGTACCAGTGTCTCG
CTGAGTTGGAAGGCAGCATCGGACGACACGGGGGTGACAGCGTATGACGTCTACCGCGGTAGCACGAAGGCAGGAACCGCGACAGGTACGACGTTCACAGACACGGG
TGTAACCTCGGGTACGAGTTATACCTATACAGTCCGCGCACGAGACGCGGCAGGAAACACGTCCGCCCCCTCGGCATCGGTAACCGCAACCACGACAGGGTCCGGAG
GAAATACCGGTTGTAAAGCCGTGTACACGGTCAACGGAGACTGGGGGTCGGGATTCGGGGTAGACATCACCGTGACGAACACAGGCACCGCCCCGGCAACGAGCTGG
AAGTTGACATGGACCTACGGTGGCTCGCAGAAAATAACGAATATGTGGAACGCAAGCTATACCCAGTCAGGCGCCTCCGTGACCGTAACATCTACAGACTACAATGG
AGGACTCGCGGCAGGGGCACACACCGGCTTCGGTTTCCAGGGAACACCCGCGGCGGGCGCAGTCCCAACCGTGTCCTGTACGCTGAGTTAA

>95 GH9 (SEQ ID NO:31)

ATGCGAAGTTTCCCCCTGCCCGCGCTGAGGAGACGGAGTCGGCGGCCCGGACGTCCCCTCGGAGCAGTCGCCTTGGCCCTGGCAGTCGGCGCCGGTCTGCTGCTCCC
GTTGTCGCTGCCGGCCGGAGCAGCAGCGGCACCGGCCTTCGACTATGGAGAAGCCTTGCAGAAGTCGGTACTGTTCTACGAGGCCCAGCAATCAGGAAAGTTGCCGG
ATACGAACAGGGTGAGCTGGCGCGGCGACAGCGCACTCGACGATGGTAAAGACGCCGGACTGGACCTCACCGGAGGTTGGTATGACGCCGGCGACCACGTAAAGTTC
GGGCTGCCAATGGCATACTCAGCAACGATGCTGGCATGGGGTGGCACCGAACAACGCGCCGCGTACGAAGCAAGCGGACAGCTGCCCCATCTGCGCAATAACTTGCG
TTTCGTAGACGACTATCTGCTGAAGGCGCACCCGTCACCGAATGTCTTGTACGGACAAGTCGGAAATGGAGGTGACGATCATAAGTGGTGGGGACCGGCAGAAGTAA
TGCCGATGAAGCGGCCGGCGTATAAAATAGACGCATCCTGCCCGGGTAGCGACCTGGCGGGTCAGACCGCCGCAGCGCTCGCAAGTTCGTCCATGGTGTTCTCGGAC
AGTGACCCCGCCTACGCCGCAAAATTGATTACACACGCAAAGCAACTGTACACCTTCGCGGACACGTATCGCGGCAAGTACTCGGACTGTATCACGGACGCACAGTC

FIG. 14 (continued)

Example 2 DNA sequences

GTACTACAACTCCTGGAGCGGCTATAATGATGAGTTGGTATGGGGCGCGATCTGGCTTTACAAAGCAACCGGAGACACCGCCTACCTGGCAAAGGCCGAGTCCTATT
ACGACAACCTCTCGACCGAACCGCAGACAACGACGCGATCATATCGCTGGACCTTGTCGTGGGATGACACCTCCTACGGCGCGTATGTCCTTCTCGCACAACTCACG
GGAAAACAGAAGTACATTGACGACGCAAATCGGTGGTTGGACTGGTGGACCGTGGGAGTCAACGGACAGCGCGTGCCCTATAGCCCGGGTGGTCAGGCAGTACTGGA
TAGCTGGGGTAGTCTGCGGTACGCCGCCAACACCGCGTTCGTAGCACTCAGCTACTCCGACTGGCTGACAGGTGACGCAACGCGTAAGGCCCGGTACCACGATTTCG
CCGTGCGCCAGATCGACTATGCACTCGGAGATAATCCGCGAGGATCGTCCTATGTCGTCGGTTTCGGCGAGAACCCACCCACCAAACCGCACCATCGTACGGCGCAC
GGTTCGTGGACCGACCAAATGACCAATCCGGTGGAGACGCGCCACACGCTGTACGGAGCACTGGTAGGCGGACCCTCAGCCCCAGACGATACCTATACAGACGACCG
AGGGAACTACGTCAATAACGAGGTGGCAACCGACTACAACGCGGCCTTCACTGGAGCGTTGGCACGACTGTATGCGGAGTACGGAGGTTCGCCCCTCACCGACTTCC
CTCAGCCGGAAGAGCCCGACGGACCGGAAATGAGCGTCCAGGCATCTGTAAATGCAGCGGGAGCCAACTTCACAGAGGTGAAGGCGTATCTTATTAACCGAAGTGCC
TGGCCAGCACGCGCACTCACAGATGCAAGCGTCCGATATTACTTCACCCTGGAACCGGGAGTCGCCCCGGGAGACATTAGTTTCACGACAAACTATAATCAATGCGG
CGAGGTCACCGGCCCTACGCACCTGACAGGAGATGTCTACTATGCAACCGTCGACTGTTCAGACACAGACATCGCCCCGGCCGGCCAGAGCGCATACCGTAAAGAAG
TGCAGTTCCGCATCTCCAGCGCAGGTGCATGGGATCCTTCCAACGACTGGTCGTATCCGAGCACGGCAACTACCCCCGGAGGTACGCCGGTCGACGCCCCCCATATG
GTACTCCTTGAGGGTTCGGCGCCGCAGTGGGGACGGCCCCTGATGGAACCGACCCGGGACCAGGTCCGGACCCTACCACAACGCCGGAACCATCCCCGACGCCAGA
CCCAACCGATACACCCGACCCGGAACCTGGAGCATGCGATGTCACCTACCGAGTGTCGCAGGCATGGGGTACAGGGTTCACCGCGGACGTCACAGTCAAGAATACGG
GACCGACCCCCCTCGACGGATGGCAGCTTGCATTCGACTTCCAGGGAGCCGAGAGTGTATCGAACGCGTGGAACGCCACCGCGACGCAGAGTGGAACTAGGGTGACC
CTCAAGAACGCAGGTCACAACGGCTCGGTGCCGGCAGGTGGTTCCGCCTCGTTCGGCTTCCAGGCGAACGGGGCCCCCGGAGCAGACCCGCATAGTTTCACATTGAA
CGGAAAGGAATGTGGTTGA

>95 GH12 (SEQ ID NO:32)

ATGACAGGCCGGCCGCTGCCGGCATTGGCAGGAGCGGCAGCCGCACTGGTCCTGGCGGCGGCAAGCATGCTGACCGGAGCGAGCTCCGCAAGCGCGTCGCCGGTGAC
CGATTGTACACCGTGGGGTACAACGGAGCTCCTCGGTGGGGAGTACTTGTATCAGCAGAACGAGTGGAACTCGGACAGCGAACAATGTGTCGGAGTGGACCCGGACA
CCGGAGCCTGGAGCGTAACAACAAGCAGCTTCAATCTTCCCACAAACGGCGCACCAGCCACGTACCCGAGCAGCTATAAGGGATGCCACTGGGGGCATGTACCTCG
GATTCTGGACTGCCGCTCCGCGTGGACGAGTTGGGATCAGTACATACAGACTGGTCGACCACACAGGTAGGCTCCGGTGCCTATAATGTGAGTATGGACGTCTGGTT
TAACAGTGCACCTGTAACGGATGACCAGCCGGACGGCACGGAACTGATGATCTGGATGAACCACCGCGGTGGAGTGCAGCCCATTGGAAGCCGTACGGCCACAGTCC
AGCTCGATGGTCGCACGTGGGACGTATGGACCGGACCCGGCGCATCGGGATGGAAGGTCATCAGTTACGTCTTGCAGGGCGGAGCGACCGAGCTCACAGGGTTCGAT
GTGAAGTCGTTGATCGACGACGGAGTGGGTCGTGGCCAAATAGACCCGGCCCATTATCTCATCGACGCAGAGGCCGGATTCGAGATCTGGCAGGGTGGCCAGGGGCT
GGGTATGAAAGAGTTCAGCTTCGAGGCCAGCGCAGGAACCGACGGTGGCGATGACGGAGGCGACGGCGATCCGGGCGGCGGAGGCACCACAGGAGCACTCAAGGCCC
AGTACAAAAATAACGATTCCAGCGCGACGGACAATCAGATACGCCCAGGCCTGCAGCTCGTGAATACCGGATCCACAGCTGTCGACCTGTCTACTGTGAAGCTGCGG
TACTGGTTCACCCCCGAAAGTGGCGCGGCGGGTTTCGGCACGGCCTGTGATTATGCAGTCGTCGGTTGTGGAAACGTCACGCACACGGTAAAGCAAGCAGGGACGGC
AGCCGGCGCATCACACTACTTGGAGGTGGGTTTCACGGGCGGATCGCTGGCCCCGGGTGCATCGACCGGTGAAATTCAGCTGCGATTCAACAAGTCGGATTGGTCGG
CGTTCGACGAAGCCGACGACTACAGTCGTGCAGCGAACACGGCGTTCACCGACGCATCGAAGGTGGGTGTCTACGTGAATGGAGCATTGTCAAGCGGTACAGCGCCG
TGA

FIG. 14 (continued)

METHOD OF CREATING INDUSTRIAL STREPTOMYCES WITH CAPABILITY TO GROW ON CELLULOSIC POLYSACCHARIDE SUBSTRATES

CROSS-REFERENCE TO RELATED APPLICATIONS

This application claims priority to U.S. Provisional Application No. 62/318,399 filed on Apr. 5, 2016, the contents of which are incorporated by reference in its entirety.

STATEMENT REGARDING FEDERALLY FUNDED RESEARCH

This invention was made with government support under DE-FC02-07ER64494 awarded by the US Department of Energy. The government has certain rights in the invention.

BACKGROUND

Cellulose is the most abundant organic polymer on Earth and represents a vast source of renewable energy. Most of this energy is stored in the recalcitrant polysaccharide cellulose, which is difficult to hydrolyze because of the highly crystalline structure, and in hemicellulose, which presents challenges because of its structural diversity and complexity. Plant cell walls, approximately composed in pinewood of lignin (30% by weight), hemicellulose (glucomannan, 20%, arabinoxylan, 10%), and crystalline cellulose (40%), present a major barrier to its efficient use. In terrestrial ecosystems, cellulolytic microbes help drive carbon cycling through the deconstruction of biomass into simple sugars. The deconstruction is largely accomplished through the action of combinations of secreted glycoside hydrolases (GHs), carbohydrate esterases (CEs), polysaccharide lyases (PLs), and carbohydrate binding modules (CBMs). Consequently, organisms from many lignocellulose-rich environments and their enzymes are being studied for new insights into overcoming this barrier.

In order to obtain the hydrolysis of crystalline cellulose, enzymes must cleave three types of glycosidic bonds. These enzymes are endocellulases, which cleave beta-1,4 glycosidic bonds that reside within intact cellulose strands in the crystalline face, non-reducing-end exocellulases, which remove cellobiose units from the non-reducing end of cellulose strands, and reducing-end exocellulases, which remove glycosyl units from the reducing-end of a cellulose strand. The endocellulolytic reaction is essential because it creates the non-reducing and reducing ends that serve as the starting point for exocellulolytic reactions. The exocellulolytic reactions are essential because they remove glycosyl groups in a processive manner from the breakages in the cellulose strand introduced by the endocellulases, thus amplifying the single initiating reaction of the endocellulases.

Although a large number of *Streptomyces* species can grow on biomass, only a small percentage (14%) have been shown to efficiently degrade crystalline cellulose. Furthermore, the secreted cellulolytic activities of only a few species have been biochemically characterized, and still fewer species have been examined to identify key biomass degrading enzymes. For example, *Streptomyces reticuli* is one of the best-studied cellulose- and chitin-degrading soil-dwelling *Streptomyces*; functional analyses of several important cellulases and other hydrolytic enzymes have been reported.

Furthermore, polysaccharide monooxygenase (PMO) activity with cellulose was identified using the CBM33 protein from *Streptomyces coelicolor* (Forsberg, et al., 2011), which suggests *Streptomyces* may use both hydrolytic and oxidative enzymes to deconstruct biomass. With the tremendous amount of sequence data collected in the past few years, and despite the view that *Streptomyces* make important contributions to cellulose degradation in the soil, genome-wide analyses of cellulolytic *Streptomyces* are only recently being reported. For example, see Book, et al, Appl Environ Microbiol 80:4692-4701, 2014.

In addition to their putative roles in carbon cycling in the soil, *Streptomyces* may also potentiate biomass deconstruction in insects through symbiotic associations. Recent work has identified cellulose degrading *Streptomyces* associated with the pine-boring woodwasp *Sirex noctilio*, including *Streptomyces* sp. SirexAA-E (ActE) (Adams, et al., 2011). *S. noctilio* is a highly destructive wood-feeding insect that is found throughout forests in Eurasia and North Africa and is spreading invasively in North America and elsewhere. While the wasp itself does not produce cellulolytic enzymes, evidence supports the role of a symbiotic microbial community that secretes biomass-degrading enzymes to facilitate nutrient acquisition for developing larvae in the pine tree.

The white rot fungus, *Amylostereum areolatum*, is the best-described member of this community, and the success of *Sirex* infestations is thought to arise from the insect's association with this cellulolytic fungal mutualist. However, work with pure cultures has suggested that ActE and other Sirex-associated *Streptomyces* are more cellulolytic than *A. areolatum*.

Needed in the art are improved compositions and organisms for digestion of lignocellulosic materials. Specifically, there is a need for industrialized *Streptomyces* that can accept a greater complexity of less-expensive feedstocks.

DESCRIPTION OF THE FIGURES

This patent application file contains at least one drawing executed in color. Copies of this patent or patent application publication with color drawing(s) will be provided by the Office upon request and payment of the necessary fee.

FIG. 11 is a diagram disclosing the presence of genes assigned from direct Illumina sequencing of *S. lividans* harboring combinatorial cellulolytic operons.

FIG. 13 is a document listing the protein sequences examined in Example 2.

FIG. 14 is a document listing the DNA sequences examined in Example 2.

DESCRIPTION OF THE INVENTION

In one embodiment, the present invention is an optimized set of enzymes useful to create an industrial *Streptomyces* with the capability to grow on cellulosic polysaccharide substrates.

In General

The Examples below disclose several embodiments of the present invention, which is a general strategy for providing an optimized set of heterologous genes (encoding an optimized set of enzymes) for transformation into a host *Streptomyces* species.

Figures 1A, 1B, 1C:
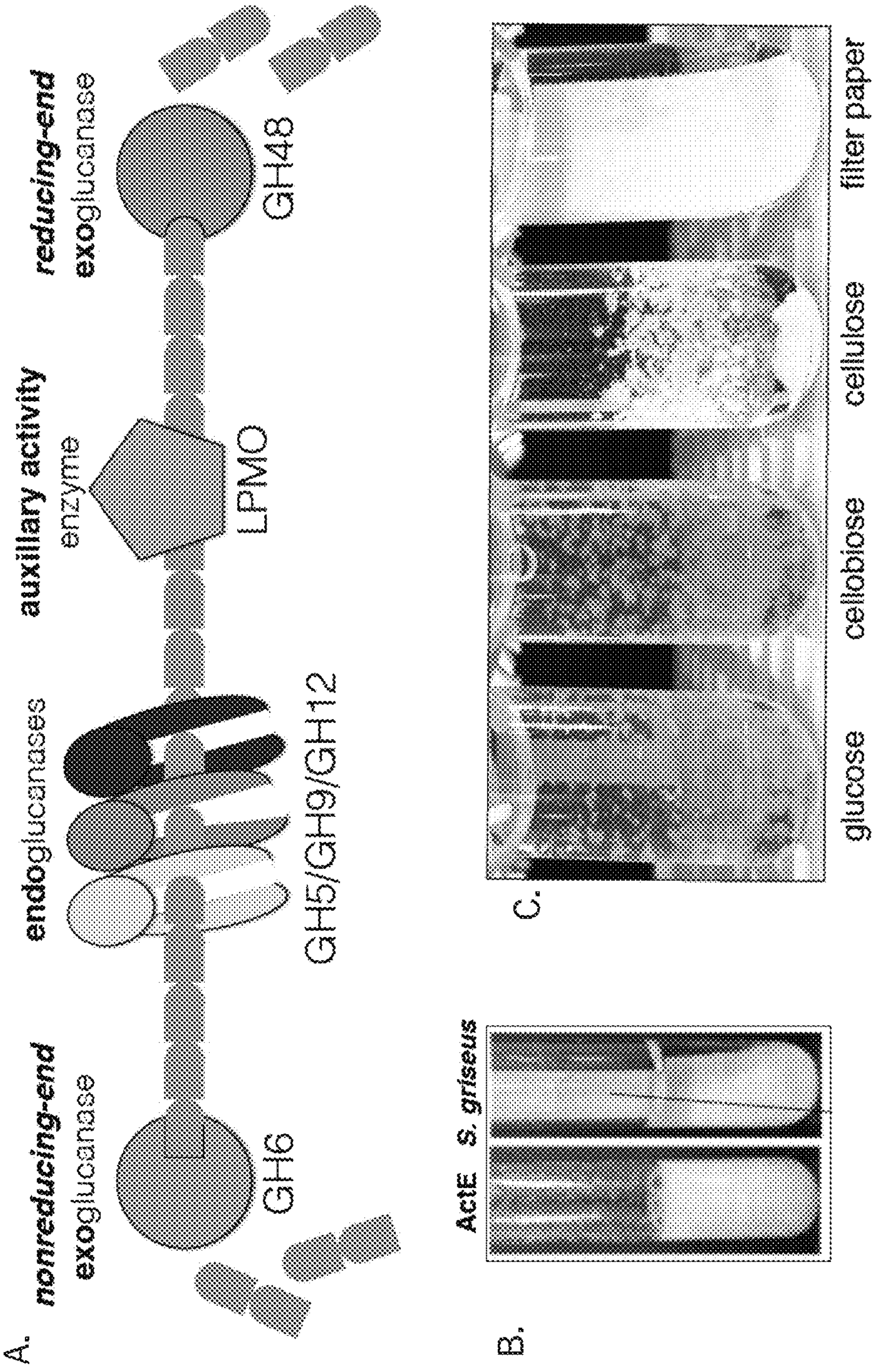
FIGS. 1A-1C are a demonstration of highly cellulolytic *Streptomyces* strains that contain suites of enzymes lacking in industrialized strains that are necessary to consume cellulose as a food source. (A) is a model for enzymatic hydrolysis of cellulose using up to five enzymes. (B) is an example of a cellulolytic *Streptomyces* and a non-cellulolytic *Streptomyces* when cultured on filter paper as the sole carbon source. The cellulolytic *Streptomyces* is capable of growth and degradation of filter paper. (C) is an example of a non-cellulolytic *Streptomyces* cultured with four different carbon sources, and the strain is only capable of growth on glucose and cellobiose.

As disclosed in FIG. 1, one suitable enzyme cassette comprises (1) a non-reducing-end exoglucanase from the GH6 family, (2) endoglucanase from the GH5 and/or GH12 families, (3) an endoglucanase from the GH9 family, (4) an auxiliary activity enzyme from the AA10 family, and (5) a reducing-end exoglucanase from the GH48 family. The preferred enzyme cassette requires two different endoglucanases because these distinct enzyme fold families provide variations in catalytic properties that contribute to enhanced cellulolytic capability. An AA10 enzyme uses copper(II) ions, reducing agents and O2 gas to degrade cellulose in an oxidative manner that is complementary to the hydrolytic reactions carried out by the GH family enzymes. In a preferred embodiment, the genes in the cassette are not from a single species.

A second embodiment of the present invention is a heterologous gene cassette wherein at least two of the enzymes described in (1)-(5), above, are present in the cassette. Preferably, the cassette comprises the endoglucanase from the GH9 family, preferably isolated from *Streptomyces* LaPpAH-95, and an endoglucanase from the GH5 and/or GH12 families, preferably the GH12 endoglucanase isolated from *Streptomyces* DpondAA-B6. In another embodiment, the cassette comprises ActE-GH5, B6-GH9, and B6-GH12, as described below in the Examples.

By "the capability of growing on cellulosic polysaccharide substrates," we mean that the transformed organism is better able to grow on biomass, preferably at least one of the following substrates: cellulose, hemicellulose, paper, or wood products. Biomass is generally defined as organic materials, such as plant matter and manure, which have not become fossilized and can be used as a fuel or energy source. Of particular importance to the present invention is biomass composed of plant material, vegetation, or agricultural waste. Wood is the largest biomass energy source. Forest residues (such as dead trees, branches and tree stumps), yard clippings, and wood chips are all examples of wood biomass. Non-wood biomass includes plant or animal matter that can be converted into fibers or other industrial chemicals, including biofuels. Non-wood biomass can be grown from numerous types of plants, including miscanthus, switchgrass, hemp, corn, poplar, and willow.

Other substrates include corn stover, prickly pear cactus cladodes, kelp, sorghum, straw, poplar, eucalyptus, pine, sugarcane bagasse, cotton, bamboo, nut shells, bark, sawdust, wood chips, and paper mill waste. In the Examples below, the model cellulosic polysaccharide substrate is phosphoric acid-swollen cellulose (PASO). The ability of an organism to degrade this substrate would be useful to understand whether a recombinant organism is within the scope of the present invention.

We specifically envision that the present invention will be useful for treated (or pretreated) and untreated biomass. Preferably, the organism is able to break down insoluble, recalcitrant polysaccharides such as cellulose, hemicellulose, and mixed polysaccharide biomass to produce small oligomeric and/or monomeric, soluble sugars that it can import for use as a nutritional carbon source. This in turn is utilized by the cell for the increased production of cellulolytic enzymes, increased cell growth density, and/or for the production of other value-added metabolites. Cellulolytic activity may be measured as described below in the Examples or by other methods known to those of skill in the art.

By "heterologous," we mean that the genes in the cassette do not naturally occur in the host species.

Specific Combinations of Enzymes

The Examples below disclose particularly advantageous combinations of heterologous enzymes, preferably presented to the host *Streptomyces* as an operon or cassette. In one embodiment, each operon typically comprises at least two members selected from a GH6 gene, a PMO gene, a GH48 gene, a GH5 gene and either (a) a GH9 gene, (b) a GH9 gene and a GH12 gene or (c) a GH12 gene. Many of the CAZy (Carbohydrate-Active enZYmes database) classes (for example, GH5, GH6, etc.) contain multiple types of enzymes, unified by their general type of reaction and diversified by substrate specificity and product formation. Table 1, below, describes preferred members of the classes. Preferably, the genes are obtained from more than one species.

TABLE 1

| CAZy gene class | Enzyme name | Enzyme Commission (EC) # | Reaction mechanism | GH catalytic proton donor | GH catalytic nucleophile/ base | protein fold clan | structural class | Add'l specs |
|---|---|---|---|---|---|---|---|---|
| GH5 | endo-beta-1,4-glucanase | EC 3.2.1.4 | Retaining hydrolysis | Glu | Glu | GH-A | (beta/alpha) 8 | |
| GH6 | non-reducing end cellobiohydrolase | EC 3.2.1.91 | Inverting hydrolysis | Asp | Asp | | | processive |
| GH9 | endoglucanase | EC 3.2.1.4 | Inverting hydrolysis | Glu | Asp | | (alpha/alpha) 6 | |
| GH12 | endoglucanase | EC 3.2.1.4 | Retaining hydrolysis | Glu | Glu | | beta-jelly roll | |
| GH48 | reducing-end cellobiohydrolase | EC 3.2.1.176 | Inverting hydrolysis | Glu | | GH-M | (alpha/alpha) 6 | processive |
| AA10 | copper-dependent lytic polysaccharide monooxygenase (LPMO) | | Oxidative | Not applicable | Not applicable | | | previously called CBM33, PMO or LPMO |

In one embodiment of the invention, the genes encoding the CAZy classes are selected from highly-cellulolytic *Streptomyces* strains, such as the insect-associated strains *Streptomyces* sp SirexAA-E (ActE), *Streptomyces* DpondAA-B6, and *Streptomyces* LaPpAH-95. Preferred embodiments are listed in Example 2. The paragraph below includes each of the enzymes in Example 2 listing their NCBI reference numbers. This reference number can be searched at the NCBI website to find the exact protein sequence used to create synthesized/optimized DNA. FIG. 13 is a document listing the protein sequences for the Example 2 experiments (SEQ ID NO:1 and 3-17) and FIG. 14 is a document listing the DNA sequences after optimization (SEQ ID NO:2 and 18-32).

| Organism | CAZy Family | NCBI Reference Number |
|---|---|---|
| ActE | GH48 | AEN08183.1 |
| ActE | GH5 | AEN08423.1 |
| ActE | GH6 | AEN08184.1 |
| ActE | GH9 | AEN11565.1 |
| ActE | LPMO | AEN11025.1 |
| DpondAA-B6 | GH12 | WP_028441901.1 |
| DpondAA-B6 | GH48 | WP_028441980.1 |
| DpondAA-B6 | GH6 | WP_078552084.1 |
| DpondAA-B6 | GH9 | WP_028439469.1 |
| DpondAA-B6 | LPMO | WP_028441526.1 |
| LaPpAH-95 | GH12 | WP_018105227.1 |
| LaPpAH-95 | GH48 | WP_018105228.1 |
| LaPpAH-95 | GH5 | WP_018104961.1 |
| LaPpAH-95 | GH6 | WP_026171800.1 |
| LaPpAH-95 | GH9 | WP_018105029.1 |
| LaPpAH-95 | LPMO | WP_018099987.1 |

In another embodiment of the invention, the genes are selected from *Streptomyces* clades I and III (the cellulolytic clades). For more information, see Book A J, Lewin G R, McDonald B R, Takasuka T E, Wendt-Pienkowski E, Doering D T, Suh S, Raffa K F, Fox B G, Currie C R. 2016. Evolution of high cellulolytic activity in symbiotic *Streptomyces* through selection of expanded gene content and coordinated gene expression.

Figure 3:
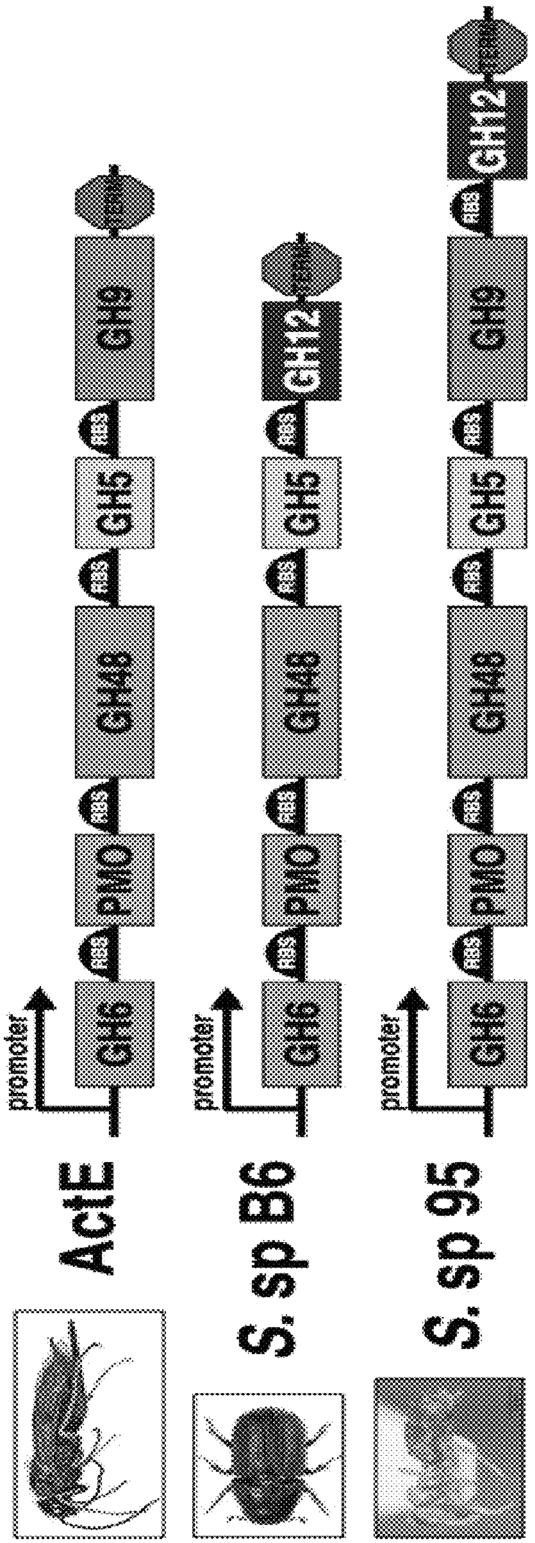
FIG. 3 discloses three optimized synthetic operons designed to express cellulase enzyme sets from three insect-associated *Streptomyces* strains that were generated by artificial gene synthesis for heterologous expression in industrialized, non-cellulolytic *Streptomyces* hosts. ActE (*Sirex* woodwasp), *Streptomyces* sp. DpondAA-B6 (*Dendroctonus ponderosae* mountain pine beetle), and *Streptomyces* sp. LaPpAH-95 (*Petalomyrmex phylax* ant) are *Streptomyces* strains isolated from their respective insect associations and are characterized by high natural cellulolytic abilities.

In three specific preferred combination, the gene cassettes are as disclosed in FIG. 3.

The enzyme combination of the present invention is optimally presented to the *Streptomyces* as a gene cassette, preferably under the control of a single constitutive promoter, such as the ermE* promoter described below. Other useful elements include the use of ribosomal binding site (RBS) sequences. A successful operon must have a promoter in order to initiate transcription of the subsequent genes. Many promoters could substitute for the ermE promoter used in the Examples. We chose one of the most commonly-used promoters for genetic engineering in these organisms. A terminator at the end is desirable to increase the stability of the transcript and to allow RNA polymerase to finish a transcript and begin a new one. Likely many different kinds of terminators could substitute. Many studies do not include a terminator and generate acceptable results. Every gene requires an RBS for the ribosome to bind the transcript and initiate translation at the next start codon. Random sequence upstream of a gene will initiate ribosome binding at an extremely low rate, so sequence that is tailored to attract ribosomes is essential for efficient enzyme production.

In a preferred version of the present invention, the gene order is the same as that disclosed below in the Examples. We chose a gene order based on wild-type expression of the enzymes in the ActE organism (from highest expressed to lowest) and then continued that pattern with the homologous genes from B6 and 95 strains. However, this gene order does not exist in nature. The preferred gene optimization is designed to minimize a gene order effect by altering repetitive sequence that could affect translation of each gene and neighboring genes.

In a preferred version of the present invention, the genes are subjected to a gene optimization strategy to substantially optimize enzyme expression compared to the wild-type sequences. In the case of wild-type genes that don't appear to express in the host strain, "substantially" optimized means that expression is high enough to be clearly detectable from a 10 uL load on a Coomassie Stained SDS-PAGE gel after 10-fold concentration of cell supernatant. The minimum level for this detection is approximately 10 ug/mL (assuming 100 ng comprises a clearly detectable protein band). A substantial improvement in expression of a wild-type gene that does express in the host at a low level would be at least two times higher that this low threshold.

One typical optimization would be to change any alternative start codons (TTG, GTG, or CTG) to the standard ATG start codon. Another optimization would alter codon usage to remove repetitive sequence that is predicted to produce transcript hairpins which can interfere with translation. One may also wish to modify codon usage to substitute rare codons (e.g. TTA) to preferred codons or to alter codon usage to facilitate artificial gene synthesis. These modifications are predicted to substantially optimize enzyme expression compared to the wild-type sequences.

One may wish to consult gene optimization strategies utilizing the GeneDesign tool (http://genedesign.jbei.org), the in-house JGI Sequence Polishing Library tool, or manual manipulations to accomplish the above objectives. The cassettes of the present invention are then introduced into a host *Streptomyces* in any suitable manner. One of skill in the art would understand that there are numerous suitable ways to achieve this result. One suitable reference would be the book Practical *Streptomyces* Genetics by Kieser T, Bibb M J, Buttner M J, Cjater K F, and Hopwood D A (2000). The important techniques include protoplast transformation and conjugation from *E. coli*. There are other techniques as well, all described in chapter 10, "Introduction of DNA into *Streptomyces*".

Suitable *Streptomyces* Host Strains

As described below, particularly suitable *Streptomyces* strains are *S. lividans* or *S. venezuelae* strains. However, other commercially important *Streptomyces* are *S. coelicolor* and *S. griseus*. Other suitable strains include *Streptomyces clavuligerus, Streptomyces hygroscopicus*, and *Streptomyces viridochromogenes*, and *Streptomyces avermitilis*.

EXAMPLES

Example 1

Optimized Set of Enzymes

FIGS. 1 through 5 disclose a set of experiments designed to discover an optimized set of enzymes useful to create an industrial *Streptomyces* with the capability to grow on cellulosic polysaccharide substrates.

FIG. 1 is a demonstration of an essential suite of enzymes from highly cellulolytic *Streptomyces* strains that are necessary to consume cellulose as a food source. These enzymes are lacking in industrialized strains such as *Streptomyces griseus, Streptomyces venezuelae* and others. Referring to FIG. 1, (A) is a schematic showing a single cellulose chain being deconstructed into cellobiose units (composed of two beta-1,4-linked glucose units) by the critical enzymes classes that aid in cellulose consumption by natural highly cellulolytic *Streptomyces* strains. (B) demonstrates that the wood wasp-associated *Streptomyces* sp. SirexAA-E (ActE) consumes a 1×10 cm cellulose filter paper strip as the sole carbon source in under 5 days, while the industrialized *Streptomyces griseus*, lacking the critical suite of functional enzymes, is unable to efficiently grow. (C) depicts industrialized *Streptomyces venezuelae* strain readily growing when glucose or cellobiose is the sole carbon source but lacking functional celluloytic enzymes to efficiently grow using cellulose or filter paper as the sole carbon source, as evidenced by the absence of mycelial clumping.

Figures 2A, 2B:
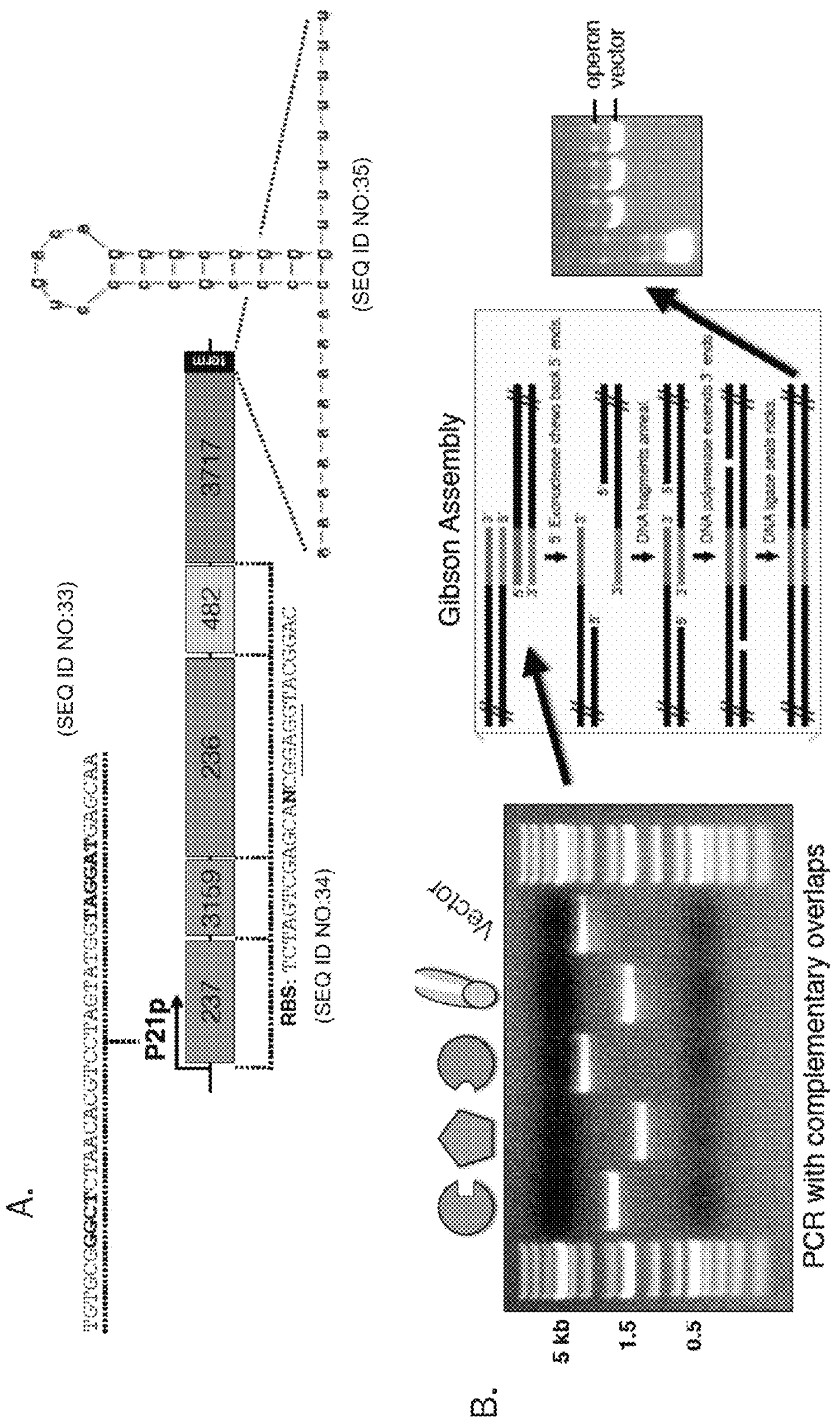
FIGS. 2A-2B show standard cloning techniques that we used to produce synthetic operons containing cellulolytic genes from ActE to enable non-cellulolytic *Streptomyces* strains to produce functional cellulase enzymes. (A) is a diagram showing an example synthetic operon with promoter, genes, RBS (ribosome binding sequences), and terminator sequences. (B) shows a mechanism for cloning the genes via PCR from genomic DNA and assembling using Gibson assembly to create an operon like FIG. 2A. PCR from genomic DNA is one way to generate genetic material for construction of these operons. Another way is DNA synthesis (including codon optimization) as in FIG. 4.

FIG. 2 shows standard cloning techniques that we used to produce synthetic operons containing cellulolytic genes from ActE to enable non-cellulolytic *Streptomyces* strains to produce functional cellulase enzymes. Referring to FIG. 2, (A) is a diagram showing an operon designed to express five specific ActE cellulase genes in *Streptomyces* [Gene ID number (CAZy enzyme class)]: SACTE_0237 (GH6); SACTE_3159 (LPMO); SACTE_0236 (GH48); SACTE_0482 (GH5); and SACTE_3717 (GH9). The five genes are critical for the cellulolytic capabilities of ActE based on proteomic and transcriptomic analyses and have non-redundant biochemical functions. The synthetic operon also contains a constitutive high-expression promoter (P21p or ermE*, Siegl et al., 2013), ribosome-binding-site sequences (from Siegl et al., 2013 or calculated for each gene as in Espah Borujeni et al., 2014), and the synthetic terminator BBa_B1006 (Cambray et al., 2013). (B) shows the result of ActE cellulase genes amplified with complementary overlapping sequences and assembled with New England Biosciences NEBuilder HiFi DNA Assembly to produce complete synthetic operons. The arrangement of these genes does not exist in nature, as they are under the control of different promotors, have different RBS sequences, and can be transcribed in opposite directions. The arrangement we've created takes advantage of placing the most highly expressed natural protein as the first gene.

FIG. 3 discloses optimized synthetic operons designed to express cellulase enzyme sets from three different insect-associated *Streptomyces* strains. These enzyme sets were generated by artificial gene synthesis for heterologous expression in industrialized, non-cellulolytic *Streptomyces* hosts. ActE (Sirex woodwasp), *Streptomyces* sp. DpondAA-B6 (*Dendroctonus ponderosae* mountain pine beetle), and *Streptomyces* sp. LaPpAH-95 (*Petalomyrmex phylax* ant) are *Streptomyces* strains isolated from their respective insect associations and are characterized by high natural cellulolyic abilities. Transcriptomic and/or proteomic analyses of these strains revealed high-abundance cellulases of CAZy enzyme classes (http://cazy.org): GH6; AA10 (also abbreviated as LPMO or PMO); GH48; GH5; GH9; and GH12. Synthetic operons were designed to include the ermE* promoter, gene sequences with optimized RBS spacers (calculated by Espah Borujeni et al., 2014), and the synthetic terminator BBa_B1006 (Cambray et al., 2013). The complete synthetic operons were synthesized as a service by the Joint Genome Institute (JGI) and inserted into the pSET152 vector for integration into industrialized host strains *Streptomyces lividans* and *Streptomyces venezuelae*. (See Bierman et al, 1992, Gene 116:43-49, for information about pSET152.)

Figure 4:
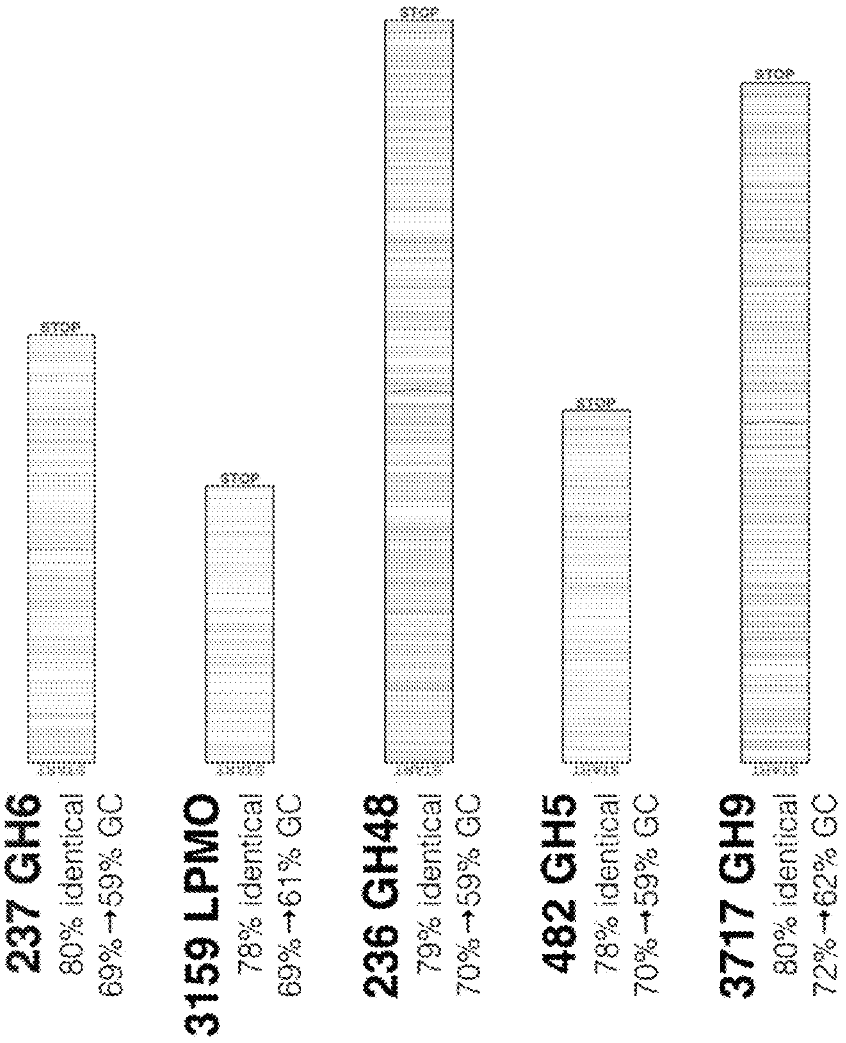
FIG. 4 is a schematic diagram of the gene sequences for synthetic operons that were optimized for highest predicted expression in industrialized *Streptomyces* host strains.

FIG. 4 is a schematic diagram of the gene sequences for synthetic operons that were optimized for highest predicted expression in industrialized *Streptomyces* host strains. The gene sequences specified in FIG. 3 were subjected to a gene optimization strategy to 1) change any alternative start codons (TTG, GTG, or CTG) to the standard ATG start codon, 2) alter codon usage to remove repetitive sequence that is predicted to produce transcript hairpins which can interfere with translation, 3) modify codon usage to substitute rare codons (e.g. TTA) to preferred codons, and 4) alter codon usage to facilitate artificial gene synthesis. These modifications are predicted to substantially optimize enzyme expression compared to the wild-type sequences. The gene optimization strategy utilized the GeneDesign tool (http://genedesign.jbei.org), the in-house JGI Sequence Polishing Library tool, and manual manipulations to accomplish the above objectives.

As an example of the optimization strategy, ActE genes SACTE_0237 (GH6), SACTE_3159 (LPMO), SACTE_0236 (GH48), SACTE_0482 (GH5), and SACTE_3717 (GH9) are depicted with shaded lines (referring to FIG. 4) indicating the positions of nucleotide substitutions, the percent identity between wild-type and optimized sequences, and the change in GC nucleotide content after optimization. See Exhibit D of Ser. No. 62/318,399 for exemplary optimized gene sequences.

Figure 5:
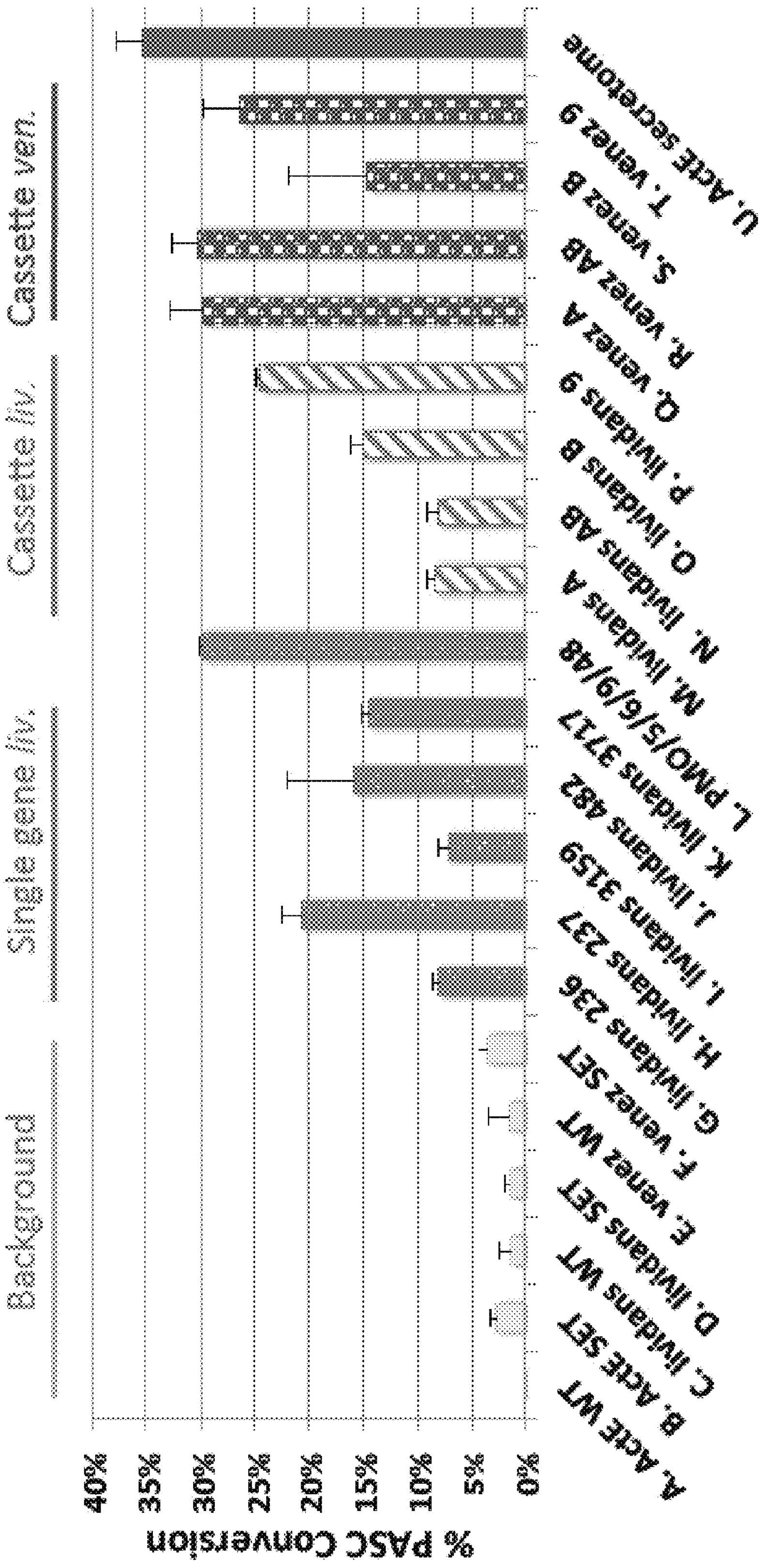
FIG. 5 is a summary graph of the activity of secretomes from industrial *Streptomyces* expressing single ActE cellulases or gene cassettes as described above and in the Examples.

FIG. 5 is a summary graph of the activity of secretomes from industrial *Streptomyces* expressing single ActE cellulases or gene cassettes as described above. Expression of single genes or the entire gene cassette is under control of a single constitutive ermE* promoter (Siegl et al., 2013). The importance of the cellulolytic genes in creating an active secretome was established by control experiments (FIG. 5, A-F) using wild-type (WT) ActE (A.), *S. lividans* (C.), and *S. venezuelae* (E.) or these same strains transformed with empty pSET152 vector lacking cellulolytic genes (SET) ActE (B.), *S. lividans* (D.), and *S. venezuelae* (F.).

Secretomes were prepared in the following manner. 50-mL cultures of individual ActE, *S. lividans* or *S. venezuelae* WT, SET, individual cellulolytic gene, or cassette transformants were grown in YEME (yeast extract/malt extract media, Kieser et al.) (medium with 0.05% antifoam A for 4 d at 28° C. with shaking at 275 rpm. Cultures were treated with protease inhibitor cocktail (Roche complete EDTA-free), centrifuged twice for 30 minutes at 4° C. and 4,300×g, and vacuum-filtered through a glass pre-filter followed by a 0.2 micron PES filter.

The filtrates were concentrated at 4° C. using Vivaspin Turbo-15 PES 10,000 MWCO centrifugal concentrators (Sartorius Stedim) to 2-3% of the starting volume, and exchanged three times using 10 mM MOPS, pH 7, 50 mM NaCl to lower reducing sugar levels in the media. Desalted secretomes were concentrated to approximately 2 mL volume and analyzed by SDS-PAGE to determine the secreted protein expression profile. Total protein concentration was measured using a Bio-Rad protein assay.

Cellulolytic activity was measured using the 3,5-dinitrosalicylic acid assay (DNS; Miller, 1959) to detect reducing sugar products. Briefly, 20 pg of total secretome protein was combined with 500 pg of phosphoric acid-swollen cellulose (PASC), 10 mM MES, pH 6, 5 mM ascorbate, and 0.025% sodium azide in a volume of 50 μL. Duplicate reactions were incubated at 42° C. for 22 h with agitation. Individual secretomes, prepared as described above, were used in all cellulolytic activity assays with the exception of PMO/5/6/9/48, which contained roughly equimolar mixtures of secretomes G., H., I., J., and K. for a total load of 20 pg protein. The ActE secretome positive control consists of 20 pg of purified ActE secretome harvested from a 6 d growth of ActE on 0.3% PASC in M63 defined medium.

Cellulolytic activity assays were briefly centrifuged and 30 μL of the soluble fractions were combined with 60 μL of DNS reagent in a microplate alongside glucose concentration standards, heated to 95° C. for 5 min, then cooled to 4° C. Reactions were diluted 7.5-fold with water and the absorbance at 540 nm was measured using a Tecan plate reader. The concentration of reducing sugar was determined from a linear plot of standard absorbance versus concentration. The percentage conversion was determined following background correction from no-substrate and no-enzyme controls, and plotted as percentage of the mass of reducing sugar released per mass of polysaccharide substrate.

Referring to FIG. 5, *S. lividans* or *S. venezuelae* strains were created that contained integrated copies of single ActE cellulase genes SACTE_0236 (GH48 reducing-end cellobiohydrolase, G), SACTE_0237 (GH6 non-reducing end 1,4-beta cellobiohydrolase, H), SACTE_3159 (AA10 lytic polysaccharide monooxygenase PMO, I), SACTE_0482 (GH5 endoglucanase, J), or SACTE_3717(GH9 endoglucanase, K). (By "integrated," we mean that organisms contained a single copy of the gene inserted into the chromosome.) Addition of single genes gave a more active secretome than observed in WT or SET versions of *Streptomyces lividans*. Also, combination of approximately equal amounts of the five secretomes containing individual enzymes gave a synergistic increase in secretome activity over that obtained by individual enzymes (L. PMO/5/6/9/48) in digestion of PASC. This combination of enzymes, produced in industrial strain *Streptomyces lividans*, has 85% of the PASO conversion ability of the natural highly cellulolytic secretome produced by ActE, U).

Cassettes consisting of five ActE cellulase genes (cassette A), 5 Dpond-AA B6 genes (cassette B), a cross-species combination of 5 ActE cellulase genes plus the Dpond-AA B6 GH12 endoglucanase gene (cassette AB), or single species combination of 6 LaPpAH-95 genes (cassette 9) were also investigated. Expression of the entire gene cassette is under control of a single constitutive ermE* promoter (Siegl et al., 2013). Each gene in the cassette is preceded by an optimized ribosome-binding site (RBS). The cassettes were tested in *Streptomyces lividans* and *Streptomyces venezuelae*, two industrial *Streptomyces* strains that otherwise lack the ability to grow on cellulose.

The combination of cassette and industrial *Streptomyces* strain gave different results. All cassettes imparted the ability to degrade cellulose above that observed in the VVT and SET strains, demonstrating the ability to transfer a natural cellulolytic ability into an industrial strain. The cellulolytic activity of the secretome produced from the cassette was equivalent to that obtained by the more complicated process of expression of single proteins and remix into a multi-enzyme secretome. Moreover, the activity of the secretomes produced from the cassettes was comparable to the PASO conversion ability of the natural highly cellulolytic secretome produced by ActE.

The potential for other optimizations arising from combination of cassettes and *Streptomyces* strains is suggested by FIG. 5. For example, the A and AB cassettes gave strong activity when transformed into *Streptomyces venezuelae* (Q. and R.), but lesser (albeit considerably above background) activity when transformed into *Streptomyces lividans* (M. and N.). In contrast, cassettes B and 9 gave comparable, high activity in both industrial strains (compare O. and P. with S. and T.)

Example 2

Combinatorial Library

FIGS. 6-11 describe a set of experiments designed to explore a minimal combination of genes required for enhanced cellulolytic activity. A combinatorial library was formed and examined.

Cassette Design

Synthetic operons were designed to contain one gene copy for the enzyme classes GH6, LPMO, GH48, and GH5 and with either a GH9 or a GH12, or both. Synthetic operons contain ribosome binding sequences (RBS) preceding each gene (e.g., see (1) for de novo RBS prediction), a promoter sequence (e.g., the constitutive promoter ermE*p (2, 3)) preceding the first gene, and a terminator sequence following the last gene. Gene sequences may be optimized for codon usage (e.g., (4)).

A combinatorial library was designed using 16 highly-expressed cellulases from three cellulolytic isolates: *Streptomyces* sp. SirexAA-E (ActE), *Streptomyces* sp. DpondAA-B6 (B6), and *Streptomyces* sp. LaPpAH-95 (95). The set of ActE genes contains GH6, LPMO, GH48, GH5, and GH9 genes. The set of B6 genes contains GH6, LPMO, GH48, GH12, and GH9 genes. The set of 95 genes contains GH6, LPMO, GH48, GH5, GH9, and GH12 genes. Each gene sequence was synthesized de novo and assembled using Gibson assembly (5) to create a library with every possible combination of GH6-LPMO-GH48-GH5-GH9-GH12. In all, 324 (3×3×3×2×3×2) combinations are possible. Each member of the combinatorial library includes RBS sequences, the ermE*p promoter, and a terminator sequences as described above and is inserted into the cloning site of the pSET152 plasmid.

Combinatorial Library Construction

A DNA library containing each of the 324 synthetic operon combinations was prepared at an equimolar concentration. *Streptomyces lividans* 1326 protoplasts were prepared according to page 56 of (8) and transformed with the DNA library according to page 232 of (8). The spores from ~3,000 unique transformants were harvested and stored in 35% glycerol at −80° C. Spores were germinated at 30° C. with shaking for 4 hours in 2×YT medium (2×yeast extract/tryptone media, Kieser et al.), then centrifuged and resuspended in M63 minimal medium before being spread on M63 (minimal media, see Balows A. The Prokaryotes: A Handbook on the Biology of Bacteria. 2nd Ed, New York: Springer-VErlag: 1992) minimal agar containing 0.5, 1, 1.5, or 2% SigmaCell cellulose as the sole carbon source and 50 μg/mL apramycin. (SigmaCell cellulose is a purified highly crystalline form of cellulose that presents a formidable challenge as a growth substrate.) Exceptional strains were chosen based on larger colony size, pigmentation, and/or presence of spores, which were then cultured on IWL4 agar with 50 μg/mL apramycin and spores collected after 14 days to 35% glycerol at −80° C.

Secretome Activity Assay

A. Culture Growth Conditions

Fifty mL of 2YT media containing 50 μg/mL apramycin were inoculated from spore stocks and grown in 250 mL Erlenmeyer flasks containing springs to break up mycelial growth at 30° C. for 66 h.

B. Secretome Harvest

Cultures were transferred to 50 mL conical tubes and centrifuged at 4,000×g for 15 min at 4° C. in a swinging bucket rotor. Supernatants were vacuum filtered through 47 mm-diameter, 0.22-micron PES filters and were then concentrated using 10,000 MWCO PES-membrane spin concentrators (Sartorius Vivaspin Turbo 15) until each secretome was ~1.5 mL. The volume was readjusted to 15 mL using 10 mM MOPS pH 7, 50 mM NaCl, and the secretomes were reconcentrated to ~1.5 mL. Buffer exchange was repeated three times, ending with a final concentration of ~1.2 mL/secretome.

Figure 6:
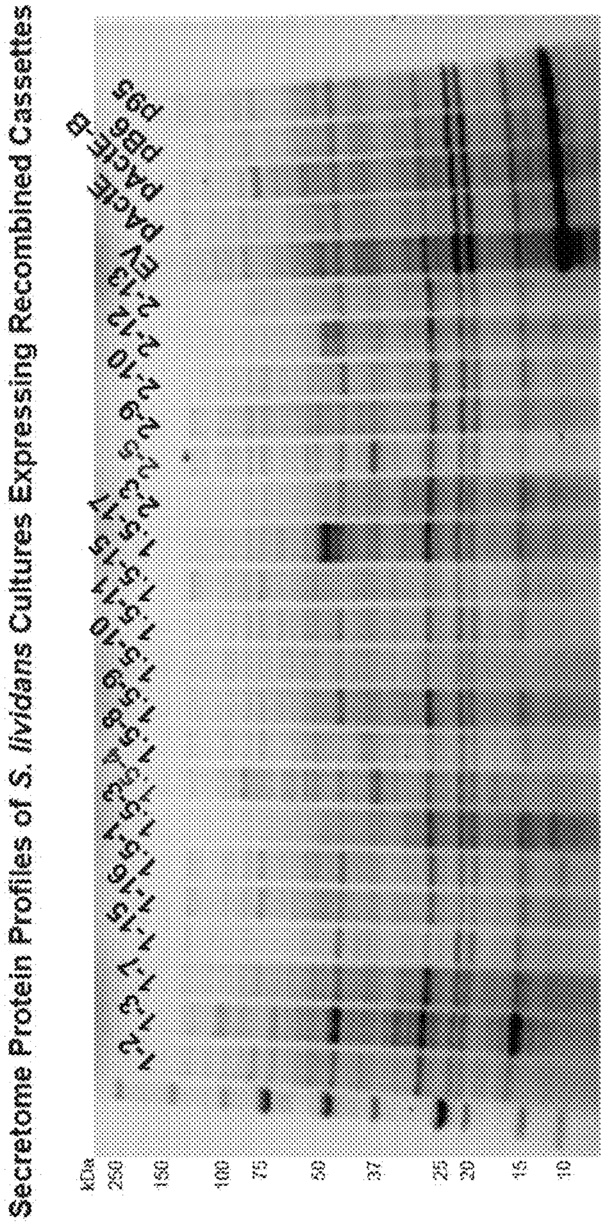
FIG. 6 is a SDS-PAGE of *S. lividans* secretomes harboring combinatorial or control cellulolytic operons. Red labels represent secretomes with the highest activity on cellulose.

C. Total Protein Analysis i SDS-PAGE: 8 μL of each secretome was loaded onto a 4-20% acrylamide SDS-PAGE gel after heating to 95° C. 2 min in the presence of SDS and β-mercaptoethanol. The gel was imaged using tryptophan fluorescence imaging (Bio-Rad GelDoc EZ imaging system with Stain-Free SGX Criterion gel; see FIG. 6). FIG. 6 is an SDS-PAGE of *S. lividans* secretomes harboring combinatorial or control cellulolytic operons. Red labels represent secretomes with the highest activity on cellulose.

ii BCA assay: Total protein in each secretome was measured using a standard bichinchonic acid (BCA) micro-assay (Thermo/Pierce) on 5-fold diluted secretomes in water with a bovine serum albumin standard curve.

iii Mass spectroscopy: Pellets from methanol (MeOH) precipitation of extracellular protein samples were resuspended and trypsin digested in urea, tris(2-carboxyethyl) phosphine (TCEP), chloroacetamide buffer overnight. Each sample was desalted and peptides separated over a 75 μm i.d. 30 cm long capillary with an imbedded electrospray emitter and packed with 1.7 μm C18 BEH stationary phase. Eluting peptides were analyzed with an Orbitrap Fusion Lumos in data dependent top 1 second mode. Raw files were analyzed using MaxQuant 1.5.2.8, searching for predicted fragments from the 16 cellulase sequences.

TABLE 2

Mass spectral counts of selected *S. lividans* secretomes containing combinatorial or control cellulolytic operons. DPondAA-B6 GH9 and GH12 were the predominant cellulases identified in secretomes with the highest activity.

| Protein IDs | Intensity 1.5_4 | Intensity 1.5_17 | Intensity 2_5 | Intensity pB6 | PSM 1.5_4 | PSM 1.5_17 | PSM 2_5 | PSM pB6 |
|---|---|---|---|---|---|---|---|---|
| A_GH5 | 2.E+08 | 6.E+06 | 3.E+06 | 1.E+06 | 6 | 0 | 0 | 0 |
| A_GH9 | 3.E+06 | 0.E+00 | 9.E+05 | 5.E+06 | 1 | 0 | 0 | 2 |
| B_GH12 | 2.E+10 | 5.E+08 | 1.E+10 | 1.E+10 | 42 | 9 | 88 | 73 |
| B_GH9 | 4.E+10 | 4.E+08 | 6.E+09 | 1.E+10 | 146 | 13 | 60 | 91 |

Filter Paper Screening

Spores from exceptional strains were added to 2×YT with 50 μg/mL apramycin and grown for 3 days at 30° C. with shaking. 200 μL of each culture was added to 5 mL of M63 media with a 1×10 cm Whatman paper strip as the sole carbon source. After growth at 30° C. with shaking, the filter paper strip from 20 exceptional strains broke within 7-13 days, which compares to >30 days for VVT *S. lividans* or *S. lividans* transformed with pSET152 empty vector.

D. Activity Assay

The dinitrosalicylic acid (DNS) assay (7) was performed in duplicate for each secretome by reacting them with 500 μg of neutralized, phosphoric acid swollen cellulose (PASO; amorphous cellulose, FIG. 7), 500 μg of filter paper (FP; crystalline cellulose, FIG. 8), or 500 μg of lichenan (β-1,4- and β-1,3-linked glucan, FIG. 9) in thin-walled strip tubes with 50 μL reaction volume. Each tube contained 20 μL of secretome protein, 25 μL of 20 mg/mL substrate solution (prepared in water with 0.05% sodium azide, and 5 μL of 10 mM MES, pH 6. Secretome- and substrate-alone samples were included as controls. Tubes were incubated at 42° C. for 21 h for PASO and filter paper reactions, 4.5 h for lichenan reactions).

Tubes were centrifuged at 2500×g for 5 min and 30 μl of the supernatant was transferred to thin-walled PCR plates, combined with 60 μL of DNS reagent (3,5-dinitrosalicylic acid), and heated to 95° C. for 5 min. Glucose stock solutions at concentrations ranging from 0.5 to 1.5 mg/mL were included in the plate for generating a reducing sugar standard curve. 25 μL of the reactions or standards were combined with 125 μL of water in a U-bottom polystyrene 96-well plate and the absorbance was measured at 540 nm. Absorbance intensity is directly proportional to the amount of reducing sugar present and is proportional to cellulase activity. Activity was determined as the percentage of reducing sugar generated from 500 μg of polysaccharide substrate. Values were normalized to the activity present in 10 μg of total protein. The in vivo strain activity in the filter paper assay (described in Section 3) was compared to the in vitro secretome activity on PASO in FIG. 10.

E. Results of Activity Assay

Figure 7:
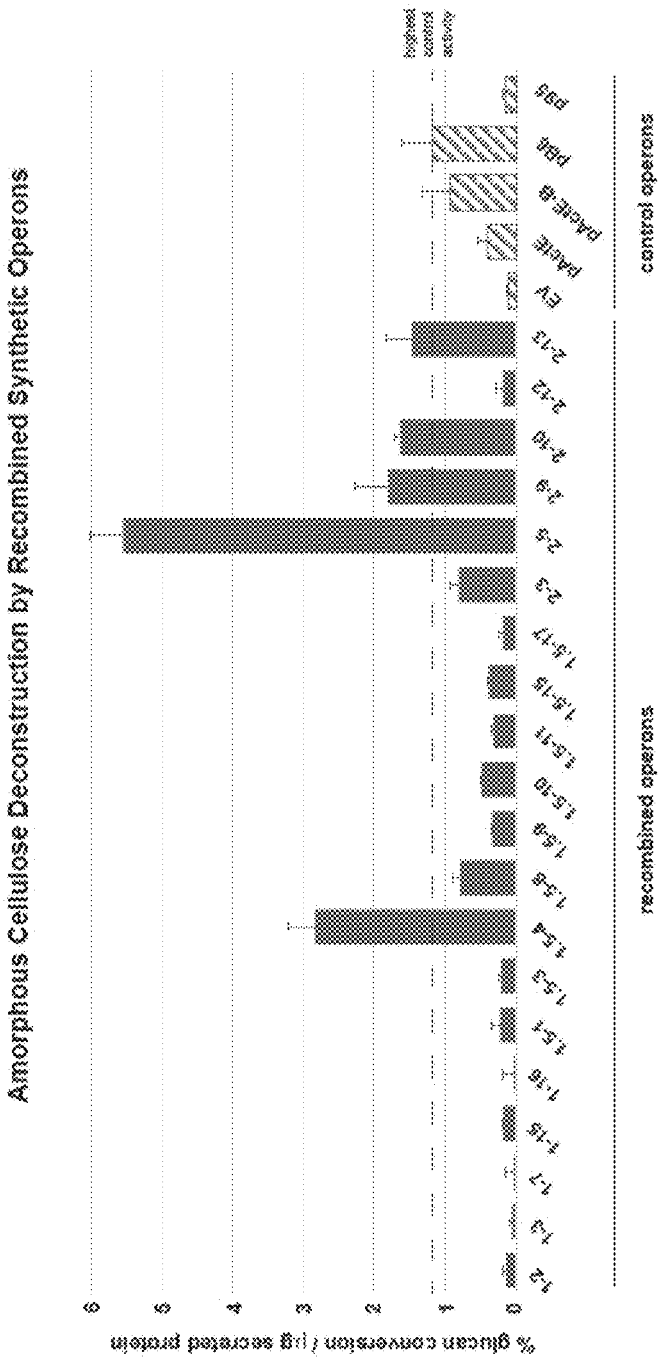
FIG. 7 is a diagram of the activity of secretomes from *S. lividans* harboring combinatorial or control cellulolytic operons on amorphous cellulose (PASO). EV is an empty vector control containing pSET190 plasmid without cellulase genes. pACTE contains 5 ActE cellulase genes, pActE-B contains 5 ActE cellulases plus the B6 GH12 cellulase, pB6 contains 5 DpondAA-B6 cellulases, and p95 contains 6 LaPpAH-95 cellulases.

Results of the activity assay are disclosed in FIGS. 7-11. FIG. 7 is a diagram of the activity of secretomes from *S. lividans* harboring combinatorial or control cellulolytic operons on amorphous cellulose (PASO). EV is an empty vector control containing pSET152 plasmid without cellulase genes. pACTE contains 5 ActE cellulase genes, pActE-B contains 5 ActE cellulases plus the B6 GH12 cellulase, pB6 contains 5 DpondAA-B6 cellulases, and p95 contains 6 LaPpAH-95 cellulases. From these results, we learned that at least two strains exhibited cellulase activity at least two fold higher on PASO than the best performing, non-combinatorial control operon, pB6.

Figure 8:
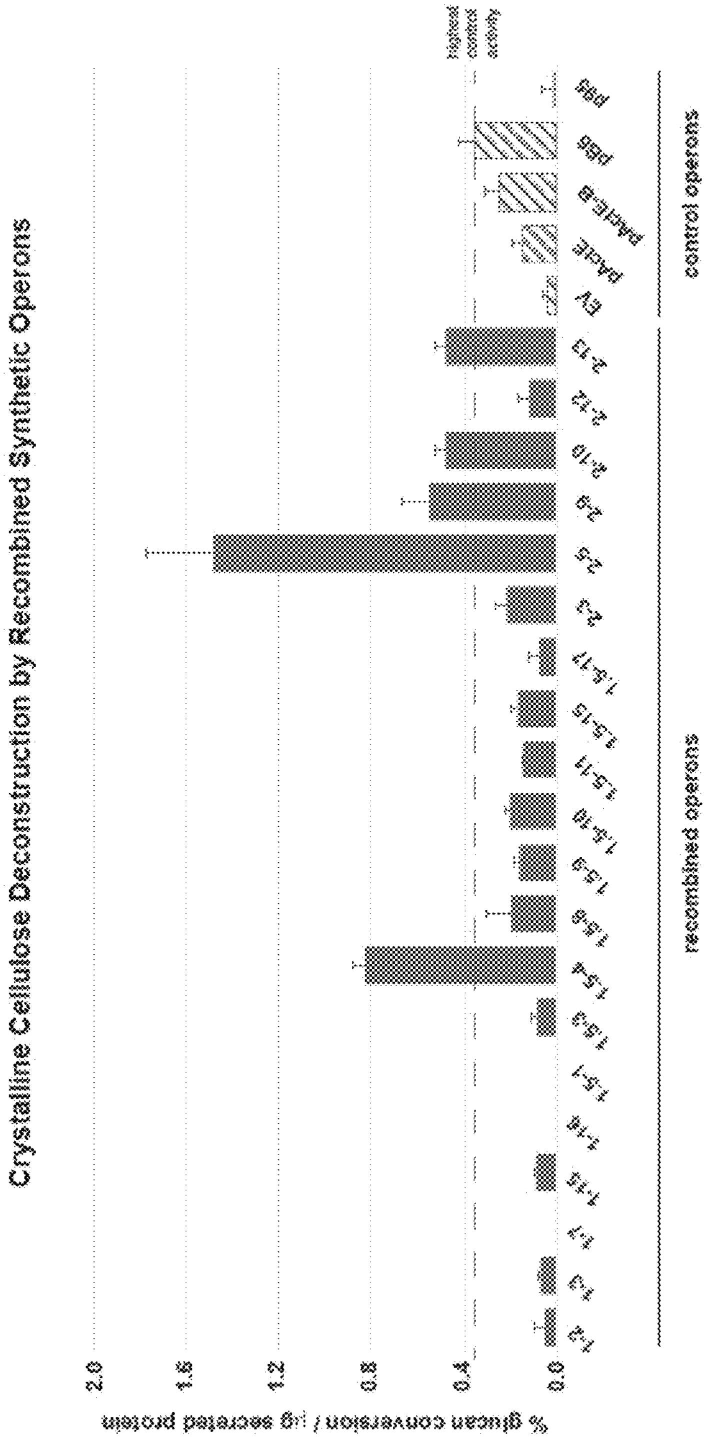
FIG. 8 discloses the activity of secretomes from *S. lividans* harboring combinatorial or control cellulolytic operons on crystalline cellulose (filter paper). Samples are as described in FIG. 7.

FIG. 8 discloses the activity of secretomes from *S. lividans* harboring combinatorial or control cellulolytic operons on crystalline cellulose (filter paper). Samples are as described in FIG. 7. From these results, two strains exhibited cellulase activity at least two-fold higher on filter paper than the best performing, non-recombined control operon, pB6.

Figure 9:
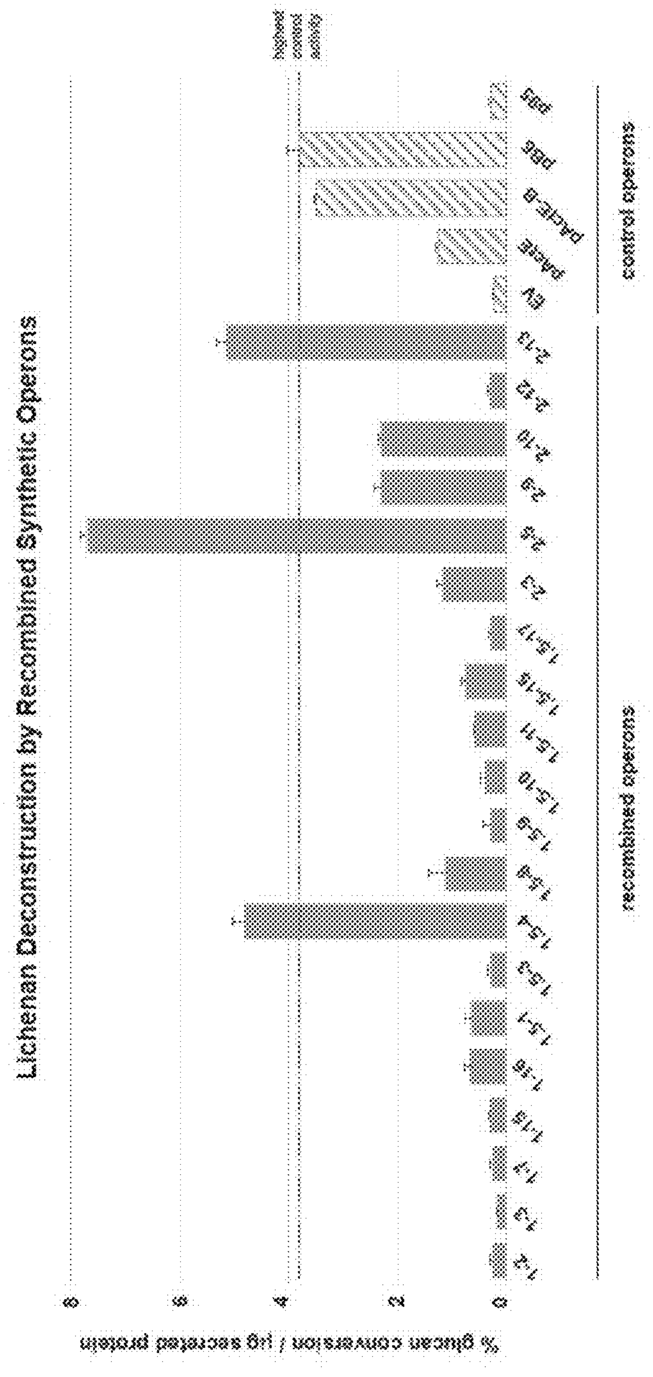
FIG. 9 discloses the activity of secretomes from *S. lividans* harboring combinatorial or control cellulolytic operons on lichenan. Samples are as described in FIG. 7.

Similarly, FIG. 9 discloses the activity of secretomes from *S. lividans* harboring combinatorial or control cellulolytic operons on lichenan, another cellulose source. Samples are as described in FIG. 7. From these results, three strains exhibited glucanase activity significantly higher on lichenan (a polysaccharide consisting of alternating beta-1,3-glucan and beta-1,4-glucan linkages) than the best performing, non-recombined control operon, pB6.

Figure 10:
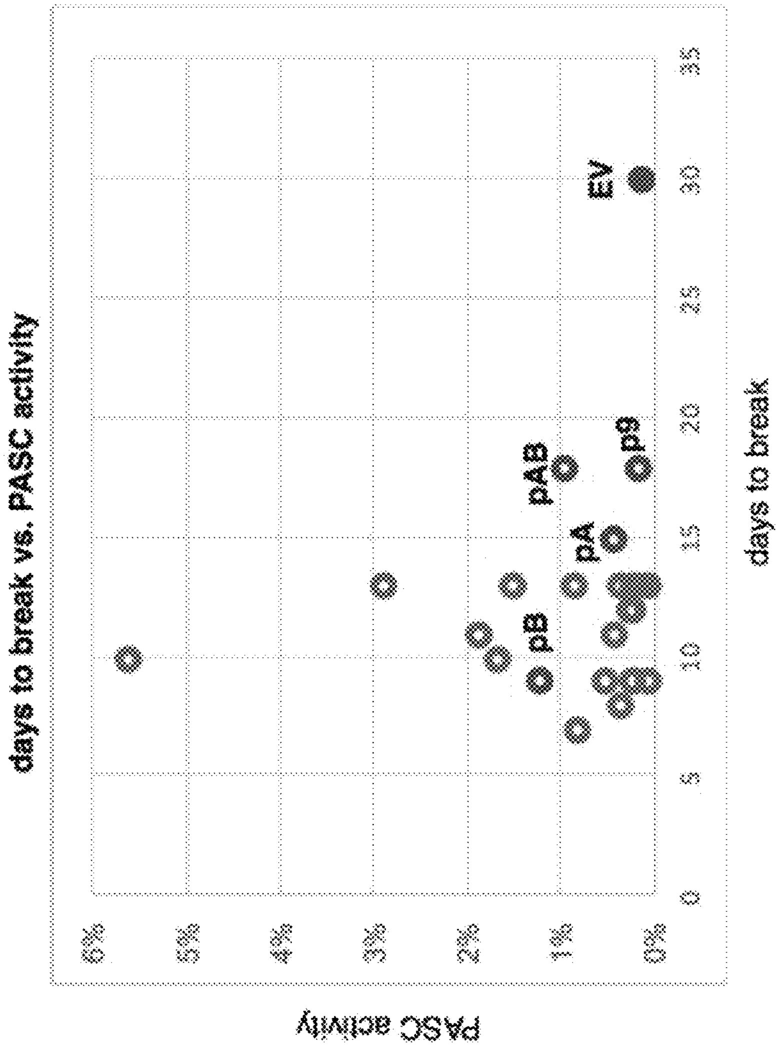
FIG. 10 is a plot of the correlation between the days required for strains to break filter paper in vivo and in vitro cellulase activity of secretomes of *S. lividans* containing combinatorial (blue) or control cellulolytic operons (red).

FIG. 10 is a plot of the correlation between the days required for strains to break filter paper in vivo and in vitro cellulase activity of secretomes of *S. lividans* containing combinatorial (blue) or control cellulolytic operons (red). This figure is correlating the in vivo activity of the strain using filter paper as a sole carbon source with the in vitro activity of the actual secreted protein on cellulose. The latter result is a direct measure of the secreted products of the cassette plus other secreted *lividans* proteins. This correlation is of interest as it shows the relationship between strain metabolic activity and actual secreted protein and can help indicate the best route toward commercial success of the invention. One application of the modified strains could be to use the living engineered strain for biomass digestion and another application could be to harvest the secreted proteins generated from the strain.

5. Genomic Data

Spores from 10 exceptional strains were added to 5 mL of SGGP (0.4% tryptone, 0.4% yeast extract, 0.05% $MgSO_4$, 1% glucose. 0.2% glycine, 0.01 M potassium phosphate buffer, pH 7.0) medium with 50 μg/mL apramycin, and genomic DNA was purified according to page 162 of (8). DNA samples were submitted to the University of Wisconsin Biotechnology Center for library preparation and sequencing. Sequencing was performed via Illumina MiSeq with a paired-end 220-bp read length. Both raw reads and Bowtie 2 (9) assemblies were examined for matches to genes from the combinatorial library.

FIG. 11 is a diagram disclosing the presence of genes assigned from direct Illumina sequencing of *S. lividans* harboring combinatorial cellulolytic operons. The combination of GH9 from 95 and GH12 from B6 (isolate 2-5) is a preferred combination because of the increased cellulolytic activity of this isolate. Combinations of GH9 (from B6), GH12 (from B6), and GH5 (from ActE) are also preferred.

Figure 12:
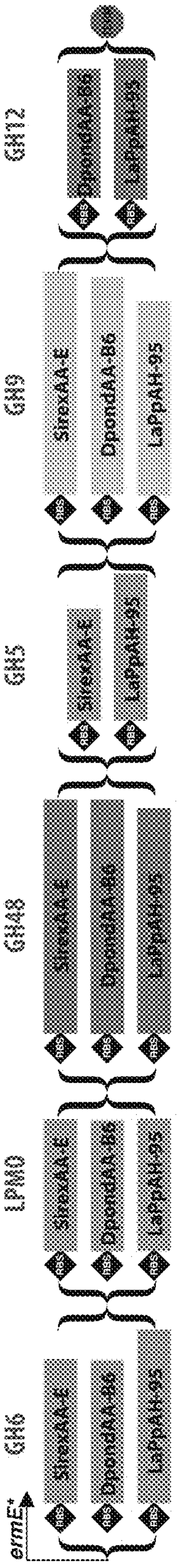
FIG. 12 is a diagram of combinatorial gene operons produced for Example 2.

FIG. 12 is a diagram containing examples of combinatorial gene operons produced for the Example 2 experiments. Each strain may contain a GH6, LPMO, GH48, GH5, GH9, and GH12 derived from any of the three host cellulolytic *Streptomyces* strains as depicted. Optimal cellulolytic operon combinations are selected by the engineered strain's ability to break filter paper faster than wild-type host strains and/or strains expressing the non-combinatorial operons described in FIG. 3.

REFERENCES

1. Book A J, Lewin G R, McDonald B R, Takasuka T E, Doering D T, Adams A S, Blodgett J A V, Clardy J, Raffa K F, Fox B G, et al (2014) Cellulolytic *Streptomyces* strains associated with herbivorous insects share a phylogenetically linked capacity to degrade lignocellulose. Appl Environ Microbiol 80:4692-4701
2. Cambray G, Guimaraes J C, Mutalik V K, Lam C, Mai Q-A, Thimmaiah T, Carothers J M, Arkin A P, Endy D (2013) Measurement and modeling of intrinsic transcription terminators. Nucleic Acids Res 41:5139-5148
3. Espah Borujeni A, Channarasappa A S, Salis H M (2014) Translation rate is controlled by coupled trade-offs between site accessibility, selective RNA unfolding and sliding at upstream standby sites. Nucleic Acids Res 42:2646-2659
4. Miller G L (1959) Use of dinitrosalicylic acid reagent for determination of reducing sugar. Analytical Chemistry 31:426-428
5. Siegl T, Tokovenko B, Myronovskyi M, Luzhetskyy A (2013) Design, construction and characterisation of a synthetic promoter library for fine-tuned gene expression in actinomycetes. Metab Eng 19:98-106
6. Takasuka T E, Book A J, Lewin G R, Currie C R, Fox B G (2013) Aerobic deconstruction of cellulosic biomass by an insect-associated *Streptomyces*. Sci Rep 3:1030

References for Example 2

1. Tian T, Salis H M (2015) A predictive biophysical model of translational coupling to coordinate and control protein expression in bacterial operons. *Nucleic Acids Research* 43:7137-7151. Available at: https://academic.oup.com/nar/article-lookup/doi/10.1093/nar/gkv635.
2. Bibb M J, Janssen G R, Ward J M (1986) Cloning and analysis of the promoter region of the erythromycin-resistance gene (ermE) of *Streptomyces erythraeus*. *Gene*

41:E357. Available at: http://linkinghub.elsevier.com/retrieve/pii/0378111986901228.
3. Schmitt-John T, Engels J W (1992) Promoter constructions for efficient secretion expression in *Streptomyces lividans*. *Applied Microbiology and Biotechnology* 36:493-498. Available at: http://link.springer.com/article/10.1007/BF00170190.
4. Richardson S M, Liu S, Boeke J D, Bader J S (2012) Design-A-Gene with GeneDesign. *Methods in Molecular Biology* 852:235-247. Available at: http://eutils.ncbi.nlm.nih.gov/entrez/eutils/elink.fcgi?dbfrom=pubmed&id=22328438&retmode=ref&cmd=prlinks.
5. Gibson D G et al. (2009) Enzymatic assembly of DNA molecules up to several hundred kilobases. Nature methods 6:343-345. Available at: http://www.nature.com/doifinder/10.1038/nmeth.1318.
6. Khadempour L, Burnum-Johnson K E, Baker E S, Nicora C D, Webb-Roberston B J M, White R A III, Monroe M E, Huang E L, Smith R D, Currie C R (2016) The fungal cultivar of leaf-cutter ants produces specific enzymes in response to different plant substrates. Mol. Ecol. 25:5795-5805.
7. Takasuka T E, Walker J A, Bergeman L F, Vander Meulen K A, Makino S, Elsen N L, Fox B G. (2014) Cell-free translation of biofuel enzymes. Methods Mol. Biol. 1118: 71-95.
8. Kieser T, Bibb M J, Buttner M J, Chater K F, Hopwood D A (2000) Practical *Streptomyces* Genetics. 613. Available at: http://books.google.com/books?id=0Hh2QgAACAAJ&dq=intitle:practical+streptomyces+genetics&hl=&cd=1&source=gbs_api.
9. Langmead B, Salzberg S L (2012) Fast gapped-read alignment with Bowtie 2. Nature methods 9:357-359. Available at: http://eutils.ncbi.nlm.nih.gov/entrez/eutils/elink.fcgi?dbfrom=pubmed&id=22388286&retmode=ref&cmd=prlinks.

We claim:

1. A heterologous gene cassette for expression in a *Streptomyces* species to enhance growth on a cellulosic polysaccharide substrate, the cassette comprising a glycoside hydrolase family 9 (GH9) endoglucanase gene from *Streptomyces* LaPpAH-95, a glycoside hydrolase family 12 (GH12) endoglucanase gene from *Streptomyces* DpondAA-B6, and at least two four genes selected from the group consisting of:

a) a glycoside hydrolase family 6 (GH6) gene, b) an auxiliary activity family 10 (AA10) gene, c) a glycoside hydrolase family 48 (GH48) gene, and d) a glycoside hydrolase family 5 (GH5) gene.

2. The cassette of claim 1, wherein the genes are under the control of a single constitutive promoter.

3. The cassette of claim 1, wherein the genes have been modified to substantially optimize enzyme expression compared to the wild-type sequences.

4. A *Streptomyces* strain recombinantly engineered with the cassette of claim 1.

5. The strain of claim 4, wherein the *Streptomyces* is selected from the group of *S. lividans* or *S. venezuelae.*

6. A method of digesting a cellulosic polysaccharide comprising the step of exposing a cellulosic polysaccharide substrate to the strain of claim 4 or its secreted products.

7. The method of claim 6 wherein the polysaccharide substrate is selected from the group consisting of miscanthus, switchgrass, hemp, corn, poplar, willow, paper, wood waste, corn stover, prickly pear cactus cladodes, kelp, sorghum, straw, eucalyptus, pine, sugarcane bagasse, cotton, bamboo, nut shells, bark, sawdust, wood chips, and paper mill waste.

8. The cassette of claim 1, wherein the cassette comprises the GH6 gene, the AA10 gene, the GH48 gene, the GH5 gene, the GH9 gene, and the GH12 gene under the control of a single constitutive promoter and each separated by a ribosomal binding site.

9. The cassette of claim 8, wherein the GH6 gene, the AA10 gene, the GH48 gene, the GH5 gene, and the GH12 gene are from *Streptomyces* DpondAA-E36.

10. The cassette of claim 8, wherein the GH6 gene, the AA10 gene, the GH48 gene, the GH5 gene, and the GH9 gene, are from *Streptomyces* LaPpAh-95.

11. The cassette of claim 8, wherein the GH6 gene, the AA10 gene, the GH48 gene, and the GH5 gene, are from *Streptomyces* sp SirexAA-E.

12. The method of claim 6, wherein the cellulosic polysaccharide substrate is selected from the group of cellulose and hemicelluloses.

13. The method of claim 6, wherein the cellulosic polysaccharide substrate is selected from the group of wood and non-wood biomass.

14. The method of claim 6, wherein the cellulosic polysaccharide substrate is a lignocellulosic material.

15. A heterologous gene cassette for expression in a *Streptomyces* species to enhance growth on a cellulosic polysaccharide substrate, the cassette comprising a GH9 endoglucanase gene from *Streptomyces* LaPpAH-95 and at least three genes selected from the group consisting of:

a) a glycoside hydrolase family 6 (GH6) gene, b) an auxiliary activity family 10 (AA10) gene, c) a glycoside hydrolase family 48 (GH48) gene, d) a glycoside hydrolase family 5 (GH5) gene, and e) a glycoside hydrolase family 12 (GH12) gene.

16. The cassette of claim 15, wherein the cassette comprises the GH6 gene, the AA10 gene, the GH48 gene, the GH5 gene, and the GH9 gene under the control of a single constitutive promoter and each separated by a ribosomal binding site.

17. The cassette of claim 16, wherein the cassette additionally comprises the GH12 gene.

18. The cassette of claim 16, wherein the GH6 gene, the AA10 gene, the GH48 gene, and the GH5 gene are from *Streptomyces* sp SirexAA-E.

19. The cassette of claim 16, wherein the GH6 gene, the AA10 gene, the GH48 gene, and the GH5 gene are from *Streptomyces* DpondAA-86.

20. A heterologous gene cassette for expression in a *Streptomyces* species to enhance growth on a cellulosic polysaccharide substrate, the cassette under the control of a single constitutive promoter and comprising a GH6 gene, a AA10 gene, a GH48 gene, a GH9 gene, and a GH12 gene each from *Streptomyces* LaPpAH-95 and each separated by a ribosomal binding site.

* * * * *

UNITED STATES PATENT AND TRADEMARK OFFICE

CERTIFICATE OF CORRECTION

PATENT NO. : 10,428,334 B2
APPLICATION NO. : 15/478871
DATED : October 1, 2019
INVENTOR(S) : Brian Grant Fox et al.

It is certified that error appears in the above-identified patent and that said Letters Patent is hereby corrected as shown below:

In the Specification

Column 3, Line 23, "(PASO)" should be --(PASC)--.

Column 4, Line 42, "(PASO)" should be --(PASC)--.

Column 10, Line 20, "(PASO)" should be --(PASC)--.

Column 10, Line 36, "VVT" should be --WT--.

Column 10, Line 43, "(PASO)" should be --(PASC)--.

Column 11, Line 66, "VVT" should be --WT--.

Column 11, Line 62, "(PASO)" should be --(PASC)--.

Column 13, Line 4, "(PASO)" should be --(PASC)--.

Column 13, Line 22, "(PASO)" should be --(PASC)--.

Column 13, Line 27, "(PASO)" should be --(PASC)--.

Column 13, Line 34, "(PASO)" should be --(PASC)--.

In the Claims

Column 97, Claim 1, Line 65, "two four genes" should be --two genes--.

Signed and Sealed this
Third Day of December, 2019

Andrei Iancu
*Director of the United States Patent and Trademark Office*

Column 99, Claim 9, Line 21, "E36" should be --B6--.

Column 100, Claim 19, Line 25, "86" should be --B6--.

SEQUENCE LISTING

```
<160> NUMBER OF SEQ ID NOS: 35

<210> SEQ ID NO 1
<211> LENGTH: 600
<212> TYPE: PRT
<213> ORGANISM: Streptomyces LaPpAH-95

<400> SEQUENCE: 1

Met Leu His Pro Leu Arg Thr Phe Arg Arg Ala Ala Arg Thr Val Ala
1               5                   10                  15

Val Ala Thr Ala Ala Leu Leu Leu Pro Leu Ala Gly Ala His Pro Ala
            20                  25                  30

Ser Ala Asp Ala Ala Arg Ala Ala Ala Ala Gly Ser Gly Tyr Trp His
        35                  40                  45

Thr Ser Gly Arg Gln Ile Leu Asp Ala Ala Asn Gln Pro Val Arg Ile
    50                  55                  60

Ala Gly Ile Asn Trp Phe Gly Phe Glu Thr Ala Asn Tyr Val Pro His
65                  70                  75                  80

Gly Leu Trp Ser Arg Asp Tyr Lys Ser Met Ile Asp Gln Met Arg Ser
                85                  90                  95

Leu Gly Tyr Asn Thr Ile Arg Leu Pro Tyr Ser Asp Asp Ile Phe Ala
            100                 105                 110

Gly Thr Glu Pro Ala Ser Ile Asn Tyr Ser Ala Gly Met Asn Thr Asp
        115                 120                 125

Leu Ala Gly Leu Asn Ser Leu Gln Val Met Asp Arg Ile Val Asp His
    130                 135                 140

Ala Gly Ser Phe Gly Met Lys Val Ile Leu Asp Arg His Arg Pro Asp
145                 150                 155                 160

Ser Ala Gly Gln Ser Ala Leu Trp Tyr Thr Ser Ala Val Pro Glu Ser
                165                 170                 175

Thr Trp Leu Ala His Leu Lys Ser Leu Ala Ala Arg Tyr Ala Gly Asn
            180                 185                 190

Asp Ala Val Val Gly Ile Asp Leu His Asn Glu Pro His Asp Pro Ala
        195                 200                 205

Cys Trp Gly Cys Gly Asp Thr Thr Lys Asp Trp Arg Leu Ala Ala Gln
    210                 215                 220

Arg Gly Gly Asn Ala Ala Leu Ser Ala Asn Pro Asp Leu Leu Ile Phe
225                 230                 235                 240

Val Glu Gly Val Gln Thr Val Asp Gly Val Ser Gly Trp Trp Gly Gly
```

-continued

```
                245                 250                 255

Asn Leu Met Gly Val Gly Gln Tyr Pro Val Glu Leu Ser Val Pro His
            260                 265                 270

Lys Val Val Tyr Ser Ala His Asp Tyr Ala Thr Ser Val Ala Gln Gln
        275                 280                 285

Pro Trp Phe Thr Asp Ser Ser Phe Pro Asp Asn Met Pro Gly Val Trp
    290                 295                 300

Asp Lys Tyr Trp Gly Tyr Ile Phe Lys Gln Asn Ile Ala Pro Val Trp
305                 310                 315                 320

Val Gly Glu Phe Gly Thr Thr Leu Gln Ser Thr Thr Asp Gln Lys Trp
                325                 330                 335

Leu Lys Ala Leu Ala Asp Tyr Leu Arg Pro Thr Ser Gln Tyr Gly Ala
            340                 345                 350

Asp Ser Phe Ser Trp Thr Phe Trp Ser Trp Asn Pro Asn Ser Gly Asp
        355                 360                 365

Thr Gly Gly Ile Leu Lys Asp Asp Trp Thr Ser Val Asp Thr Val Lys
    370                 375                 380

Asp Gly Tyr Leu Ala Ser Ile Lys Ala Pro Asp Phe Gly Asn Gly Gly
385                 390                 395                 400

Gly Ser Gly Gly Asp Asp Asp Thr Gln Ala Pro Thr Ala Pro Thr Gly
                405                 410                 415

Leu Ala Val Thr Gly Thr Thr Gly Thr Ser Val Ser Leu Ser Trp Lys
            420                 425                 430

Ala Ala Ser Asp Asp Thr Gly Val Thr Ala Tyr Asp Val Tyr Arg Gly
        435                 440                 445

Ser Thr Lys Ala Gly Thr Ala Thr Gly Thr Thr Phe Thr Asp Thr Gly
    450                 455                 460

Val Thr Ser Gly Thr Ser Tyr Thr Tyr Thr Val Arg Ala Arg Asp Ala
465                 470                 475                 480

Ala Gly Asn Thr Ser Ala Pro Ser Ala Ser Val Thr Ala Thr Thr Thr
                485                 490                 495

Gly Ser Gly Gly Asn Thr Gly Cys Lys Ala Val Tyr Thr Val Asn Gly
            500                 505                 510

Asp Trp Gly Ser Gly Phe Gly Val Asp Ile Thr Val Thr Asn Thr Gly
        515                 520                 525

Thr Ala Pro Ala Thr Ser Trp Lys Leu Thr Trp Thr Tyr Gly Gly Ser
    530                 535                 540

Gln Lys Ile Thr Asn Met Trp Asn Ala Ser Tyr Thr Gln Ser Gly Ala
545                 550                 555                 560

Ser Val Thr Val Thr Ser Thr Asp Tyr Asn Gly Gly Leu Ala Ala Gly
                565                 570                 575

Ala His Thr Gly Phe Gly Phe Gln Gly Thr Pro Ala Ala Gly Ala Val
            580                 585                 590

Pro Thr Val Ser Cys Thr Leu Ser
        595                 600
```

<210> SEQ ID NO 2
<211> LENGTH: 1761
<212> TYPE: DNA
<213> ORGANISM: Streptomyces sp SirexAA-E

<400> SEQUENCE: 2

```
atgagtcgta cgtcccgcac cacactgcgt cgcagtcgga cggcgctgat ggcagcaggt      60

gcactcgtcg cggcagccgc agggagcgca gcagcagccg ctccgttcgg agcaacggca     120
```

-continued

```
gcggccgcag caggatgcac ggtcgactat aagatccaga accagtggaa tggcggtctg    180
acagcatcag tctccgtgac aaacaacggg gacgccatct caggttggca gctgcagtgg    240
agcttcgcag gcggagagca ggtcagccag ggttggaatg ccacagtatc ccagagcgga    300
tcggcagtca cggccaagga cgcaggttat aacgcagcgc tcgccaccgg agcctcggcc    360
agcttcggtt tcaatgcaac gggcaatgga aacagcgtcg ttccggcaac cttcaagttg    420
aatggtgtaa cctgcaacgg gggtacgaca ggaccgacgg acccgacaga cccgaccgac    480
cccaccgacc cgacagaccc cccggcaggt aatcgagtgg acaaccctta ccagggagca    540
aaggtttatg tcaacccgga atggtccgcc aacgccgcag ccgaacccgg cggtgaccgc    600
atagcggacc agccgacagg tgtctggttg gatcgtatag cggccatcga gggggccaat    660
ggaagtatgg gccttcgcga ccacctggac gaagcgttga cgcaaaaagg aagcggagag    720
ctggtggtcc aagtggtcat ctacaatctc ccaggtcgtg actgtgccgc actggcctcg    780
aacggagaac tcgggccgac cgagatcgga cgctacaaaa cagaatatat cgatccgata    840
gcggagatcc tgggtgaccc gaagtacgca gggctccgga tcgtgacgac ggtagaaatc    900
gatagtctgc cgaatttggt cactaatgcc ggaggacgtc caacggcaac accggcgtgc    960
gacgtcatga aagccaacgg taattatgtg aagggtgtcg gatatgcact gaacaagctc   1020
ggggatgcgc cgaatgtgta caattatatc gacgcaggcc atcacggatg gatcggatgg   1080
gatgacaact tcggcgcctc tgcagagatc ttccacgaag cggccaccgc agagggggca   1140
acggtcaacg acgtccatgg tttcatcacc aacacagcga actactcagc gctgaaggaa   1200
gagaacttct cgatcgatga tgcagtaaac ggcaccagcg tccgccagtc taagtgggtg   1260
gactggaatc gatacacaga cgagctcagc ttcgcccagg cattccgcaa tgaactcgtg   1320
agtgtgggtt tcaactccgg tatcggaatg ctgattgaca cgtcgcggaa cggttggggc   1380
ggagcaaatc gtccgtcggg cccgggtgcc aatacatccg tcgacacgta tgtagacgga   1440
ggccgctacg atcgacggat ccatctcggt aactggtgta atcaggcagg tgcgggactc   1500
ggtgaacgcc cgcaggctgc gccagaaccg ggcatcgacg cctacgtgtg gatgaagccc   1560
ccgggagaga gtgacggatc cagctccgaa attccgaacg atgagggcaa gggattcgac   1620
cgtatgtgcg acccgacata cacgggcaac gcacggaata acaacaatat gagtggcgcg   1680
ctgggaggtg cccccgtctc gggaaagtgg ttcagtgccc aattccaaga gctgatgaaa   1740
aatgcgtatc cggcattgtg a                                              1761
```

```
<210> SEQ ID NO 3
<211> LENGTH: 710
<212> TYPE: PRT
<213> ORGANISM: Streptomyces LaPpAH-95

<400> SEQUENCE: 3

Met Ser Thr Arg Gly Thr Ile Lys Gln Gly Leu Arg Arg Arg Leu Ala
1               5                   10                  15

Ala Ala Ser Ala Leu Ala Met Gly Ala Ala Leu Ala Val Ala Ile Pro
            20                  25                  30

Thr Thr Ala Asp Ala Ala Ala Ala Arg Val Asp Asn Pro Tyr Val Gly
        35                  40                  45

Ala Lys Ala Tyr Val Asn Pro Asp Trp Ser Ala Lys Ala Ala Ala Glu
    50                  55                  60

Pro Gly Gly Ala Ala Ile Ala Asp Thr Pro Ala Phe Val Trp Met Asp
65                  70                  75                  80
```

-continued

```
Arg Ile Ala Ala Ile Gly Gly Thr Pro Gly Ala Met Ser Leu Arg Glu
                85                  90                  95

His Leu Asp Thr Ala Leu Asp Gln Gly Ala Asn Leu Phe Gln Val Val
            100                 105                 110

Ile Tyr Asp Leu Pro Gly Arg Asp Cys Ala Ala Leu Ala Ser Asn Gly
        115                 120                 125

Glu Leu Gly Pro Thr Glu Leu Asp Arg Tyr Lys Ser Glu Tyr Ile Asp
    130                 135                 140

Pro Ile Ser Glu Ile Leu Ala Asp Pro Ala Tyr Ala Asn Leu Arg Ile
145                 150                 155                 160

Val Thr Ile Ile Glu Pro Asp Ser Leu Pro Asn Ile Val Thr Asn Ala
                165                 170                 175

Gly Gly Thr Ala Gly Ser Thr Asp Ala Cys Ala Thr Met Lys Ala Asn
            180                 185                 190

Gly Asn Tyr Glu Lys Gly Val Gly Tyr Ala Leu His Thr Leu Gly Ala
        195                 200                 205

Ile Pro Asn Val Tyr Asn Tyr Val Asp Ala Ala His His Gly Trp Leu
    210                 215                 220

Gly Trp Asp Ser Asn Met Val Pro Ala Gly Val Glu Phe Lys Lys Ala
225                 230                 235                 240

Ala Thr Ser Glu Gly Ala Thr Val Asp Asp Val Ala Gly Phe Ile Val
                245                 250                 255

Asn Thr Ala Asn Tyr Ser Ala Leu Lys Glu Pro Asn Phe Lys Ile Thr
            260                 265                 270

Asp Ser Val Asn Gly Thr Thr Val Arg Gln Ser Lys Trp Val Asp Trp
        275                 280                 285

Asn Tyr Tyr Thr Asp Glu Leu Ser Phe Ala Gln Ala Leu Arg Thr Gln
    290                 295                 300

Leu Val Gly Gln Gly Phe Asn Ser Asn Ile Gly Met Leu Ile Asp Thr
305                 310                 315                 320

Ala Arg Asn Gly Trp Gly Gly Ser Asp Arg Pro Thr Ser Ala Gly Pro
                325                 330                 335

Leu Thr Ser Val Asp Asp Tyr Val Asn Gly Gly Arg Val Asp Arg Arg
            340                 345                 350

Ile His Ala Gly Asn Trp Cys Asn Gln Ser Gly Ala Gly Ile Gly Glu
        355                 360                 365

Arg Pro Thr Ser Ala Pro Glu Ala Gly Ile Asp Ala Tyr Val Trp Ala
    370                 375                 380

Lys Pro Pro Gly Glu Ser Asp Gly Ser Ser Gln Ala Glu Asp Asn Asp
385                 390                 395                 400

Glu Gly Lys Gly Phe Asp Arg Met Cys Asp Pro Thr Tyr Glu Gly Asn
                405                 410                 415

Gly Arg Asn Gly Asn Ser Lys Thr Gly Ala Leu Pro Asn Ser Pro Val
            420                 425                 430

Ala Gly His Trp Phe Ser Ala Gln Phe Gln Glu Leu Val Arg Asn Ala
        435                 440                 445

Tyr Pro Pro Ile Asp Gly Ser Gly Glu Asn Pro Gly Gly Gly Gly Asp
    450                 455                 460

Asp Asp Thr Gln Ala Pro Thr Ala Pro Thr Gly Leu Thr Ser Ser Ala
465                 470                 475                 480

Lys Thr Ser Ser Ser Val Ser Leu Ser Trp Thr Ala Ser Ser Asp Asn
                485                 490                 495
```

-continued

```
Lys Ala Val Thr Gly Tyr Asp Val Tyr Arg Gly Gly Thr Lys Val Gly
            500                 505                 510

Ser Thr Thr Thr Thr Ser Tyr Thr Asp Thr Gly Leu Ser Ala Ser Thr
        515                 520                 525

Ala Tyr Ser Tyr Thr Val Lys Ala Lys Asp Ala Ala Gly Asn Val Ser
    530                 535                 540

Ala Ala Ser Ser Ala Leu Ser Val Thr Thr Ser Ala Gly Gly Gly Thr
545                 550                 555                 560

Gly Thr Gly Ser Leu Lys Val Gln Tyr Lys Asn Asn Asp Asn Ser Pro
                565                 570                 575

Thr Asp Asn Gln Ile Arg Phe Gly Leu Gln Leu Val Asn Thr Gly Ser
            580                 585                 590

Ser Ala Val Asp Leu Ser Thr Val Lys Leu Arg Tyr Trp Phe Thr Pro
        595                 600                 605

Glu Ser Gly Ser Ser Thr Phe Gly Thr Ala Cys Asp Tyr Ala Val Leu
    610                 615                 620

Gly Cys Gly Lys Leu Ser Leu Ala Val Gln Ser Gly Gly Ser Ala Ala
625                 630                 635                 640

Gly Ala Ser His Tyr Leu Glu Val Ser Phe Gly Ser Gly Ser Leu Ala
                645                 650                 655

Ala Gly Ala Ser Thr Gly Glu Met Gln Leu Arg Leu Asn Lys Ser Asp
            660                 665                 670

Trp Ser Asn Phe Asn Glu Ala Asp Asp Tyr Ser His Gly Thr Gly Thr
        675                 680                 685

Ser Phe Ala Asp Ala Ser Lys Ile Gly Val Tyr Thr Ala Gly Ala Leu
    690                 695                 700

Ser Trp Gly Thr Ala Pro
705                 710


<210> SEQ ID NO 4
<211> LENGTH: 790
<212> TYPE: PRT
<213> ORGANISM: Streptomyces LaPpAH-95

<400> SEQUENCE: 4

Met Arg Ser Phe Pro Leu Pro Ala Leu Arg Arg Arg Ser Arg Arg Pro
1               5                   10                  15

Gly Arg Pro Leu Gly Ala Val Ala Leu Ala Leu Ala Val Gly Ala Gly
            20                  25                  30

Leu Leu Leu Pro Leu Ser Leu Pro Ala Gly Ala Ala Ala Ala Pro Ala
        35                  40                  45

Phe Asp Tyr Gly Glu Ala Leu Gln Lys Ser Val Leu Phe Tyr Glu Ala
    50                  55                  60

Gln Gln Ser Gly Lys Leu Pro Asp Thr Asn Arg Val Ser Trp Arg Gly
65                  70                  75                  80

Asp Ser Ala Leu Asp Asp Gly Lys Asp Ala Gly Leu Asp Leu Thr Gly
                85                  90                  95

Gly Trp Tyr Asp Ala Gly Asp His Val Lys Phe Gly Leu Pro Met Ala
            100                 105                 110

Tyr Ser Ala Thr Met Leu Ala Trp Gly Gly Thr Glu Gln Arg Ala Ala
        115                 120                 125

Tyr Glu Ala Ser Gly Gln Leu Pro His Leu Arg Asn Asn Leu Arg Phe
    130                 135                 140

Val Asp Asp Tyr Leu Leu Lys Ala His Pro Ser Pro Asn Val Leu Tyr
145                 150                 155                 160
```

```
Gly Gln Val Gly Asn Gly Gly Asp Asp His Lys Trp Trp Gly Pro Ala
                165                 170                 175

Glu Val Met Pro Met Lys Arg Pro Ala Tyr Lys Ile Asp Ala Ser Cys
            180                 185                 190

Pro Gly Ser Asp Leu Ala Gly Gln Thr Ala Ala Ala Leu Ala Ser Ser
        195                 200                 205

Ser Met Val Phe Ser Asp Ser Asp Pro Ala Tyr Ala Ala Lys Leu Ile
    210                 215                 220

Thr His Ala Lys Gln Leu Tyr Thr Phe Ala Asp Thr Tyr Arg Gly Lys
225                 230                 235                 240

Tyr Ser Asp Cys Ile Thr Asp Ala Gln Ser Tyr Tyr Asn Ser Trp Ser
                245                 250                 255

Gly Tyr Asn Asp Glu Leu Val Trp Gly Ala Ile Trp Leu Tyr Lys Ala
            260                 265                 270

Thr Gly Asp Thr Ala Tyr Leu Ala Lys Ala Glu Ser Tyr Tyr Asp Asn
        275                 280                 285

Leu Ser Thr Glu Pro Gln Thr Thr Thr Arg Ser Tyr Arg Trp Thr Leu
    290                 295                 300

Ser Trp Asp Asp Thr Ser Tyr Gly Ala Tyr Val Leu Leu Ala Gln Leu
305                 310                 315                 320

Thr Gly Lys Gln Lys Tyr Ile Asp Asp Ala Asn Arg Trp Leu Asp Trp
                325                 330                 335

Trp Thr Val Gly Val Asn Gly Gln Arg Val Pro Tyr Ser Pro Gly Gly
            340                 345                 350

Gln Ala Val Leu Asp Ser Trp Gly Ser Leu Arg Tyr Ala Ala Asn Thr
        355                 360                 365

Ala Phe Val Ala Leu Ser Tyr Ser Asp Trp Leu Thr Gly Asp Ala Thr
    370                 375                 380

Arg Lys Ala Arg Tyr His Asp Phe Ala Val Arg Gln Ile Asp Tyr Ala
385                 390                 395                 400

Leu Gly Asp Asn Pro Arg Gly Ser Ser Tyr Val Val Gly Phe Gly Glu
                405                 410                 415

Asn Pro Pro Thr Lys Pro His His Arg Thr Ala His Gly Ser Trp Thr
            420                 425                 430

Asp Gln Met Thr Asn Pro Val Glu Thr Arg His Thr Leu Tyr Gly Ala
        435                 440                 445

Leu Val Gly Gly Pro Ser Ala Pro Asp Asp Thr Tyr Thr Asp Asp Arg
    450                 455                 460

Gly Asn Tyr Val Asn Asn Glu Val Ala Thr Asp Tyr Asn Ala Ala Phe
465                 470                 475                 480

Thr Gly Ala Leu Ala Arg Leu Tyr Ala Glu Tyr Gly Gly Ser Pro Leu
                485                 490                 495

Thr Asp Phe Pro Gln Pro Glu Glu Pro Asp Gly Pro Glu Met Ser Val
            500                 505                 510

Gln Ala Ser Val Asn Ala Ala Gly Ala Asn Phe Thr Glu Val Lys Ala
        515                 520                 525

Tyr Leu Ile Asn Arg Ser Ala Trp Pro Ala Arg Ala Leu Thr Asp Ala
    530                 535                 540

Ser Val Arg Tyr Tyr Phe Thr Leu Glu Pro Gly Val Ala Pro Gly Asp
545                 550                 555                 560

Ile Ser Phe Thr Thr Asn Tyr Asn Gln Cys Gly Glu Val Thr Gly Pro
                565                 570                 575
```

-continued

Thr His Leu Thr Gly Asp Val Tyr Tyr Ala Thr Val Asp Cys Ser Asp
580 585 590

Thr Asp Ile Ala Pro Ala Gly Gln Ser Ala Tyr Arg Lys Glu Val Gln
595 600 605

Phe Arg Ile Ser Ser Ala Gly Ala Trp Asp Pro Ser Asn Asp Trp Ser
610 615 620

Tyr Pro Ser Thr Ala Thr Thr Pro Gly Gly Thr Pro Val Asp Ala Pro
625 630 635 640

His Met Val Leu Leu Glu Gly Ser Ala Pro Gln Trp Gly Thr Ala Pro
645 650 655

Asp Gly Thr Asp Pro Gly Pro Gly Pro Asp Pro Thr Thr Thr Pro Glu
660 665 670

Pro Ser Pro Thr Pro Asp Pro Thr Asp Thr Pro Asp Pro Glu Pro Gly
675 680 685

Ala Cys Asp Val Thr Tyr Arg Val Ser Gln Ala Trp Gly Thr Gly Phe
690 695 700

Thr Ala Asp Val Thr Val Lys Asn Thr Gly Pro Thr Pro Leu Asp Gly
705 710 715 720

Trp Gln Leu Ala Phe Asp Phe Gln Gly Ala Glu Ser Val Ser Asn Ala
725 730 735

Trp Asn Ala Thr Ala Thr Gln Ser Gly Thr Arg Val Thr Leu Lys Asn
740 745 750

Ala Gly His Asn Gly Ser Val Pro Ala Gly Gly Ser Ala Ser Phe Gly
755 760 765

Phe Gln Ala Asn Gly Ala Pro Gly Ala Asp Pro His Ser Phe Thr Leu
770 775 780

Asn Gly Lys Glu Cys Gly
785 790

<210> SEQ ID NO 5
<211> LENGTH: 428
<212> TYPE: PRT
<213> ORGANISM: Streptomyces LaPpAH-95

<400> SEQUENCE: 5

Met Thr Gly Arg Pro Leu Pro Ala Leu Ala Gly Ala Ala Ala Ala Leu
1 5 10 15

Val Leu Ala Ala Ala Ser Met Leu Thr Gly Ala Ser Ser Ala Ser Ala
20 25 30

Ser Pro Val Thr Asp Cys Thr Pro Trp Gly Thr Thr Glu Leu Leu Gly
35 40 45

Gly Glu Tyr Leu Tyr Gln Gln Asn Glu Trp Asn Ser Asp Ser Glu Gln
50 55 60

Cys Val Gly Val Asp Pro Asp Thr Gly Ala Trp Ser Val Thr Thr Ser
65 70 75 80

Ser Phe Asn Leu Pro Thr Asn Gly Ala Pro Ala Thr Tyr Pro Ser Ser
85 90 95

Tyr Lys Gly Cys His Trp Gly Ala Cys Thr Ser Asp Ser Gly Leu Pro
100 105 110

Leu Arg Val Asp Glu Leu Gly Ser Val His Thr Asp Trp Ser Thr Thr
115 120 125

Gln Val Gly Ser Gly Ala Tyr Asn Val Ser Met Asp Val Trp Phe Asn
130 135 140

Ser Ala Pro Val Thr Asp Asp Gln Pro Asp Gly Thr Glu Leu Met Ile
145 150 155 160

Trp Met Asn His Arg Gly Gly Val Gln Pro Ile Gly Ser Arg Thr Ala
165 170 175

Thr Val Gln Leu Asp Gly Arg Thr Trp Asp Val Trp Thr Gly Pro Gly
180 185 190

Ala Ser Gly Trp Lys Val Ile Ser Tyr Val Leu Gln Gly Gly Ala Thr
195 200 205

Glu Leu Thr Gly Phe Asp Val Lys Ser Leu Ile Asp Asp Gly Val Gly
210 215 220

Arg Gly Gln Ile Asp Pro Ala His Tyr Leu Ile Asp Ala Glu Ala Gly
225 230 235 240

Phe Glu Ile Trp Gln Gly Gly Gln Gly Leu Gly Met Lys Glu Phe Ser
245 250 255

Phe Glu Ala Ser Ala Gly Thr Asp Gly Gly Asp Asp Gly Gly Asp Gly
260 265 270

Asp Pro Gly Gly Gly Gly Thr Thr Gly Ala Leu Lys Ala Gln Tyr Lys
275 280 285

Asn Asn Asp Ser Ser Ala Thr Asp Asn Gln Ile Arg Pro Gly Leu Gln
290 295 300

Leu Val Asn Thr Gly Ser Thr Ala Val Asp Leu Ser Thr Val Lys Leu
305 310 315 320

Arg Tyr Trp Phe Thr Pro Glu Ser Gly Ala Ala Gly Phe Gly Thr Ala
325 330 335

Cys Asp Tyr Ala Val Val Gly Cys Gly Asn Val Thr His Thr Val Lys
340 345 350

Gln Ala Gly Thr Ala Ala Gly Ala Ser His Tyr Leu Glu Val Gly Phe
355 360 365

Thr Gly Gly Ser Leu Ala Pro Gly Ala Ser Thr Gly Glu Ile Gln Leu
370 375 380

Arg Phe Asn Lys Ser Asp Trp Ser Ala Phe Asp Glu Ala Asp Asp Tyr
385 390 395 400

Ser Arg Ala Ala Asn Thr Ala Phe Thr Asp Ala Ser Lys Val Gly Val
405 410 415

Tyr Val Asn Gly Ala Leu Ser Ser Gly Thr Ala Pro
420 425

<210> SEQ ID NO 6
<211> LENGTH: 920
<212> TYPE: PRT
<213> ORGANISM: Streptomyces LaPpAH-95

<400> SEQUENCE: 6

Met Leu Ala Val Gly Leu Ala Gln Gly Thr Ala Ile Ala Arg Pro Ala
1 5 10 15

Ser Ala Gln Ala Gly Thr Gly Ala Arg Ala Ala Ala Ala Gly Asp Asp
20 25 30

Pro Tyr Thr Gln Ala Phe Leu Thr Gln Tyr Gly Lys Leu Lys Asp Ala
35 40 45

Ala Asn Gly Tyr Phe Ser Pro Asp Gly Leu Pro Tyr His Ser Val Glu
50 55 60

Thr Leu Met Val Glu Ala Pro Asp His Gly His Gln Thr Thr Ser Glu
65 70 75 80

Ala Val Ser Phe Trp Met Trp Leu Glu Ala Ala Tyr Gly Arg Val Thr
85 90 95

Gly Asp Trp Ala Pro Phe Asn Ala Ala Trp Ala Val Ala Glu Lys Thr

-continued

```
            100                 105                 110

Ile Ile Pro Gln His Ala Asp Gln Ser Thr Ser Asp Ser Tyr Asn Pro
        115                 120                 125

Ser Ala Pro Ala Thr Tyr Ala Pro Glu His Pro Leu Pro Ser Gly Tyr
    130                 135                 140

Pro Ser Ala Leu Asp Gly Thr Val Pro Val Gly Thr Asp Pro Leu Ser
145                 150                 155                 160

Ala Glu Leu Ala Ser Ser Tyr Gly Thr Met Asp Val Tyr Gly Met His
                165                 170                 175

Trp Leu Met Asp Leu Asp Asn Val Tyr Gly Tyr Gly Asn Lys Pro Gly
            180                 185                 190

Thr Gly Gly Glu Ser Gly Pro Gly Ala Gly Ala Ser Phe Ile Asn Thr
        195                 200                 205

Tyr Gln Arg Gly Ala Gln Glu Ser Val Trp Glu Thr Val Pro Gln Pro
    210                 215                 220

Thr Thr Asp Leu Phe Lys Tyr Gly Gly Pro Asn Gly Tyr Leu Asp Leu
225                 230                 235                 240

Phe Val Gly Asp Ser Ser Tyr Ala Lys Gln Trp Lys Tyr Thr Asn Ala
                245                 250                 255

Pro Asp Ala Asp Ala Arg Ala Val Gln Ala Ala Tyr Trp Ala Tyr Arg
            260                 265                 270

Trp Ala Ser Glu Gln Gly Lys Glu Ser Gln Val Ala Ala Ser Val Ala
        275                 280                 285

Lys Ala Ala Lys Met Gly Asp Tyr Leu Arg Tyr Ala Met Phe Asp Lys
    290                 295                 300

Tyr Phe Lys Arg Val Gly Asp Cys Thr Asp Pro Asn Ser Cys Pro Ala
305                 310                 315                 320

Ala Ser Gly Arg Asp Ser Gln His Tyr Leu Leu Ser Trp Tyr Tyr Ala
                325                 330                 335

Trp Gly Gly Ala Ala Ala Gly Ser Gly Gly Gly Trp Ala Trp Arg Ile
            340                 345                 350

Gly Asp Gly Ala Ser His Gln Gly Tyr Gln Asn Pro Leu Ala Ala Trp
        355                 360                 365

Ala Leu Ser Asn Val Pro Ser Leu Thr Pro Lys Ser Ala Thr Ala Arg
    370                 375                 380

Ser Asp Trp Ser Lys Ser Leu Thr Arg Gln Leu Glu Phe Leu Thr Trp
385                 390                 395                 400

Leu Gln Ser Ser Glu Gly Ala Leu Ala Gly Gly Cys Thr Asn Ser Trp
                405                 410                 415

Glu Gly Ser Tyr Ser Thr Pro Pro Ala Gly Thr Pro Thr Phe Tyr Gly
            420                 425                 430

Met Ala Tyr Asp Trp Gln Pro Val Tyr His Asp Pro Ala Ser Asn Asn
        435                 440                 445

Trp Phe Gly Phe Gln Ala Trp Gly Met Glu Arg Val Ala Ala Tyr Tyr
    450                 455                 460

Tyr Val Thr Gly Asn Ala Thr Ala Glu Ala Val Leu Ser Lys Trp Val
465                 470                 475                 480

Ala Trp Ala Ser Ser Glu Thr Thr Ile Gly Ser Asp Gly Ser Phe Arg
                485                 490                 495

Phe Pro Ser Thr Leu Asn Trp Thr Gly Glu Pro Asp Thr Trp Asn Ala
            500                 505                 510

Ala Ser Pro Gly Asp Asn Ala Gly Leu His Val Ser Val Val Asp Tyr
        515                 520                 525
```

-continued

```
Ala Asn Asp Val Gly Val Gly Ala Ala Tyr Val Lys Thr Leu Thr Tyr
    530                 535                 540

Tyr Ala Ala Lys Ser Gly Asp Glu Asp Ala Ala Ala Leu Ala Lys Ala
545                 550                 555                 560

Leu Leu Asp Ala Met Ala Leu Asn Thr Thr Asp Lys Gly Ile Ser Val
                565                 570                 575

Pro Glu Thr Arg Leu Asp Tyr Asn Arg Phe Asp Asp Glu Val Tyr Ile
            580                 585                 590

Pro Ser Gly Trp Ser Gly Thr Met Pro Asn Gly Asp Pro Val Arg Pro
        595                 600                 605

Gly Ser Thr Phe Ile Ser Ile Arg Ser Trp Tyr Lys Asp Asp Pro Asp
    610                 615                 620

Trp Pro Lys Val Gln Ala Tyr Leu Asp Gly Gly Asp Ala Pro Val Phe
625                 630                 635                 640

Thr Tyr His Arg Phe Trp Ala Gln Ala Ala Leu Ala Leu Ala Phe Ala
                645                 650                 655

Ile Tyr Ala Glu Leu Leu Val Glu Gly Gly Gly Gly Glu Pro Gly Gly
            660                 665                 670

Asp Thr Glu Pro Pro Thr Ala Pro Gly Gly Leu Thr Val Thr Ala Thr
        675                 680                 685

Thr Lys Asp Ser Val Ser Leu Ser Trp Ser Ala Ser Thr Asp Asn Thr
    690                 695                 700

Ala Val Thr Gly Tyr Asp Val Tyr Arg Asn Gly Val Leu Ala Gly Asn
705                 710                 715                 720

Ala Thr Gly Arg Thr Phe Thr Asp Ser Gly Leu Ala Ala Asn Thr Glu
                725                 730                 735

Tyr Thr Tyr Ala Val Ala Ala Arg Asp Ala Gly Gly Asn Thr Ser Ala
            740                 745                 750

Leu Ser Asp Ala Val Leu Ala Lys Thr Lys Thr Gly Gly Ser Thr Gly
        755                 760                 765

Thr Gly Ala Val Lys Val Gln Tyr Lys Ser Thr Asp Ser Ser Ala Thr
    770                 775                 780

Asp Asn Gln Ile Arg Met Gly Leu Gln Val Val Asn Thr Gly Ser Ala
785                 790                 795                 800

Pro Val Asp Leu Ser Thr Val Lys Val Arg Tyr Trp Phe Thr Ala Asp
                805                 810                 815

Gly Gly Pro Ser Thr Phe Gly Thr Tyr Cys Asp Tyr Ala Ala Leu Gly
            820                 825                 830

Ser Ser Thr Ile Thr His Thr Val Val Ala Val Ser Ser Pro Lys Thr
        835                 840                 845

Gly Ala Asp Arg Tyr Leu Glu Val Gly Phe Thr Gly Gly Ala Gly Thr
    850                 855                 860

Leu Ala Ala Gly Ala Ser Thr Gly Glu Ile Gln Leu Arg Leu Asn Lys
865                 870                 875                 880

Ser Asp Trp Ser Asn Phe Asn Glu Ala Asp Asp Tyr Ser Arg Ala Thr
                885                 890                 895

Asn Thr Ala Tyr Ala Asp Ser Ser Lys Val Gly Ala Tyr Val Ala Gly
            900                 905                 910

Ala Leu Ala Trp Gly Val Glu Pro
        915                 920
```

<210> SEQ ID NO 7
<211> LENGTH: 367

<212> TYPE: PRT
<213> ORGANISM: Streptomyces LaPpAH-95

<400> SEQUENCE: 7

Met Ala Arg Arg Arg Thr Gln Leu Ala Ser Leu Ala Ala Val Leu Ala
1               5                   10                  15

Thr Leu Leu Gly Gly Ile Ala Phe Thr Leu Leu Gly Gln Gly Ser Ala
            20                  25                  30

Gln Ala His Gly Val Thr Met Ser Pro Gly Ser Arg Thr Tyr Leu Cys
        35                  40                  45

Trp Leu Asp Ala Lys Thr Ser Thr Gly Ser Leu Asp Pro Thr Asn Pro
    50                  55                  60

Ala Cys Lys Ala Ala Leu Ala Glu Ser Gly Ala Ser Ser Leu Tyr Asn
65                  70                  75                  80

Trp Phe Ala Val Leu Asp Ser Asn Ala Gly Gly Arg Gly Ala Gly Tyr
                85                  90                  95

Val Pro Asp Gly Thr Leu Cys Ser Ala Gly Asp Arg Ser Pro Tyr Asn
            100                 105                 110

Phe Thr Gly Tyr Asn Ala Ala Arg Gly Asp Trp Pro Arg Thr His Leu
        115                 120                 125

Thr Ser Gly Ala Lys Ile Glu Val Asp His Ser Asn Trp Ala Ala His
    130                 135                 140

Pro Gly Glu Phe Arg Val Tyr Met Ser Lys Pro Gly Tyr Ser Pro Thr
145                 150                 155                 160

Thr Glu Leu Gly Trp Asp Asp Leu Asp Leu Ile Gln Thr Val Ser Asn
                165                 170                 175

Pro Pro Gln Val Gly Ser Pro Gly Thr Asp Gly Gly His Tyr Tyr Trp
            180                 185                 190

Asp Leu Thr Leu Pro Ser Gly Arg Ser Gly Asp Ala Val Met Phe Ile
        195                 200                 205

Gln Trp Val Arg Ser Asp Ser Gln Glu Asn Phe Phe Ser Cys Ser Asp
    210                 215                 220

Ile Val Phe Asp Gly Gly Asn Gly Glu Val Thr Gly Ile Arg Gly Ser
225                 230                 235                 240

Gly Ser Thr Pro Asp Pro Asp Pro Thr Asp Pro Thr Pro Asp Pro Thr
                245                 250                 255

Asp Pro Thr Asp Pro Thr Asp Pro His Thr Gly Cys Met Ala Val Tyr
            260                 265                 270

Asn Val Thr Asn Ser Trp Ser Gly Gly Phe Gln Gly Ser Val Glu Val
        275                 280                 285

Met Asn His Asn Thr Thr Ala Leu Asp Gly Trp Ala Val Gln Trp Lys
    290                 295                 300

Pro Gly Thr Gly Thr Thr Val Ser Ser Val Trp Ser Gly Val Leu Ser
305                 310                 315                 320

Thr Gly Ser Asp Gly Thr Leu Thr Val Lys Asn Ala Asp Tyr Asn Arg
                325                 330                 335

Ser Ile Pro Pro Asp Gly Ser Val Thr Phe Gly Phe Thr Ala Thr Ser
            340                 345                 350

Thr Gly Asn Asp Phe Pro Val Gly Ser Ile Gly Cys Val Ser Pro
        355                 360                 365

<210> SEQ ID NO 8
<211> LENGTH: 954
<212> TYPE: PRT
<213> ORGANISM: Streptomyces sp SirexAA-E -continued

<400> SEQUENCE: 8

Met Ala Ala Leu Ala Leu Pro Leu Gly Met Thr Ala Ala Ala Gly Thr
1               5                   10                  15

Glu Ala Gln Ala Ala Ala Val Ala Cys Ser Val Asp Tyr Thr Thr Ser
            20                  25                  30

Asp Trp Gly Ser Gly Phe Thr Thr Glu Leu Thr Leu Thr Asn Arg Gly
        35                  40                  45

Ser Ala Ala Ile Asp Gly Trp Thr Leu Thr Tyr Asp Tyr Ala Gly Asn
    50                  55                  60

Gln Gln Leu Thr Ser Gly Trp Ser Gly Thr Trp Ser Gln Ser Gly Lys
65                  70                  75                  80

Thr Val Ser Val Lys Asn Ala Ala Trp Asn Gly Ala Ile Ala Ala Gly
                85                  90                  95

Ala Ala Val Thr Thr Gly Ala Gln Phe Thr Tyr Ser Gly Ala Asn Thr
            100                 105                 110

Ala Pro Thr Thr Phe Ala Val Asn Gly Thr Val Cys Ala Gly Ala His
        115                 120                 125

Gln Pro Pro Ile Ala Val Leu Thr Ser Pro Ala Ala Gly Ala Val Phe
    130                 135                 140

Ser Ala Gly Asp Pro Val Pro Leu Ala Ala Thr Ala Ala Ala Ala Asp
145                 150                 155                 160

Gly Ala Thr Ile Ser Lys Val Glu Phe Tyr Asp Asp Thr Thr Leu Leu
                165                 170                 175

Gly Thr Asp Thr Thr Ser Pro Tyr Ser Tyr Glu Ala Gly Gln Leu Ala
            180                 185                 190

Ala Gly Ser His Ser Val Tyr Ala Arg Ala Tyr Asp Ser Leu Gly Ala
        195                 200                 205

Ser Ala Asp Ser Pro Pro Ala Gly Ile Thr Val Val Thr Gly Pro Ala
    210                 215                 220

Val Val Val Ser Pro Ala Gln Leu Gly Val Gln Gln Gly Arg Ser Gly
225                 230                 235                 240

Thr Phe Asp Val Ser Leu Ser Thr Ala Pro Ala Ala Asp Val Thr Val
                245                 250                 255

Thr Ala Ala Arg Ser Ala Gly Asn Thr Gly Leu Ser Val Thr Gly Gly
            260                 265                 270

Ser Thr Leu Thr Phe Thr Pro Ala Asn Trp Ser Thr Pro Gln Lys Val
        275                 280                 285

Thr Val Thr Ala Asp Gly Ser Gly Thr Gly Ala Ala Thr Phe Thr Val
    290                 295                 300

Thr Ala Pro Gly His Gly Lys Ala Glu Val Thr Val Thr Gln Leu Ala
305                 310                 315                 320

Ala Ala Lys Glu Tyr Asp Ala Arg Phe Leu Asp Leu Tyr Gly Lys Ile
                325                 330                 335

Thr Asp Pro Ala Asn Gly Tyr Phe Ser Pro Glu Gly Ile Pro Tyr His
            340                 345                 350

Ser Val Glu Thr Leu Ile Val Glu Ala Pro Asp His Gly His Glu Thr
        355                 360                 365

Thr Ser Glu Ala Tyr Ser Tyr Leu Ile Trp Leu Gln Ala Met Tyr Gly
    370                 375                 380

Lys Ile Thr Gly Asp Trp Thr Lys Phe Asn Gly Ala Trp Asp Thr Met
385                 390                 395                 400

Glu Thr Tyr Met Ile Pro Thr His Ala Asp Gln Pro Thr Asn Ser Phe

-continued

```
                405                 410                 415

Tyr Asp Ala Ser Lys Pro Ala Thr Tyr Ala Pro Glu His Asp Thr Pro
            420                 425                 430

Asn Glu Tyr Pro Ala Val Leu Asp Gly Ser Ala Ser Ser Gly Ser Asp
        435                 440                 445

Pro Ile Ala Ala Glu Leu Lys Ser Ala Tyr Gly Thr Asp Asp Ile Tyr
    450                 455                 460

Gly Met His Trp Ile Gln Asp Val Asp Asn Val Tyr Gly Tyr Gly Asn
465                 470                 475                 480

Ala Pro Gly Thr Cys Ala Ala Gly Pro Thr Gln Ala Gly Pro Ser Tyr
                485                 490                 495

Ile Asn Thr Phe Gln Arg Gly Ser Gln Glu Ser Val Trp Glu Thr Val
            500                 505                 510

Thr His Pro Thr Cys Asp Asn Phe Thr Tyr Gly Gly Ala Asn Gly Tyr
        515                 520                 525

Leu Asp Leu Phe Thr Gly Asp Ser Ser Tyr Ala Lys Gln Trp Lys Phe
    530                 535                 540

Thr Asn Ala Pro Asp Ala Asp Ala Arg Ala Val Gln Ala Ala Tyr Trp
545                 550                 555                 560

Ala Asp Val Trp Ala Lys Glu Gln Gly Lys Ala Gly Glu Val Ala Asp
                565                 570                 575

Thr Val Gly Lys Ala Ala Lys Met Gly Asp Tyr Leu Arg Tyr Ser Met
            580                 585                 590

Phe Asp Lys Tyr Phe Lys Lys Ile Gly Asp Cys Val Gly Pro Thr Thr
        595                 600                 605

Cys Pro Ala Gly Ser Gly Lys Asp Ser Ala His Tyr Leu Met Ser Trp
    610                 615                 620

Tyr Tyr Ala Trp Gly Gly Ala Thr Asp Thr Ser Ala Gly Trp Ser Trp
625                 630                 635                 640

Arg Ile Gly Ser Ser His Ala His Gly Gly Tyr Gln Asn Pro Met Ala
                645                 650                 655

Ala Tyr Ala Leu Ser Ser Val Ala Asp Leu Lys Pro Lys Ser Ala Thr
            660                 665                 670

Gly Ala Gln Asp Trp Ala Lys Ser Leu Asp Arg Gln Leu Asp Phe Tyr
        675                 680                 685

Gln Trp Leu Gln Ser Asp Glu Gly Ala Ile Ala Gly Gly Ala Thr Asn
    690                 695                 700

Ser Trp Lys Gly Ser Tyr Ala Gln Pro Pro Ala Gly Thr Pro Thr Phe
705                 710                 715                 720

Tyr Gly Met Tyr Tyr Asp Glu Lys Pro Val Tyr His Asp Pro Pro Ser
                725                 730                 735

Asn Gln Trp Phe Gly Phe Gln Ala Trp Ser Met Glu Arg Val Ala Glu
            740                 745                 750

Tyr Tyr His Glu Ser Gly Asp Ala Gln Ala Lys Ala Val Leu Asp Lys
        755                 760                 765

Trp Val Asp Trp Ala Leu Ser Glu Thr Thr Val Asn Pro Asp Gly Thr
    770                 775                 780

Tyr Leu Met Pro Ser Thr Leu Gln Trp Ser Gly Ala Pro Asp Thr Trp
785                 790                 795                 800

Asn Ala Ser Asn Pro Gly Ala Asn Ala Gln Leu His Val Thr Val Ala
                805                 810                 815

Asp Tyr Thr Asp Asp Val Gly Val Ala Gly Ala Tyr Ala Arg Thr Leu
            820                 825                 830
```

Thr Tyr Tyr Ala Ala Lys Ser Gly Asp Thr Glu Ala Glu Ala Thr Ala
835 840 845

Glu Ala Leu Leu Asp Gly Met Trp Gln His His Gln Asp Asp Ala Gly
850 855 860

Val Ala Val Pro Glu Thr Arg Ala Asp Tyr Asn Arg Phe Asp Asp Pro
865 870 875 880

Val Tyr Val Pro Gly Gly Trp Thr Gly Ala Met Pro Asn Gly Asp Thr
885 890 895

Val Asp Glu Asp Ser Thr Phe Leu Ser Ile Arg Ser Phe Tyr Lys Asp
900 905 910

Asp Pro Asn Trp Pro Gln Val Gln Ala Tyr Leu Asp Gly Gly Ala Ala
915 920 925

Pro Val Phe Thr Tyr His Arg Phe Trp Ala Gln Ala Asp Ile Ala Leu
930 935 940

Ala Leu Gly Ala Tyr Ala Asp Leu Leu Glu
945 950

<210> SEQ ID NO 9
<211> LENGTH: 586
<212> TYPE: PRT
<213> ORGANISM: Streptomyces sp SirexAA-E

<400> SEQUENCE: 9

Met Ser Arg Thr Ser Arg Thr Thr Leu Arg Arg Ser Arg Thr Ala Leu
1 5 10 15

Met Ala Ala Gly Ala Leu Val Ala Ala Ala Ala Gly Ser Ala Ala Ala
20 25 30

Ala Ala Pro Phe Gly Ala Thr Ala Ala Ala Ala Ala Gly Cys Thr Val
35 40 45

Asp Tyr Lys Ile Gln Asn Gln Trp Asn Gly Gly Leu Thr Ala Ser Val
50 55 60

Ser Val Thr Asn Asn Gly Asp Ala Ile Ser Gly Trp Gln Leu Gln Trp
65 70 75 80

Ser Phe Ala Gly Gly Glu Gln Val Ser Gln Gly Trp Asn Ala Thr Val
85 90 95

Ser Gln Ser Gly Ser Ala Val Thr Ala Lys Asp Ala Gly Tyr Asn Ala
100 105 110

Ala Leu Ala Thr Gly Ala Ser Ala Ser Phe Gly Phe Asn Ala Thr Gly
115 120 125

Asn Gly Asn Ser Val Val Pro Ala Thr Phe Lys Leu Asn Gly Val Thr
130 135 140

Cys Asn Gly Gly Thr Thr Gly Pro Thr Asp Pro Thr Asp Pro Thr Asp
145 150 155 160

Pro Thr Asp Pro Thr Asp Pro Pro Ala Gly Asn Arg Val Asp Asn Pro
165 170 175

Tyr Gln Gly Ala Lys Val Tyr Val Asn Pro Glu Trp Ser Ala Asn Ala
180 185 190

Ala Ala Glu Pro Gly Gly Asp Arg Ile Ala Asp Gln Pro Thr Gly Val
195 200 205

Trp Leu Asp Arg Ile Ala Ala Ile Glu Gly Ala Asn Gly Ser Met Gly
210 215 220

Leu Arg Asp His Leu Asp Glu Ala Leu Thr Gln Lys Gly Ser Gly Glu
225 230 235 240

Leu Val Val Gln Val Val Ile Tyr Asn Leu Pro Gly Arg Asp Cys Ala

-continued

```
                245                 250                 255

Ala Leu Ala Ser Asn Gly Glu Leu Gly Pro Thr Glu Ile Gly Arg Tyr
            260                 265                 270

Lys Thr Glu Tyr Ile Asp Pro Ile Ala Glu Ile Leu Gly Asp Pro Lys
        275                 280                 285

Tyr Ala Gly Leu Arg Ile Val Thr Thr Val Glu Ile Asp Ser Leu Pro
    290                 295                 300

Asn Leu Val Thr Asn Ala Gly Gly Arg Pro Thr Ala Thr Pro Ala Cys
305                 310                 315                 320

Asp Val Met Lys Ala Asn Gly Asn Tyr Val Lys Gly Val Gly Tyr Ala
                325                 330                 335

Leu Asn Lys Leu Gly Asp Ala Pro Asn Val Tyr Asn Tyr Ile Asp Ala
            340                 345                 350

Gly His His Gly Trp Ile Gly Trp Asp Asp Asn Phe Gly Ala Ser Ala
        355                 360                 365

Glu Ile Phe His Glu Ala Ala Thr Ala Glu Gly Ala Thr Val Asn Asp
    370                 375                 380

Val His Gly Phe Ile Thr Asn Thr Ala Asn Tyr Ser Ala Leu Lys Glu
385                 390                 395                 400

Glu Asn Phe Ser Ile Asp Asp Ala Val Asn Gly Thr Ser Val Arg Gln
                405                 410                 415

Ser Lys Trp Val Asp Trp Asn Arg Tyr Thr Asp Glu Leu Ser Phe Ala
            420                 425                 430

Gln Ala Phe Arg Asn Glu Leu Val Ser Val Gly Phe Asn Ser Gly Ile
        435                 440                 445

Gly Met Leu Ile Asp Thr Ser Arg Asn Gly Trp Gly Gly Ala Asn Arg
    450                 455                 460

Pro Ser Gly Pro Gly Ala Asn Thr Ser Val Asp Thr Tyr Val Asp Gly
465                 470                 475                 480

Gly Arg Tyr Asp Arg Arg Ile His Leu Gly Asn Trp Cys Asn Gln Ala
                485                 490                 495

Gly Ala Gly Leu Gly Glu Arg Pro Gln Ala Ala Pro Glu Pro Gly Ile
            500                 505                 510

Asp Ala Tyr Val Trp Met Lys Pro Pro Gly Glu Ser Asp Gly Ser Ser
        515                 520                 525

Ser Glu Ile Pro Asn Asp Glu Gly Lys Gly Phe Asp Arg Met Cys Asp
    530                 535                 540

Pro Thr Tyr Thr Gly Asn Ala Arg Asn Asn Asn Asn Met Ser Gly Ala
545                 550                 555                 560

Leu Gly Gly Ala Pro Val Ser Gly Lys Trp Phe Ser Ala Gln Phe Gln
                565                 570                 575

Glu Leu Met Lys Asn Ala Tyr Pro Ala Leu
            580                 585


<210> SEQ ID NO 10
<211> LENGTH: 362
<212> TYPE: PRT
<213> ORGANISM: Streptomyces sp SirexAA-E

<400> SEQUENCE: 10

Met Ala Arg Arg Ser Arg Leu Ile Ser Leu Ala Ala Val Leu Ala Thr
1               5                   10                  15

Leu Leu Gly Ala Leu Gly Leu Thr Ala Leu Trp Pro Gly Lys Ala Glu
            20                  25                  30
```

-continued

```
Ala His Gly Val Ala Met Thr Pro Gly Ser Arg Thr Tyr Leu Cys Gln
        35                  40                  45

Leu Asp Ala Leu Ser Gly Thr Gly Ala Leu Asn Pro Thr Asn Pro Ala
    50                  55                  60

Cys Arg Asp Ala Leu Ser Gln Ser Gly Ala Asn Ala Leu Tyr Asn Trp
65                  70                  75                  80

Phe Ala Val Leu Asp Ser Asn Ala Gly Gly Arg Gly Ala Gly Tyr Val
                85                  90                  95

Pro Asp Gly Ser Leu Cys Ser Ala Gly Asp Arg Ser Pro Tyr Asp Phe
            100                 105                 110

Ser Ala Tyr Asn Ala Ala Arg Ala Asp Trp Pro Arg Thr His Leu Thr
        115                 120                 125

Ser Gly Ala Thr Leu Lys Val Gln Tyr Ser Asn Trp Ala Ala His Pro
    130                 135                 140

Gly Asp Phe Arg Val Tyr Leu Thr Lys Pro Gly Trp Ala Pro Thr Ser
145                 150                 155                 160

Glu Leu Ala Trp Asp Asp Leu Gln Leu Val Gln Thr Val Ser Asn Pro
                165                 170                 175

Pro Gln Gln Gly Gly Ala Gly Thr Asn Gly Gly His Tyr Tyr Trp Asp
            180                 185                 190

Leu Ala Leu Pro Ser Gly Arg Ser Gly Asp Ala Leu Met Phe Ile Gln
        195                 200                 205

Trp Val Arg Ser Asp Ser Gln Glu Asn Phe Phe Ser Cys Ser Asp Ile
    210                 215                 220

Val Phe Asp Gly Gly Asn Gly Glu Val Thr Gly Ile Gly Gly Thr Gly
225                 230                 235                 240

Thr Pro Thr Pro Thr Pro Thr Pro Thr Pro Thr Pro Thr Pro Thr Asp
                245                 250                 255

Pro Glu His Ser Gly Ser Cys Met Ala Val Tyr Asn Val Val Ser Ser
            260                 265                 270

Trp Ala Gly Gly Phe Gln Ala Ser Val Glu Val Met Asn His Gly Thr
        275                 280                 285

Glu Pro Arg Asn Gly Trp Ala Val Gln Trp Lys Pro Gly Ser Gly Thr
    290                 295                 300

Gln Ile Asn Ser Val Trp Asn Gly Ser Leu Ser Thr Gly Ser Asp Gly
305                 310                 315                 320

Thr Val Thr Val Arg Asp Val Asp His Asn Arg Val Ile Ala Pro Asp
                325                 330                 335

Gly Ser Val Thr Phe Gly Phe Thr Ala Thr Ser Thr Gly Asn Asp Tyr
            340                 345                 350

Pro Ala Gly Thr Ile Gly Cys Val Thr Ser
        355                 360


<210> SEQ ID NO 11
<211> LENGTH: 909
<212> TYPE: PRT
<213> ORGANISM: Streptomyces sp SirexAA-E

<400> SEQUENCE: 11

Met Trp Cys His Pro Tyr Leu Arg Leu Arg Thr Ser Gly Arg Lys Val
1               5                   10                  15

Ser Ser Val Asn Ala Leu Pro Pro Pro Ala Arg Pro Ala Pro Val Arg
            20                  25                  30

Pro Arg Ser Arg Tyr Gly Arg Arg Val Leu Gly Met Ser Ala Ala Ala
        35                  40                  45
```

-continued

```
Leu Leu Cys Ala Gly Ala Leu Ala Val Pro Gly Thr Ala Met Ala Asp
    50                  55                  60

Asp Ala Glu Pro Gly Pro Gly Pro Glu Gln Ile Thr Asn Gly Asp Phe
65                  70                  75                  80

Ala Thr Gly Thr Ser Ala Pro Trp Trp Trp Thr Pro Asn Ala Ser Ala
                85                  90                  95

Ala Val Ser Glu Gly Arg Leu Cys Val Glu Val Pro Ala Gly Thr Ala
            100                 105                 110

Asn Ala Trp Asp Val Ile Val Gly Gln Asn Asp Val Pro Ile Val Ala
        115                 120                 125

Gly Glu Ser Tyr Glu Leu Ser Tyr Thr Ala Arg Ser Thr Val Pro Leu
    130                 135                 140

Thr Val Gln Thr Arg Val Gln Glu Ala Val Glu Pro Tyr Thr Thr Val
145                 150                 155                 160

Leu Ala Thr Ala Asp Pro Val Gly Ala Glu Asp Thr Arg Val Ala Arg
                165                 170                 175

Thr Phe Thr Ala Ser Val Asp Gln Pro Ala Ala Ser Val Gln Leu Gln
            180                 185                 190

Ile Gly Gly Gly Glu Arg Ala Thr Thr Phe Cys Leu Asp Asp Val Ser
        195                 200                 205

Leu Arg Gly Gly Ala Glu Pro Pro Val Tyr Val Pro Asp Thr Gly Ser
    210                 215                 220

Pro Val Arg Val Asn Gln Val Gly Tyr Leu Pro Arg Gly Pro Lys Ser
225                 230                 235                 240

Gly Thr Val Val Thr Asp Ala Glu Ala Pro Leu Thr Trp Thr Val Lys
                245                 250                 255

Ala Glu Asp Gly Ser Thr Ala Ala Thr Gly Thr Thr Val Pro Arg Gly
            260                 265                 270

Glu Asp Pro Ser Ser Arg Arg Arg Val His Thr Phe Asp Phe Gly Asp
        275                 280                 285

Leu Thr Thr Ala Gly Asp Gly Tyr Thr Val Glu Val Asp Gly Glu Val
    290                 295                 300

Ser Glu Pro Phe Ser Ile Arg Gly Asp Leu Tyr Asp Ser Leu Arg Ser
305                 310                 315                 320

Asp Ala Leu Ala Tyr Phe Tyr His Asn Arg Ser Gly Ile Glu Ile Asp
                325                 330                 335

Ala Asp Leu Val Gly Glu Gln Tyr Ala Arg Pro Ala Gly His Ile Gly
            340                 345                 350

Val Ala Pro Asn Lys Gly Asp Thr Asp Val Pro Cys Arg Pro Gly Val
        355                 360                 365

Cys Asp Tyr Arg Leu Asp Val Ser Gly Gly Trp Tyr Asp Ala Gly Asp
    370                 375                 380

His Gly Lys Tyr Val Val Asn Gly Gly Ile Ser Val Ala Gln Leu Met
385                 390                 395                 400

Ala Thr Tyr Glu Arg Thr Leu Thr Ala Pro Asp Ala Glu Ser Ala Glu
                405                 410                 415

Leu Gly Asp Gly Ala Leu Arg Val Pro Glu Arg Asp Asn Gly Val Pro
            420                 425                 430

Asp Ile Leu Asp Glu Ala Arg Trp Glu Met Asp Phe Leu Ile Lys Met
        435                 440                 445

Gln Val Pro Ala Gly Glu Gln Leu Ala Gly Met Val His His Lys Met
    450                 455                 460
```

-continued

```
His Asp Ala Glu Trp Thr Gly Leu Pro Met Lys Pro His Leu Asp Pro
465                 470                 475                 480

Gln Gln Arg Glu Leu His Pro Pro Ser Thr Ala Ala Thr Leu Asn Leu
                485                 490                 495

Ala Ala Thr Ala Ala Gln Cys Ala Arg Leu Tyr Ala Pro Phe Asp Ala
            500                 505                 510

Asp Phe Ala Asp Arg Cys Leu Arg Ala Ala Glu Thr Ala Trp Asp Ala
        515                 520                 525

Ala Lys Arg His Pro Asp Val Leu Ala Asp Pro Asn Asp Gly Ile Gly
    530                 535                 540

Gly Gly Ala Tyr Asn Asp Asp Asp Val Ser Asp Glu Phe Tyr Trp Ala
545                 550                 555                 560

Ala Ala Glu Leu Phe Thr Thr Thr Gly Lys Asp Ile Tyr Arg Gln Ala
                565                 570                 575

Val Leu Ser Ser Ala Trp His Gly Asp Ala Gly Ala Val Phe Pro Ala
            580                 585                 590

Gly Gly Gly Ile Ser Trp Gly Ser Thr Ala Gly Leu Gly Val Leu Thr
        595                 600                 605

Leu Ala Thr Val Pro Asn Ala Leu Thr Ser Asp Gln Leu Ala Gln Val
    610                 615                 620

Arg Thr Val Val Thr Glu Gly Ala Asp Arg Tyr Ala Ala Gln Ser Arg
625                 630                 635                 640

Glu Gln Ala Tyr Gly Leu Pro Tyr Ala Pro Arg Gly Glu Asp Tyr Val
                645                 650                 655

Trp Gly Ser Asn Ser Gln Val Leu Asn Asn Met Val Val Leu Ala Thr
            660                 665                 670

Ala His Asp Leu Thr Gly Asp Ala Ala Tyr Gln Asp Ala Val Leu Arg
        675                 680                 685

Gly Ala Asp Tyr Leu Leu Gly Arg Asn Pro Leu Asn Gln Ser Tyr Val
    690                 695                 700

Thr Gly Tyr Gly Glu Arg Asp Ser His Asn Gln His His Arg Phe Trp
705                 710                 715                 720

Ala His Gln Asn Asp Pro Ser Leu Pro Asn Pro Ala Pro Gly Ser Ile
                725                 730                 735

Ala Gly Gly Pro Asn Leu Thr Ala Ile Ala Ser Gly Asp Pro Val Ala
            740                 745                 750

Ala Glu Lys Leu Ser Gly Cys Ala Pro Ala Met Cys Tyr Val Asp Asp
        755                 760                 765

Ile Gly Ser Trp Ala Thr Asn Glu Ile Thr Ile Asn Trp Asn Ala Pro
    770                 775                 780

Leu Ala Phe Ile Ala Ser Tyr Leu Asp Asp Ala Gly Glu Gly Gly Gln
785                 790                 795                 800

Thr Ala Ala Ala Arg Thr Cys Gln Val Thr Tyr Ser Ser His Pro Trp
                805                 810                 815

Asn Ser Gly Ser Thr Val Thr Val Arg Val Glu Asn Thr Gly Ser Asp
            820                 825                 830

Pro Val Ser Pro Trp Ala Leu Thr Trp Leu Leu Pro Gly Glu Gln Arg
        835                 840                 845

Leu Ser His Thr Trp Ser Ala Glu Phe Asp Gln His Gly Arg Thr Val
    850                 855                 860

Ser Ala Arg Pro Leu Ser Trp Asn Arg Thr Leu Ala Pro Gly Ala Ala
865                 870                 875                 880

Val Asp Phe Gly Phe Asn Thr Ser Ala Ala Gly Ser Ser Pro Glu Pro
```

885 890 895

Gly Ala Phe Lys Leu Asn Gly Arg Ala Cys Ser Ala Gly
900 905

<210> SEQ ID NO 12
<211> LENGTH: 456
<212> TYPE: PRT
<213> ORGANISM: Streptomyces sp SirexAA-E

<400> SEQUENCE: 12

Met Lys Arg Phe Leu Ala Leu Leu Ala Thr Cys Ala Thr Val Leu Gly
1 5 10 15

Leu Thr Ala Leu Thr Gly Pro Gln Ala Val Ala Ala Ala Gly Cys Thr
20 25 30

Ala Asp Tyr Thr Ile Thr Ser Gln Trp Gln Gly Gly Phe Gln Ala Ala
35 40 45

Val Lys Val Thr Asn Leu Gly Thr Pro Val Thr Gly Trp Lys Leu Thr
50 55 60

Phe Thr Leu Pro Asp Ala Gly Gln Lys Val Val Gln Gly Trp Asn Ala
65 70 75 80

Ala Trp Ser Gln Ser Gly Ser Ala Val Thr Ala Ala Gly Ala Asp Trp
85 90 95

Asn Gly Thr Leu Ala Thr Gly Ala Ser Ala Glu Ala Gly Phe Val Gly
100 105 110

Ser Phe Thr Gly Ala Asn Pro Pro Pro Thr Ala Phe Ala Leu Asn Gly
115 120 125

Val Ala Cys Thr Gly Ser Thr Gly Glu Pro Pro Ala Gly Ser Asp Gly
130 135 140

Gly Thr Pro Val Asp Val Asn Gly Gln Leu His Val Cys Gly Val Asn
145 150 155 160

Leu Cys Asn Gln Tyr Asp Arg Pro Val Gln Leu Arg Gly Met Ser Thr
165 170 175

His Gly Ile Gln Trp Phe Asp Ala Cys Tyr Asp Ala Ala Ser Leu Asp
180 185 190

Ala Leu Ala Asn Asp Trp Lys Ser Asp Leu Leu Arg Ile Ala Met Tyr
195 200 205

Val Gln Glu Asp Gly Tyr Glu Thr Asp Pro Ala Gly Phe Thr Arg Arg
210 215 220

Val Asn Asp Leu Val Asp Met Ala Glu Ala Arg Gly Met Tyr Ala Leu
225 230 235 240

Ile Asp Phe His Thr Leu Thr Pro Gly Asp Pro Asn Val Asn Leu Asp
245 250 255

Arg Ala Lys Thr Phe Phe Ala Ser Val Ala Ala Arg Asn Ala Gly Lys
260 265 270

Lys Asn Val Ile Tyr Glu Ile Ala Asn Glu Pro Asn Gly Val Thr Trp
275 280 285

Thr Ala Val Lys Ser Tyr Ala Glu Gln Val Ile Pro Val Ile Arg Ala
290 295 300

Ala Asp Pro Asp Ala Val Val Ile Val Gly Thr Arg Gly Trp Ser Ser
305 310 315 320

Leu Gly Val Ser Asp Gly Ser Asp Glu Ser Glu Val Val Asn Ser Pro
325 330 335

Val Asn Ala Thr Asn Ile Met Tyr Ala Phe His Phe Tyr Ala Ala Ser
340 345 350

```
His Lys Asp Ala Tyr Arg Ser Thr Leu Ser Arg Ala Ala Ala Arg Leu
        355                 360                 365

Pro Leu Phe Val Thr Glu Phe Gly Thr Val Ser Ala Thr Gly Gly Gly
    370                 375                 380

Ala Met Asp Arg Ala Ser Thr Thr Ala Trp Leu Asp Leu Leu Asp Gln
385                 390                 395                 400

Leu Lys Ile Ser Tyr Ala Asn Trp Thr Tyr Ser Asp Ala Pro Glu Ser
                405                 410                 415

Ser Ala Ala Phe Arg Pro Gly Thr Cys Gly Gly Gly Asp Tyr Ser Gly
            420                 425                 430

Ser Gly Val Leu Thr Glu Ser Gly Ala Leu Leu Lys Asn Arg Ile Ser
        435                 440                 445

Thr Pro Asp Ser Phe Pro Thr Gly
    450                 455


<210> SEQ ID NO 13
<211> LENGTH: 583
<212> TYPE: PRT
<213> ORGANISM: Streptomyces DpondAA-B6

<400> SEQUENCE: 13

Met Ser Arg Thr Ser Arg Thr Thr Leu Arg Arg Ser Arg Thr Ala Leu
1               5                   10                  15

Ile Ala Ala Gly Ala Leu Val Ala Ala Ala Ala Gly Ser Ala Ala Ala
            20                  25                  30

Ala Ala Pro Phe Ala Ala Ser Ala Ala Ala Ala Thr Gly Cys Thr Val
        35                  40                  45

Asp Tyr Lys Ile Glu Asn Gln Trp Asn Gly Gly Leu Thr Ala Ala Val
    50                  55                  60

Asn Val Thr Asn Asn Gly Ala Pro Val Thr Ser Trp Gln Leu Gln Trp
65                  70                  75                  80

Thr Phe Asn Gly Gly Glu Gln Val Ser Gln Gly Trp Asn Ala Thr Ile
                85                  90                  95

Ser Gln Ser Gly Ser Ala Val Thr Ala Lys Asp Ala Gly Tyr Asn Gly
            100                 105                 110

Thr Leu Ala Thr Gly Ala Ser Ala Ser Phe Gly Phe Asn Ala Thr Gly
        115                 120                 125

Asn Gly Asn Ser Thr Val Pro Ala Thr Phe Lys Leu Asn Gly Val Thr
    130                 135                 140

Cys Asn Gly Asp Thr Thr Gly Pro Thr Asp Pro Thr Asp Pro Thr Asp
145                 150                 155                 160

Pro Thr Asp Pro Pro Ala Gly Asn Arg Val Asp Asn Pro Tyr Gln Gly
                165                 170                 175

Ala Lys Val Tyr Val Asn Pro Glu Trp Ser Ala Asn Ala Ala Ala Glu
            180                 185                 190

Pro Gly Gly Ser Arg Val Ala Asn Gln Pro Thr Gly Val Trp Leu Asp
        195                 200                 205

Arg Ile Ala Ala Ile Glu Gly Ala Asn Gly Ser Met Gly Leu Arg Glu
    210                 215                 220

His Leu Asp Glu Ala Leu Thr Gln Lys Gly Ser Gly Glu Leu Val Val
225                 230                 235                 240

Gln Leu Val Ile Tyr Asp Leu Pro Gly Arg Asp Cys Ala Ala Leu Ala
                245                 250                 255

Ser Asn Gly Glu Leu Gly Pro Thr Glu Ile Gly Arg Tyr Lys Thr Glu
            260                 265                 270
```

-continued

```
Tyr Ile Asp Pro Ile Ala Ala Ile Val Ala Asp Pro Lys Tyr Ala Gly
        275                 280                 285

Leu Arg Ile Val Thr Thr Val Glu Ile Asp Ser Leu Pro Asn Leu Val
    290                 295                 300

Thr Asn Ala Gly Gly Arg Glu Thr Ala Thr Pro Ala Cys Asp Val Met
305                 310                 315                 320

Lys Ala Asn Gly Asn Tyr Val Lys Gly Val Gly Tyr Ala Leu Asn Lys
                325                 330                 335

Leu Gly Asp Ala Pro Asn Val Tyr Asn Tyr Ile Asp Ala Gly His His
            340                 345                 350

Gly Trp Ile Gly Trp Asp Asp Asn Phe Gly Ala Ser Ala Gln Ile Phe
        355                 360                 365

His Glu Ala Ala Thr Ala Glu Gly Ala Thr Val Asn Asp Val His Gly
    370                 375                 380

Phe Ile Thr Asn Thr Ala Asn Tyr Ser Ala Leu Lys Glu Gln Asn Phe
385                 390                 395                 400

Ser Ile Asn Asp Ser Val Asn Gly Thr Ser Val Arg Glu Ser Lys Trp
                405                 410                 415

Val Asp Trp Asn Arg Tyr Thr Asp Glu Leu Ser Phe Ala Gln Ala Phe
            420                 425                 430

Arg Asn Glu Leu Val Ser Val Gly Phe Asn Ser Gly Ile Gly Met Leu
        435                 440                 445

Ile Asp Thr Ser Arg Asn Gly Trp Gly Gly Ser Ala Arg Pro Ser Gly
    450                 455                 460

Pro Gly Ala Thr Thr Ser Val Asp Thr Tyr Val Asp Gly Gly Arg Tyr
465                 470                 475                 480

Asp Arg Arg Ile His Leu Gly Asn Trp Cys Asn Gln Ala Gly Ala Gly
                485                 490                 495

Leu Gly Glu Arg Pro Thr Ala Ala Pro Glu Pro Gly Ile Asp Ala Tyr
            500                 505                 510

Val Trp Met Lys Pro Pro Gly Glu Ser Asp Gly Ser Ser Ser Glu Ile
        515                 520                 525

Pro Asn Asp Glu Gly Lys Gly Phe Asp Arg Met Cys Asp Pro Thr Tyr
    530                 535                 540

Thr Gly Asn Pro Arg Asn Asn Asn Asn Pro Ser Gly Ala Leu Gly Gly
545                 550                 555                 560

Ala Pro Val Ser Gly Lys Trp Phe Ser Ala Gln Phe Gln Glu Leu Met
                565                 570                 575

Lys Asn Ala Tyr Pro Ala Leu
            580


<210> SEQ ID NO 14
<211> LENGTH: 888
<212> TYPE: PRT
<213> ORGANISM: Streptomyces DpondAA-B6

<400> SEQUENCE: 14

Met Asn Ala Leu Pro Pro Pro Ala Arg Pro Ala Pro Val Arg Ser Arg
1               5                   10                  15

Ser Arg Tyr Gly Arg Arg Ala Leu Gly Ile Ser Ala Ala Ala Leu Leu
            20                  25                  30

Cys Ala Gly Ala Leu Ala Val Pro Gly Thr Ala Leu Ala Asp Asp Ala
        35                  40                  45

Ala Pro Gly Pro Glu Gln Ile Thr Asn Gly Asp Phe Ser Ala Gly Thr
```

```
    50                  55                  60

Ala Pro Trp Trp Trp Thr Pro Asn Ala Ser Ala Ala Val Ser Glu Gly
65                  70                  75                  80

Arg Leu Cys Val Glu Val Pro Ala Gly Thr Ala Glu Ala Trp Asp Val
                85                  90                  95

Ile Val Gly Gln Asn Asp Ile Pro Ile Val Ala Gly Glu Ser Tyr Glu
            100                 105                 110

Leu Ser Tyr Thr Ala Arg Ser Thr Val Pro Leu Thr Val Gln Thr Arg
        115                 120                 125

Val Gln Glu Ala Val Glu Pro Tyr Gly Thr Val Leu Ala Thr Ala Asp
    130                 135                 140

Pro Val Gly Thr Glu Asp Thr Gln Val Thr Arg Thr Phe Thr Ala Ser
145                 150                 155                 160

Val Asp Gln Pro Ala Ala Ser Val Gln Leu Gln Ile Gly Gly Gly Glu
                165                 170                 175

Arg Ala Thr Thr Phe Cys Leu Asp Asp Val Ser Leu Arg Gly Gly Ala
            180                 185                 190

Glu Pro Pro Val Tyr Val Pro Asp Thr Gly Ser Pro Val Arg Val Asn
        195                 200                 205

Gln Val Gly Tyr Leu Pro Arg Gly Val Lys Ser Gly Thr Val Val Thr
    210                 215                 220

Asp Ala Glu Ala Pro Leu Thr Trp Thr Val Lys Ala Gly Asp Gly Ser
225                 230                 235                 240

Thr Ala Ala Thr Gly Thr Thr Val Pro Arg Gly Glu Asp Pro Ser Ser
                245                 250                 255

Arg Gln Arg Val His Thr Phe Asp Phe Gly Gly Leu Thr Thr Pro Gly
            260                 265                 270

Asp Gly Tyr Thr Val Glu Val Asp Gly Glu Val Ser Glu Pro Phe Ser
        275                 280                 285

Ile Arg Gly Asp Leu Tyr Asp Gly Leu Arg Ser Asp Ala Leu Ala Tyr
    290                 295                 300

Phe Tyr His Asn Arg Ser Gly Ile Glu Ile Asp Ala Asp Leu Val Gly
305                 310                 315                 320

Glu Glu Tyr Ala Arg Pro Ala Gly His Ile Gly Val Ala Pro Asn Lys
                325                 330                 335

Gly Asp Thr Asp Val Pro Cys Lys Pro Gly Val Cys Asp Tyr Arg Leu
            340                 345                 350

Asp Val Ser Gly Gly Trp Tyr Asp Ala Gly Asp His Gly Lys Tyr Val
        355                 360                 365

Val Asn Gly Gly Ile Ser Val Ala Gln Leu Met Ser Thr Tyr Glu Arg
    370                 375                 380

Thr Leu Thr Ala Asp Asn Ala Glu Ser Ala Gln Leu Asp Asp Gly Ala
385                 390                 395                 400

Leu Arg Val Pro Glu Arg Gly Asn Gly Val Pro Asp Ile Leu Asp Glu
                405                 410                 415

Ala Arg Trp Glu Met Asp Phe Leu Ile Lys Met Gln Val Pro Ala Gly
            420                 425                 430

Glu Pro Leu Ala Gly Met Val His His Lys Met His Asp Ala Glu Trp
        435                 440                 445

Thr Gly Leu Pro Met Lys Pro His Leu Asp Pro Gln Gln Arg Glu Leu
    450                 455                 460

His Ala Pro Ser Thr Ala Ala Thr Leu Asn Leu Ala Ala Thr Ala Ala
465                 470                 475                 480
```

-continued

Gln Cys Ala Arg Leu Tyr Ala Pro Tyr Asp Glu Asp Phe Ala Asp Arg
485 490 495

Cys Leu Arg Ala Ala Glu Thr Ala Trp Asp Ala Ala Lys Arg His Pro
500 505 510

Asp Val Phe Ala Asp Pro Asn Asp Gly Val Gly Gly Gly Thr Tyr Asp
515 520 525

Asp Asn Asp Val Ser Asp Glu Phe Tyr Trp Ala Ala Ala Glu Leu Phe
530 535 540

Thr Thr Thr Gly Lys Asp Thr Tyr Arg Gln Glu Val Leu Ser Ser Asp
545 550 555 560

Leu His Gly Asp Ala Asp Ala Val Phe Pro Ala Gly Gly Gly Leu Ser
565 570 575

Trp Gly Ala Thr Ala Gly Leu Gly Ala Leu Thr Leu Ala Thr Val Pro
580 585 590

Asn Asn Leu Thr Thr Asp Gln Leu Asp Gly Val Arg Ala Thr Val Thr
595 600 605

Thr Ala Ala Asp Arg Tyr Ala Ala Gln Ser Arg Ala Gln Ala Tyr Gly
610 615 620

Leu Pro Tyr Ala Pro Arg Gly Thr Asp Tyr Val Trp Gly Ser Asn Ser
625 630 635 640

Gln Val Leu Asn Asn Met Val Val Leu Ala Val Ala His Asp Leu Thr
645 650 655

Gly Glu Ala Ala Tyr Gln Asp Ala Val Leu Arg Gly Ala Asp Tyr Leu
660 665 670

Phe Gly Arg Asn Pro Leu Asn Gln Ser Tyr Val Thr Gly Tyr Gly Glu
675 680 685

Arg Asp Ser His Asn Gln His His Arg Phe Trp Ala His Gln Tyr Asp
690 695 700

Ser Ser Leu Pro Asn Pro Ala Pro Gly Ser Val Ala Gly Gly Pro Asn
705 710 715 720

Leu Thr Ala Ala Gly Ser Gly Asp Pro Val Ala Ala Glu Lys Leu Ser
725 730 735

Gly Cys Ala Pro Ala Met Cys Tyr Ile Asp Asp Ile Gly Ser Trp Ser
740 745 750

Thr Asn Glu Ile Thr Val Asn Trp Asn Ala Pro Leu Ala Phe Ile Ala
755 760 765

Ser Tyr Leu Asp Asp Ala Gly Asp Gly Gly Gln Thr Thr Ala Ser Arg
770 775 780

Thr Cys Glu Val Thr Tyr Ser Ser His Pro Trp Ser Gly Gly Ser Thr
785 790 795 800

Val Ser Val Arg Val Glu Asn Thr Gly Ser Ala Pro Val Glu Pro Trp
805 810 815

Ser Leu Thr Trp Leu Leu Pro Gly Glu Gln Lys Leu Ser His Thr Trp
820 825 830

Ser Ala Glu Phe Glu Gln His Gly Arg Thr Val Ser Ala Arg Pro Leu
835 840 845

Ala Trp Asn Arg Thr Leu Ala Pro Gly Ala Ala Val Asp Phe Gly Phe
850 855 860

Asn Thr Ser Ala Thr Gly Ala Ala Ala Asp Pro Gly Thr Phe Lys Leu
865 870 875 880

Asn Gly Arg Ala Cys Ala Ser Gly
885

```
<210> SEQ ID NO 15
<211> LENGTH: 379
<212> TYPE: PRT
<213> ORGANISM: Streptomyces DpondAA-B6

<400> SEQUENCE: 15

Met Lys Ser Leu Ile Ala Ser Leu Arg Ser Ala Gly Thr Ala Val Thr
1               5                   10                  15

Ala Ser Leu Val Ala Leu Ala Thr Cys Ala Ala Leu Gly Ala Leu Ala
            20                  25                  30

Ala Pro Ala Gln Ala Ala Asp Ser Ile Cys Gly Gln Tyr Gly Thr Thr
        35                  40                  45

Val Ile Gln Asp Arg Tyr Val Val Gln Asn Asn Arg Trp Gly Thr Thr
    50                  55                  60

Asp Ala Gln Cys Val Asp Val Thr Asp Asp Gly Phe Thr Val Thr Arg
65                  70                  75                  80

Ala Asp Gly Ser Val Pro Thr Asn Gly Ala Pro Lys Ser Tyr Pro Ser
                85                  90                  95

Val Tyr Asn Gly Cys His Tyr Thr Asn Cys Ser Pro Gly Thr Glu Leu
            100                 105                 110

Pro Lys Arg Leu Asp Ser Ile Ser Ser Ala Pro Thr Ala Ile Thr Tyr
        115                 120                 125

Thr Tyr Val Asp Gly Ala Val Tyr Asp Ala Ala Tyr Asp Ile Trp Leu
    130                 135                 140

Asp Pro Gln Pro Lys Lys Asp Gly Val Asn Arg Thr Glu Ile Met Ile
145                 150                 155                 160

Trp Phe Asn Arg Val Gly Pro Ile Gln Pro Val Gly Ser Gln Thr Gly
                165                 170                 175

Thr Ala Thr Val Ala Gly Arg Gly Trp Glu Val Trp Thr Gly Asn Asn
            180                 185                 190

Gly Gly Asn Asp Val Ile Ser Phe Val Ser Pro Ser Ala Ile Ser Ser
        195                 200                 205

Trp Ser Phe Asp Val Met Asp Phe Val Asp Ala Thr Val Ala Arg Gly
    210                 215                 220

Met Ala Gln Asn Ser Trp Tyr Leu Thr Ser Val Gln Ala Gly Phe Glu
225                 230                 235                 240

Pro Trp Gln Asn Gly Ala Gly Leu Ala Val Ser Ser Phe Ser Ser Ser
                245                 250                 255

Val Leu Thr Gly Gly Gly Ser Glu Gly Pro Gly Glu Pro Gly Thr Pro
            260                 265                 270

Ala Asp Gly Pro Cys Ala Val Ser Tyr Thr Ala Asn Ala Trp Thr Asp
        275                 280                 285

Gly Phe Thr Ala Asp Val Lys Val Thr Asn Thr Gly Thr Val Pro Val
    290                 295                 300

Ser Gly Trp Arg Leu Gly Phe Thr Leu Pro Gln Gly Gln Thr Val Thr
305                 310                 315                 320

Gln Ala Trp Asn Ala Thr Val Thr Pro Ser Ser Gly Ala Val Thr Ala
                325                 330                 335

Thr Gly Ala Ala Phe Asn Ala Glu Ile Ala Ala Gly Ala Ser Gln Ser
            340                 345                 350

Phe Gly Phe Gln Gly Thr His Ser Gly Thr Phe Thr Lys Pro Asp Arg
        355                 360                 365

Phe Thr Leu Asn Gly Ala Val Cys Thr Val Gly
    370                 375
```

<210> SEQ ID NO 16
<211> LENGTH: 954
<212> TYPE: PRT
<213> ORGANISM: Streptomyces DpondAA-B6

<400> SEQUENCE: 16

```
Met Ala Ala Leu Ala Leu Pro Leu Gly Met Thr Ala Ala Ala Gly Thr
1               5                   10                  15

Pro Ala Gln Ala Ala Ala Val Ala Cys Ser Val Asp Tyr Lys Ala Asn
            20                  25                  30

Asp Trp Gly Ser Gly Phe Thr Thr Glu Leu Thr Leu Thr Asn Arg Gly
        35                  40                  45

Ser Gly Ala Ile Asp Gly Trp Thr Leu Thr Tyr Asp Tyr Ala Gly Asn
    50                  55                  60

Gln Gln Leu Thr Ser Gly Trp Ser Gly Val Trp Ser Gln Ser Gly Lys
65                  70                  75                  80

Thr Val Thr Val Lys Asn Ala Asp Trp Asn Gly Thr Val Ala Ala Gly
                85                  90                  95

Gln Ala Val Thr Ala Gly Ala Gln Phe Thr Tyr Ser Gly Thr Asn Thr
            100                 105                 110

Asp Pro Thr Ala Phe Ala Val Asn Gly Thr Val Cys Ala Gly Ala His
        115                 120                 125

Gln Pro Pro Ile Ala Val Leu Thr Ser Pro Ala Ala Gly Ala Val Phe
    130                 135                 140

Thr Ala Gly Asp Pro Val Pro Leu Ala Ala Thr Ala Ala Ala Ala Asp
145                 150                 155                 160

Gly Ala Thr Ile Ser Lys Val Glu Phe Tyr Asp Asn Thr Thr Leu Leu
                165                 170                 175

Gly Thr Asp Thr Thr Ser Pro Tyr Ser Tyr Thr Ala Gln Gly Leu Ser
            180                 185                 190

Ala Gly Ser His Ser Val Tyr Ala Arg Ala Tyr Asp Ser Leu Gly Ala
        195                 200                 205

Ser Ala Glu Ser Pro Pro Ala Gly Ile Thr Val Ala Ala Gly Pro Ala
    210                 215                 220

Val Val Ala Thr Pro Ala Gln Leu Gly Val Gln Gln Gly Lys Ser Gly
225                 230                 235                 240

Thr Phe Asn Val Ser Leu Ser Thr Ala Pro Ala Ser Asn Val Thr Ala
                245                 250                 255

Thr Val Ala Arg Thr Ala Gly Asn Thr Gly Leu Ser Val Thr Gly Gly
            260                 265                 270

Ala Ser Leu Thr Phe Thr Pro Ala Asn Trp Ser Thr Pro Gln Lys Val
        275                 280                 285

Thr Val Ser Ala Asp Gly Ser Gly Thr Gly Ala Ala Thr Phe Thr Val
    290                 295                 300

Ser Ala Pro Gly His Gly Lys Ala Glu Val Thr Val Thr Gln Leu Ala
305                 310                 315                 320

Gly Ala Lys Glu Tyr Asp Ala Arg Phe Leu Asp Leu Tyr Gly Lys Val
                325                 330                 335

Thr Asp Pro Ala Asn Gly Tyr Phe Ser Pro Glu Gly Ile Pro Tyr His
            340                 345                 350

Ser Val Glu Thr Leu Ile Val Glu Ala Pro Asp His Gly His Glu Thr
        355                 360                 365

Thr Ser Glu Ala Tyr Ser Tyr Leu Ile Trp Leu Gln Ala Met Tyr Gly
```

-continued

```
    370                 375                 380

Lys Ile Thr Gly Asp Trp Thr Arg Phe Asn Gly Ala Trp Asp Thr Met
385                 390                 395                 400

Glu Thr Tyr Met Ile Pro Thr His Ala Asp Gln Pro Thr Asn Ala Tyr
                405                 410                 415

Tyr Asp Ala Ser Lys Pro Ala Thr Tyr Ala Pro Glu His Asp Thr Pro
            420                 425                 430

Asn Glu Tyr Pro Ala Val Leu Asp Gly Ser Val Ser Ser Gly Ser Asp
        435                 440                 445

Pro Ile Ala Ala Glu Leu Lys Ser Ala Tyr Gly Thr Asp Asp Ile Tyr
    450                 455                 460

Gly Met His Trp Ile Gln Asp Val Asp Asn Val Tyr Gly Tyr Gly Asn
465                 470                 475                 480

Ser Pro Gly Thr Cys Ala Ala Gly Pro Thr Gln Thr Gly Pro Ser Tyr
                485                 490                 495

Ile Asn Thr Phe Gln Arg Gly Pro Gln Glu Ser Val Trp Glu Thr Val
            500                 505                 510

Thr His Pro Thr Cys Asp Asn Phe Thr Tyr Gly Gly Ala Asn Gly Tyr
        515                 520                 525

Leu Asp Leu Phe Thr Gly Asp Ser Ser Tyr Ala Lys Gln Trp Lys Phe
    530                 535                 540

Thr Asn Ala Pro Asp Ala Asp Ala Arg Ala Val Gln Ala Ala Tyr Trp
545                 550                 555                 560

Ala Asp Val Trp Ala Lys Glu Gln Gly Lys Ser Ala Asp Val Ala Gly
                565                 570                 575

Thr Val Gly Lys Ala Ala Lys Met Gly Asp Tyr Leu Arg Tyr Ser Met
            580                 585                 590

Phe Asp Lys Tyr Phe Lys Lys Ile Gly Asp Cys Val Gly Pro Thr Thr
        595                 600                 605

Cys Pro Ala Gly Ser Gly Lys Asp Ser Ser His Tyr Leu Met Ser Trp
    610                 615                 620

Tyr Tyr Ala Trp Gly Gly Ala Thr Asp Thr Ser Ala Gly Trp Ala Trp
625                 630                 635                 640

Arg Ile Gly Ser Ser His Ala His Gly Gly Tyr Gln Asn Pro Met Ala
                645                 650                 655

Ala Tyr Ala Leu Ser Ser Val Ala Asp Leu Lys Pro Lys Ser Ala Thr
            660                 665                 670

Gly Gln Gln Asp Trp Ala Lys Ser Leu Asp Arg Gln Leu Asp Phe Tyr
        675                 680                 685

Gln Trp Leu Gln Ser Asp Glu Gly Ala Ile Ala Gly Gly Ala Thr Asn
    690                 695                 700

Ser Trp Lys Gly Gly Tyr Ala Gln Pro Pro Ala Gly Thr Pro Thr Phe
705                 710                 715                 720

His Gly Met Tyr Tyr Asp Glu Lys Pro Val Tyr His Asp Pro Pro Ser
                725                 730                 735

Asn Gln Trp Phe Gly Phe Gln Ala Trp Ser Met Glu Arg Val Ala Glu
            740                 745                 750

Tyr Tyr His Glu Ser Gly Asp Ala Gln Ala Lys Ala Val Leu Asp Lys
        755                 760                 765

Trp Val Asp Trp Ala Leu Ser Glu Thr Thr Val Asn Pro Asp Gly Thr
    770                 775                 780

Tyr Leu Met Pro Ser Thr Leu Gln Trp Ser Gly Ala Pro Asp Thr Trp
785                 790                 795                 800
```

Asn Ala Ser Asn Pro Gly Ser Asn Ala Gly Leu His Val Thr Val Ala
805 810 815

Asp Tyr Thr Asn Asp Val Gly Val Ala Gly Ala Tyr Ala Arg Thr Leu
820 825 830

Thr Tyr Tyr Ala Ala Lys Ser Gly Asp Ala Asp Ala Lys Ala Thr Ala
835 840 845

Glu Ala Leu Leu Asp Gly Met Trp Gln His Tyr Gln Asp Asp Ala Gly
850 855 860

Val Ala Val Pro Glu Thr Arg Ala Asp Tyr Asn Arg Phe Asp Asp Pro
865 870 875 880

Val Tyr Val Pro Gly Gly Trp Thr Gly Ala Met Pro Asn Gly Asp Thr
885 890 895

Val Asp Gln Asp Ser Thr Phe Val Ser Ile Arg Ser Phe Tyr Gln Asp
900 905 910

Asp Pro Asn Trp Pro Lys Val Gln Ala Tyr Leu Asp Gly Gly Ala Ala
915 920 925

Pro Val Phe Thr Tyr His Arg Phe Trp Ala Gln Ala Asp Ile Ala Leu
930 935 940

Ala Leu Gly Ala Tyr Ala Asp Leu Leu Glu
945 950

<210> SEQ ID NO 17
<211> LENGTH: 360
<212> TYPE: PRT
<213> ORGANISM: Streptomyces DpondAA-B6

<400> SEQUENCE: 17

Met Ala Gly Arg Ser Arg Leu Ile Ser Leu Ala Ala Val Leu Ala Thr
1 5 10 15

Leu Leu Gly Ala Leu Gly Leu Thr Ala Leu Trp Gln Gly Lys Ala Glu
20 25 30

Ala His Gly Val Ala Met Met Pro Gly Ser Arg Thr Tyr Leu Cys Gln
35 40 45

Val Asp Ala Leu Ser Gly Thr Gly Ala Leu Asn Pro Thr Asn Pro Ala
50 55 60

Cys Arg Asp Ala Leu Ser Lys Ser Gly Ala Asn Ala Leu Tyr Asn Trp
65 70 75 80

Phe Ala Val Leu Asp Ser Asn Ala Gly Gly Arg Gly Ala Gly Tyr Val
85 90 95

Pro Asp Gly Thr Leu Cys Ser Ala Gly Asp Arg Ser Pro Tyr Asp Phe
100 105 110

Ser Ala Tyr Asn Ala Ala Arg Ala Asp Trp Pro Lys Thr His Leu Thr
115 120 125

Ser Gly Ala Gly Ile Gln Leu Gln Tyr Ser Asn Trp Ala Ala His Pro
130 135 140

Gly Asp Phe Arg Val Tyr Val Thr Lys Pro Ser Trp Ser Pro Thr Ser
145 150 155 160

Ala Leu Gly Trp Asn Asp Leu Gln Leu Val Gln Thr Val Ser Asn Pro
165 170 175

Pro Gln Gln Gly Ser Pro Gly Ala Asn Gly Gly His Tyr Tyr Trp Asp
180 185 190

Leu Thr Leu Pro Ser Gly Arg Ser Gly Asp Ala Leu Met Phe Ile Gln
195 200 205

Trp Val Arg Ser Asp Ser Gln Glu Asn Phe Phe Ser Cys Ser Asp Ile

-continued

```
    210                 215                 220

Val Phe Asp Gly Gly Lys Gly Glu Val Thr Gly Ile Gly Gly Ser Gly
225                 230                 235                 240

Asn Gly Thr Pro Thr Pro Thr Pro Thr Pro Thr Pro Thr Asp Pro Glu
                245                 250                 255

His Ser Gly Ser Cys Met Ala Val Tyr Asn Val Glu Ser Ser Trp Asn
            260                 265                 270

Gly Gly Phe Gln Ala Ser Val Glu Val Met Asn His Gly Thr Glu Pro
        275                 280                 285

Arg Asn Gly Trp Ala Val Gln Trp Lys Pro Gly Thr Gly Thr Gln Ile
    290                 295                 300

Asn Ser Val Trp Asn Gly Thr Leu Ser Thr Gly Ser Asp Gly Thr Val
305                 310                 315                 320

Thr Val Arg Asn Val Asp His Asn Arg Val Ile Ala Pro Asp Gly Ser
                325                 330                 335

Val Thr Phe Gly Phe Thr Ala Asn Ser Thr Gly Asn Asp Phe Pro Ala
            340                 345                 350

Gly Thr Ile Gly Cys Val Thr Ser
        355                 360


<210> SEQ ID NO 18
<211> LENGTH: 1089
<212> TYPE: DNA
<213> ORGANISM: Streptomyces sp SirexAA-E

<400> SEQUENCE: 18

atggcccgcc gcagccgact gatctcactt gcagcggtct tggcaacctt gcttggcgca     60

ttgggtctga cggccctgtg gccgggcaag gccgaagcgc atggtgtcgc aatgacaccc    120

ggtagccgga cctacctgtg ccagttggac gccctcagtg ggacaggtgc gcttaacccg    180

acgaaccccg cctgtcgaga tgcactgagc cagtcgggtg ccaacgccct ctataattgg    240

ttcgcagtac tggactctaa cgccggcgga aggggagcgg gctatgtgcc agacggatcc    300

ctgtgcagtg caggggaccg ctccccctac gatttctcag catacaatgc ggcacgtgcc    360

gactggccgc ggacccacct gacgagcggc gccacactca aggtccaata ttcgaactgg    420

gcagcacacc ccggtgactt ccgtgtgtat ctgacaaaac ccggatgggc gccgacctca    480

gagctggcct gggatgacct tcagctcgtg caaaccgtct cgaatccgcc ccaacaagga    540

ggagcaggca ccaacggggg gcactactat tgggatctgg cgctgccgag cgggagaagt    600

ggagacgcat tgatgttcat ccagtgggtg cgttcggata gccaggagaa cttcttctcg    660

tgtagtgata tagtgttcga cggaggtaat ggggaggtaa ctggaatcgg gggaacggga    720

acacccacac cgacccccac gccgaccccc acccctacgc cgacagaccc tgagcatagc    780

ggtagttgca tggcagtcta caacgtggtc agttcatggg ccgggggatt ccaggcaagc    840

gtggaagtca tgaaccacgg cacggagccg cgcaacgggt gggcggttca atggaagccg    900

gggagcggta cccagattaa cagtgtatgg aacggatcgc tgtccaccgg tagcgacggg    960

acggtcacag tgcgggacgt cgaccacaac cgtgtaatcg caccggatgg tagtgtgacg   1020

ttcggtttca ccgccacatc aaccggcaat gactatcccg cagggacgat cggatgcgtg   1080

acctcgtag                                                            1089


<210> SEQ ID NO 19
<211> LENGTH: 2865
<212> TYPE: DNA
```

-continued

<213> ORGANISM: Streptomyces sp SirexAA-E

<400> SEQUENCE: 19
atggcagcac ttgcactccc gctggggatg acggccgcag cgggtacgga ggcacaggcc 60
gcagcggtag cctgtagcgt cgattacacc accagcgact ggggcagtgg tttcactaca 120
gagctcacat tgaccaaccg cggaagcgca gccatcgatg gctggacgct tacatacgac 180
tatgcgggta atcagcagct gacgagcgga tggagtggta cctggtccca gagcggcaaa 240
acagtctctg tcaaaaacgc agcctggaat ggagcaattg cggcgggagc agcggtaacg 300
acaggtgccc aattcacgta cagtggagcc aataccgccc cgacaacctt cgcagtaaac 360
ggaaccgtgt gcgccggagc acatcagccg ccaatcgcag tcctgaccag tccggcagcc 420
ggagcagttt tctcggcggg ggatccagtg cccttggcgg cgacagcggc agccgcagac 480
ggtgcaacaa tctcgaaggt cgaattttac gacgacacga cgctgctcgg taccgacaca 540
acatcgccgt acagttatga ggccggacag ctcgccgcag gttctcacag tgtatacgca 600
agagcctacg actctctggg agcctcagca gatagtcctc cggcgggcat aacggtcgtc 660
acaggaccgg cggtcgtagt atcaccagcg cagctgggtg tgcagcaagg taggagcgga 720
acgttcgacg tatccctgag cacggccccc gcagctgacg tgaccgtgac agccgcacgt 780
tcggcaggta atacgggctt gtcggtgacc gggggcagca cgcttacctt cacacccgcc 840
aactggtcga cgccgcaaaa agtgacagtc acagcagacg gatcgggaac gggtgcggca 900
acattcacgg tcactgcacc gggtcacggc aaggcagagg tgaccgtcac gcagctggcg 960
gcagcgaagg agtacgacgc ccgcttcctt gacctctacg gaaaaatcac ggaccccgcg 1020
aacgggtatt tcagcccgga gggtattccc tatcactcgg tggaaacctt gatcgttgaa 1080
gccccggacc acggacatga aaccacgtcg gaagcatatt cctacctgat atggctgcag 1140
gcaatgtatg ggaaaatcac aggagactgg acgaagttca acggagcatg ggataccatg 1200
gaaacgtaca tgatcccgac ccacgcagac caaccgacta atagcttcta tgatgcgagt 1260
aagcccgcaa catacgcccc ggagcacgac acccccaatg aatatccggc agtcctggac 1320
ggttcggcaa gttccggaag cgaccccata gccgcagagc tcaaatcggc atatggtacg 1380
gatgacatct acggcatgca ctggatccag gatgtggaca atgtctatgg ttacggaaac 1440
gccccgggca cctgtgcagc ggggcccaca caggcaggtc caagctacat caacacgttc 1500
caacgggggt cccaggagag cgtatgggag acggtcaccc acccgacatg cgacaatttc 1560
acgtatggag gcgcaaacgg ttacctcgat ctgttcaccg gcgattcgtc gtacgcgaag 1620
cagtggaagt tcacaaatgc cccggacgca gacgcccgcg ccgtgcaagc agcatattgg 1680
gcggacgtgt gggccaagga acaaggcaag gcaggagagg tcgcagacac agtgggaaag 1740
gcagcgaaga tgggtgacta tctgcgctac agcatgttcg acaagtattt caagaagatt 1800
ggcgattgcg taggaccgac cacatgcccc gcaggttcgg gcaaggactc cgcacactat 1860
cttatgagct ggtactatgc atggggcggc gccacggaca cttcggcagg ctggtcctgg 1920
cgcatcggtt ccagccatgc acatggtggc tatcagaacc cgatggcagc gtacgcactg 1980
tcctccgtag cagatctcaa gccgaagagc gccacgggtg cacaagattg ggcaaagagt 2040
ctggaccggc agttggactt ctaccagtgg ctgcagtccg acgagggcgc gatcgcgggg 2100
ggtgcaacca atagctggaa gggatcgtat gcacaaccgc ccgcgggcac gcccaccttc 2160
tatggaatgt actatgacga aaagccggtg tatcacgacc cgccgagcaa ccaatggttc 2220
gggttccagg catggagcat ggagcgagtc gcagaatact accatgagtc gggcgacgca 2280

-continued caggcaaagg cagtcctgga taagtgggtg gactgggccc tctcagaaac gacagtcaac 2340
cccgacggaa cgtatctcat gcccagcaca ttgcagtggt cgggtgcgcc ggatacatgg 2400
aatgcaagta acccgggtgc aaacgcccaa ctccacgtga ccgtggcaga ctatacagac 2460
gatgtcggcg tggccggggc atacgcccgc acgcttacgt attatgccgc aaaaagcggc 2520
gacacggaag cagaggcgac cgccgaggca ctgctggatg gtatgtggca acatcaccag 2580
gacgacgcgg gtgtggcagt ccccgaaacc cgcgcggact ataatcgatt tgacgatccg 2640
gtgtatgtcc cgggaggttg gactggcgcc atgccgaacg gagacacagt ggatgaggac 2700
agtacgttct tgtcaatccg ttcgttttat aaagacgatc ccaactggcc gcaggtccag 2760
gcatatctgg acggtggtgc cgcaccggtc ttcacttacc atagattctg ggcacaagca 2820
gatattgcac tggccctggg tgcatacgca gacctcctcg aatga 2865

<210> SEQ ID NO 20
<211> LENGTH: 1371
<212> TYPE: DNA
<213> ORGANISM: Streptomyces sp SirexAA-E

<400> SEQUENCE: 20
atgaagcgct tcctggcact cctcgccacc tgtgcaacgg tcctcgggct gaccgccctt 60
acaggacccc aagcagtagc cgcggcggga tgcaccgccg attataccat aacgtcgcag 120
tggcagggcg gattccaagc agcagtaaaa gtgaccaatc tgggtacacc ggtcaccggt 180
tggaagctca cattcacatt gccggatgca gggcagaaag tggtgcaggg ctggaacgca 240
gcgtggagcc aatcgggatc ggcggtgaca gccgcagggg ccgactggaa tggtaccctt 300
gcaaccggtg cgagtgcaga ggcgggcttc gtcggttcgt tcacaggggc caacccgcca 360
ccgacagcgt tcgcactcaa tggagtcgcc tgtaccggtt caaccggtga gccaccggcg 420
ggaagcgatg gcggcacacc ggtcgatgta aacggtcagc tccatgtatg tggagtcaac 480
ctgtgtaacc agtacgaccg tccagtgcaa ttgcgcggta tgtccaccca cggtatccag 540
tggttcgacg catgctatga cgcggcaagt ctggacgcgc tggccaacga ctggaagtcc 600
gacctcctgc gaattgcaat gtatgtgcag gaagacggat acgagacaga cccggccgga 660
ttcacgcgtc gggtcaatga cctggtagac atggcagaag cccgcggcat gtatgccctg 720
atagatttcc acacgctgac tcccggtgac ccgaatgtca accttgatcg tgccaagacc 780
ttcttcgcga gcgtggccgc aagaaatgcc ggtaaaaaga acgtcatcta tgagatcgca 840
aacgagccga acggagtaac ctggacagca gtcaagtcgt atgccgagca ggtgataccc 900
gtcatccgcg cagcagaccc ggacgcagtg gtaatcgtgg gaaccagggg ttggagcagt 960
ctcggtgtca gcgacggatc ggacgagagt gaagtggtca acagtccggt gaatgccacc 1020
aacattatgt acgcattcca cttttatgcc gcgagccaca aagacgcgta cagaagtacg 1080
ctcagcaggg cggcagcacg tcttcccctg ttcgtcacag aattcggtac cgtaagtgcc 1140
accggtggag gagccatgga tcgggcaagc accaccgcgt ggctggacct gctcgatcag 1200
ctcaaaatct cgtatgcaaa ctggacatac agtgacgcac cggagagctc cgcggccttc 1260
cgcccgggga cctgtggtgg aggtgactat tccggatcag gtgtattgac ggagagcggc 1320
gcacttctca agaatcgtat aagtacaccg gattcattcc cgactggtta a 1371

<210> SEQ ID NO 21
<211> LENGTH: 2730
<212> TYPE: DNA

-continued

<213> ORGANISM: Streptomyces sp SirexAA-E

<400> SEQUENCE: 21

```
atgtggtgcc accccctacct gcgtctccgc accagcggac gaaaggtatc cagtgtaaat     60
gctttgcctc ccccagcacg tcctgcacct gtgcggccac ggtcccggta cggtcgccgg    120
gtcctcggaa tgtcggcggc cgcactcctg tgtgccggag cactcgcagt accgggtaca    180
gcgatggcag atgatgccga accggggccg ggtccagagc agatcacgaa cggtgacttc    240
gccaccggaa cgtcggcacc gtggtggtgg acgcccaacg cgtccgcagc cgtgtcggaa    300
ggtcgtctgt gcgtagaggt gccggcaggc acggccaatg catgggatgt aatagtcggc    360
cagaacgacg tacccatcgt cgcgggtgaa agttacgagc tcagttacac cgcccgctcg    420
acagtcccgc tcacggtgca aacccgggtc caagaggcag tggagccgta caccacggta    480
ctggccaccg cagaccccgt aggtgcggag gatacacgcg tggcacgcac gttcacggcg    540
tccgtcgacc aaccggcggc atcagtacag ctgcagatag gcggaggaga acgggcaacc    600
accttctgtt tggacgacgt gtctctgcgc ggaggcgcag agcccccggt gtatgtcccg    660
gatacaggga gtccggtgcg cgtgaaccag gtaggttacc ttcccagggg accaaagtcg    720
ggcacagtgg tcaccgacgc agaagcgccc ctgacgtgga ccgtgaaggc agaggacggt    780
tcgaccgcgg ccaccggtac gaccgtcccg cggggagaag acccgagctc gcgccgacgt    840
gtgcacacat tcgatttcgg tgacctcacc acagccggcg acggatatac cgtagaggtc    900
gacggtgagg taagcgagcc cttctcaatt cgcggtgatc tgtacgactc gctgcgtagc    960
gacgccctcg cgtatttcta tcataaccga tcgggaatcg agatcgacgc cgacctggtc   1020
ggggagcaat acgcacgtcc cgcaggtcac attggcgtcg caccgaataa gggagacacc   1080
gacgtcccgt gtcgccctgg agtgtgtgat taccgcctcg acgtctccgg gggatggtac   1140
gacgcgggcg atcacgggaa atatgtagtg aacggaggta tcagcgtggc ccagcttatg   1200
gcaacgtacg aacgtaccct cacggcgccg gatgcggagt cggccgaact cggagatggt   1260
gcactccgcg tcccggagcg cgacaatgga gtgcctgaca ttttggacga agcacggtgg   1320
gagatggatt tcctgatcaa gatgcaggta ccggctggcg aacaactcgc aggcatggtg   1380
caccacaaaa tgcacgacgc cgaatggacc ggactcccaa tgaagcccca tctcgacccc   1440
cagcagcgcg agctgcatcc tccgtccacg gcagcaacac tcaatttggc agccaccgca   1500
gcacagtgtg cacgtctgta tgccccattc gacgcagact tcgccgatcg ctgtctgagg   1560
gccgcagaaa ccgcctggga cgcagccaaa aggcacccgg acgtcctcgc agatcccaac   1620
gacggaatcg gtggcggtgc atataatgac gacgatgtat cagacgagtt ctactgggca   1680
gcggccgagt tgttcaccac gacagggaag gatatttacc gtcaggcggt cttgtcgagc   1740
gcctggcatg gagacgcagg tgccgtattc ccggcgggcg gaggtatctc gtggggtagc   1800
acggcaggcc tcggtgtcct taccctggca acagtcccca acgctttgac ctcggatcag   1860
ctcgcacagg tgcgaaccgt agtgaccgag ggagccgacc gctatgcagc ccagtcaagg   1920
gaacaagcat acgggctccc gtatgcgccc cgtggcgagg actatgtatg ggcagcaat   1980
tcgcaggtcc tgaataacat ggtggtcttg gccacggcac acgacctgac aggtgacgca   2040
gcgtaccagg atgcagtgct ccggggcgcc gactatctcc tgggcaggaa tcctcttaac   2100
caaagctacg taaccgggta tggtgaacgt gacagccaca atcagcacca tcgtttttgg   2160
gcgcaccaaa acgatccgtc gttgcccaac ccggcccccg gctcgattgc cggcggaccc   2220
aacctcacag caatcgcaag tggcgatccc gtagcagcgg agaagctgag cggttgtgca   2280
```

```
cccgcaatgt gctacgtgga cgatattgga agttgggcaa ccaacgaaat cacgatcaac   2340

tggaacgcgc ccttggcctt catcgcctcc tatctggacg acgcaggtga gggagggcag   2400

acagccgcag cccgcacgtg ccaagtcacc tattcgagcc acccgtggaa cagtggatca   2460

acagtaacgg tccgtgtgga gaataccggt tcggatccgg tgtcgccctg ggccctcacg   2520

tggttgctgc cgggggaaca gcgcctcagt cacacttggt cagccgagtt cgaccaacat   2580

ggccgtacgg tcagcgcacg ccccctgtcg tggaatcgta cactggcacc gggagcggca   2640

gtggacttcg gattcaacac gtcagccgca ggctcgagtc cggagccggg ggcattcaag   2700

ctcaacggaa gggcatgtag cgcaggttga                                    2730


<210> SEQ ID NO 22
<211> LENGTH: 1752
<212> TYPE: DNA
<213> ORGANISM: Streptomyces DpondAA-B6

<400> SEQUENCE: 22

atgagtcgta cgagccgaac cacgctgcgc cggtcgcgca cagccctgat cgcagcagga     60

gccctcgtag cagcagcagc gggcagtgca gccgcagccg cacctttcgc agcgtccgca    120

gcagccgcaa ccggatgcac cgtagactat aaaatcgaga accagtggaa cggaggactg    180

acagccgcag tcaacgtcac caacaacggc gcgccggtaa cgtcatggca gctgcagtgg    240

accttcaatg gggagaacaa agtctcccag ggatggaacg caacaatcag ccagagcggg    300

tcagcagtaa ctgcaaaaga tgccggttac aatggtacac tggcaacagg cgccagcgca    360

tcgtttggat tcaacgccac aggtaatggc aacagtaccg tcccggcgac attcaaactg    420

aacggagtga cctgtaacgg ggataccacc ggacccacag acccaacgga tcctacggac    480

ccgacggatc ccccggcagg gaatcgcgtg gacaacccgt atcagggcgc aaaggtatac    540

gtgaatccgg agtggagcgc gaacgccgca gcggaacctg gggttcccg tgtcgcaaac    600

caacccaccg gagtgtggct cgaccgcata gcagcgatcg agggtgccaa tggatcgatg    660

ggtttgcgtg agcatctgga cgaagccttg acccagaagg gtagcggaga gctggtcgta    720

caactcgtga tttatgactt gccgggtcgc gactgtgcgg ccctggcatc caacggcgaa    780

ctcggaccga cagaaatcgg cagatataag accgagtaca tcgacccaat cgcggccata    840

gtcgcggacc ccaaatatgc cggactgcgt atcgtaacaa cggtggaaat agacagcctg    900

cctaatctgg taacgaacgc aggtggccgt gaaaccgcaa caccggcatg tgatgtcatg    960

aaggcaaacg gaaactatgt caagggcgtg ggatatgcac tgaacaagct cggagacgcg   1020

cccaatgtct acaactatat tgacgccggt caccacggat ggatcgggtg ggacgataat   1080

ttcggcgcat cggcgcaaat attccacgaa gcagcaactg cggagggagc aaccgtaaac   1140

gacgtgcacg gtttcatcac gaacacggcg aattacagcg cactgaaaga acagaacttc   1200

agcatcaacg atagcgtcaa tggcacttcc gtgagggaat cgaagtgggt cgactggaac   1260

cgctacacgg acgagctcag cttcgcacaa gcgttccgga acgaacttgt gagcgtcggc   1320

ttcaattcgg gtattgggat gctgatcgac accagtcgaa acggctgggg aggtagcgca   1380

cggcccagtg gaccaggggc taccaccagt gtcgacacgt atgtggatgg tggccgctat   1440

gaccggcgca tccacctggg aaactggtgc aatcaagccg gagcaggttt gggggaacga   1500

ccaaccgcag cccccgagcc cggtatcgac gcatatgttt ggatgaagcc gccgggagag   1560

tcggacgggt ccagctccga gatccctaat gatgagggta aaggcttcga ccgcatgtgt   1620
```

-continued gacccgacat acacgggaaa cccccggaac aacaacaatc cgtcgggcgc attgggggga 1680
gcgcccgtga gtggtaagtg gttctcggcc cagttccagg agctcatgaa gaacgcatat 1740
cctgcactct ga 1752

<210> SEQ ID NO 23
<211> LENGTH: 1083
<212> TYPE: DNA
<213> ORGANISM: Streptomyces DpondAA-B6

<400> SEQUENCE: 23
atggccggca ggtcccgcct gatttccctc gcggcggtcc tggccacatt gctgggtgca 60
ctgggcctca ccgccctctg gcagggtaag gcggaagcac atggggtcgc aatgatgccc 120
ggaagccgga catatctgtg ccaagtggac gccctctctg gcaccggagc actgaacccg 180
acaaacccgg catgtcgcga tgcgctgagc aaatcgggtg caaatgccct gtacaattgg 240
ttcgcagtcc tggacagtaa cgccggcgga agaggtgcag gctacgtgcc ggatgggacc 300
ctgtgctccg ccggcgacag aagcccgtac gacttcagcg catataatgc ggcacgtgcc 360
gactggccga agacgcacct gacgagtggc gcaggaatcc agttgcagta tagcaattgg 420
gccgcacatc cgggcgactt ccgagtctac gtcactaagc cgtcgtggtc acccacaagc 480
gcgctcggat ggaacgacct gcagctggta cagaccgtgt cgaatccgcc gcagcagggc 540
agccctggag ccaacggtgg tcactattat tgggacctca ccctgccgtc gggtcggtcg 600
ggggacgcac tgatgttcat ccagtgggtc cgtagcgaca gtcaggagaa cttcttctcc 660
tgttcggaca tagtattcga cggaggcaag ggcgaagtga ccggtatcgg ggggtccggt 720
aatggaacac cgacacccac acccaccccc acgcccacag atcccgagca cagcgggtcg 780
tgtatggccg tatataacgt ggagtcctcg tggaatggag gcttccaggc cagcgtagag 840
gtaatgaatc acggtaccga gccgcgaaac ggatgggcgg tccagtggaa gccgggaacg 900
ggtacgcaga tcaacagtgt atggaacggt accctgtcca cagggtcgga cggtaccgtc 960
acagtcagga acgtggacca taaccgcgta atagcaccgg atggaagcgt cactttcggc 1020
ttcaccgcca attcgacagg aaacgacttc cccgcgggca cgatcggatg tgtaacgagt 1080
tga 1083

<210> SEQ ID NO 24
<211> LENGTH: 2865
<212> TYPE: DNA
<213> ORGANISM: Streptomyces DpondAA-B6

<400> SEQUENCE: 24
atggcagcac tggccttgcc gctgggtatg accgcagcgg caggcacccc ggcacaggca 60
gcagcggtag catgctcagt agactacaag gccaacgatt ggggttcggg cttcaccacc 120
gaactgacac tcacaaatcg cggtagtggt gcgatcgacg gatggacact cacgtacgat 180
tatgccggta accagcagtt gacatcagga tggtcgggtg tgtggagtca gagtggtaag 240
acggtaacag tgaagaacgc agactggaac ggaaccgtcg cggccggcca ggcagtcaca 300
gccggtgcac agttcacgta tagtggaacc aatacagacc cgacagcgtt cgcagtgaac 360
gggaccgtat gcgcgggagc acaccagccc ccgatagccg tcctcaccag ccctgcagca 420
ggagcggtct tcacagcagg cgatccggta ccgctggccg caaccgcagc agcagcggac 480
ggtgcgacca tttccaaggt ggagttctac gacaacacta cactgctcgg cacagacact 540
acctcaccat actcatatac agcgcaagga ctgtcagccg ggagtcattc cgtgtatgca 600

-continued

```
cgcgcatacg actcattggg tgcgagcgca gaaagtccgc cagccggaat caccgtcgca    660
gcgggtccgg cagtagtcgc aacacccgcc cagctcggag tacagcaggg aaagtcgggc    720
accttcaacg tgtccctttc aactgcaccg gcctcaaatg tcacagcaac cgtcgcacgg    780
acggcaggaa atacaggatt gagcgtcacc ggaggcgcgt cactgacctt cacgcccgcc    840
aactggtcga cccctcaaaa agtaaccgtc tccgcagatg gttcgggaac aggagcagca    900
acgttcacag tgagtgcgcc tggtcacgga aaggcagagg taacggtaac gcagctcgcg    960
ggtgcaaagg agtatgatgc acgattcctg gacttgtacg gcaaagtgac cgatccggcc   1020
aacgggtact tctctccgga gggaatacca taccactcag tggagacgct gattgtcgaa   1080
gcgccggacc acggtcatga gacgaccagt gaagcctata gctacttgat atggctgcaa   1140
gcaatgtacg gcaagatcac gggtgactgg acccgcttca acggcgcgtg ggacacaatg   1200
gaaacctata tgatccccac acacgcagac cagccgacca atgcatatta cgacgccagt   1260
aagcctgcaa catacgcacc cgagcacgac accccaaacg aatacccggc ggtacttgac   1320
ggaagcgtat catcgggctc agaccccatc gccgccgagc tgaagtcggc atatggaacc   1380
gatgacatct atggaatgca ctggatccag gatgtcgaca acgtatacgg ctacgggaac   1440
agtccgggaa cgtgtgctgc agggccaacc cagaccggac cgagctatat caacaccttc   1500
cagaggggtc cccaggagtc ggtgtgggag acggtcacgc acccaacatg cgacaatttc   1560
acctacgggg gagcaaatgg atatctcgat ctgttcacag gtgactcaag ctatgcgaag   1620
caatggaagt tcacgaacgc ccccgacgcg gacgcaagag cagtacaagc agcatactgg   1680
gcagacgtat gggccaaaga acaaggtaag agtgcagacg tggcgggcac agtgggtaag   1740
gcggcaaaga tgggagacta tctgcggtac tcaatgttcg acaagtattt caagaagatc   1800
ggtgactgcg tcggcccgac cacctgcccg gcaggctctg gtaaagatag ttctcactac   1860
ctcatgagtt ggtactatgc ctggggcgga gcaaccgaca cctcggcagg gtgggcatgg   1920
cgtataggaa gttcacacgc acacggcggt taccaaaacc ctatggcagc gtatgcgttg   1980
tcgtcggtgg cagacctgaa gccaaagagt gcaacgggcc agcaggattg ggcaaagagc   2040
ctggaccgcc agttggactt ctaccaatgg ttgcagtcgg acgaagggggc gatcgcagga   2100
ggcgccacca actcgtggaa gggtgggtat gcccagccgc cggcgggtac acccacgttc   2160
cacggaatgt actacgacga gaagcccgta taccacgacc cgccctccaa tcagtggttc   2220
ggattccaag cctggtcaat ggaacgggtc gcagagtatt atcatgagtc aggtgatgca   2280
caggcgaagg ccgtgctcga caagtgggtc gattgggcac tgtcggaaac tacagtcaat   2340
cccgacggaa cctacctgat gccatcaaca ctgcagtgga gcggcgcccc tgacacctgg   2400
aacgcatcaa acccgggatc gaatgcgggt ctgcacgtga cagtagcaga ctatacgaac   2460
gacgtgggtg tggccggtgc atacgcgagg acgctgacat attacgccgc aaagagcgga   2520
gacgccgatg ccaaggcaac cgcagaggca ctgctcgacg gcatgtggca gcactaccaa   2580
gatgacgcgg gagtggccgt ccccgagacg cgcgcagatt ataaccggtt cgacgatcca   2640
gtgtacgtcc ccggtggctg gaccggtgcc atgccgaatg gggataccgt ggaccaggac   2700
tcgacattcg tatccataag gtccttctat caggatgacc ccaactggcc gaaggtccag   2760
gcctaccttg acggtggagc ggcgccggtc ttcacgtacc accgtttttg ggcccaggca   2820
gatatcgctt tggccttggg tgcctatgca gacctgctcg aatga                   2865
```

<210> SEQ ID NO 25

<211> LENGTH: 1140
<212> TYPE: DNA
<213> ORGANISM: Streptomyces DpondAA-B6

<400> SEQUENCE: 25

```
atgaagagcc tcatcgcctc cctcaggtca gcaggcacgg cagtcacagc aagcctggtg     60
gcgctcgcca cctgcgcagc cttgggagca ctggcagcac cggcacaggc agcagattcg    120
atctgtggcc agtatggaac gacggtaatc caagaccgct atgtcgtcca aaacaaccga    180
tggggaacca cggacgcgca gtgtgtggac gtgaccgacg atgggttcac cgtaacgcgc    240
gcagacggct cggtccccac caatggagca ccgaagtcgt atccgagcgt ctataacggt    300
tgtcattaca caaattgttc gccgggaacc gagctcccga agcggctgga tagtatcagc    360
tccgccccca cagcgatcac atatacgtac gtcgacggtg ccgtatacga cgcagcatat    420
gacatctggc tcgatcctca gccgaaaaag gacggcgtga acaggacaga gatcatgatc    480
tggttcaatc gggtggggcc catacagccg gtcggtagcc agacgggtac cgccacggtg    540
gcaggtagag ggtgggaagt ctggaccggt aacaacggag gtaatgacgt catttccttc    600
gtatccccgt cggcaatctc cagctggagt ttcgacgtca tggacttcgt agacgcaacg    660
gtggcgcgcg gaatggcaca gaactcatgg tatctgacct cggtgcaggc gggcttcgaa    720
ccgtggcaga acggagccgg cctcgcagta tcgtccttct caagttcggt gttgaccggt    780
ggcggttcag agggacccgg cgagccggga acaccggccg atggtccgtg cgcagtcagc    840
tataccgcca acgcatggac agacggattc acggcagacg tgaaggtcac caatacaggc    900
acagtgccag tctcgggatg gcggttgggt ttcacactgc cccaggggca gacggtcacc    960
caggcatgga acgccacggt aaccccgtcg agtggagcag tgacggccac cggtgcagcg   1020
ttcaacgcag agatagcagc aggggcaagt cagagtttcg gatttcaagg tacccactcg   1080
ggaaccttca caaagcccga ccgtttcacc ctcaacggtg cggtctgtac agtcggctga   1140
```

<210> SEQ ID NO 26
<211> LENGTH: 2667
<212> TYPE: DNA
<213> ORGANISM: Streptomyces DpondAA-B6

<400> SEQUENCE: 26

```
atgaacgcat tgcctccacc ggcgcggcct gccccagtac gttcccgctc gcgttatgga     60
cgacgtgcac tgggaatcag tgcagcggcg ttgctctgtg caggcgcgct cgcggtcccc    120
ggcacagcac tggcggatga tgcagcccct ggtcccgaac agatcaccaa cggagacttc    180
agcgccggta cagcgccatg gtggtggacg ccgaacgcct ccgcggcagt gagcgaaggc    240
cgattgtgtg tagaggtccc cgccggaacc gcagaagcct gggacgtaat cgtgggtcaa    300
aacgatatcc ctatagtcgc aggcgagtcc tacgagctga gttatacagc gcgcagtacg    360
gtaccgctca ccgtgcagac gcgcgtccag gaagcagtag agccatacgg aactgtgctc    420
gccaccgcag atccggtcgg aacggaggat acccaggtga cacgtacctt cacagcatcc    480
gtcgatcaac cggcggccag cgtccagctc caaattgggg ggggagaacg cgcgacgacc    540
ttctgccttg acgacgtcag cctccgtggc ggagcagagc ctcccgtata tgtgccggac    600
acgggatccc cagtccgagt caaccaagtg ggatatctgc cgcgcggtgt caagagcggc    660
acagtcgtaa cagacgcaga ggcaccgctc acctggacag tgaaggccgg ggatggaagc    720
accgcagcaa ctggaaccac agtgccgcgg ggtgaggacc ccagttcccg acagcgggtc    780
cacacattcg atttcggtgg actgaccacg ccgggcgatg gttacacagt agaggtggac    840
```

-continued ggagaggtat cggagccctt ctcgatccga ggtgacctct atgatgggtt gcgctccgat 900
gccctggcct acttctatca caaccggagc ggtatcgaaa tagatgcaga cctggtgggc 960
gaggaatatg cccgtcccgc agggcacatt ggcgtcgcgc cgaacaaggg agacacggac 1020
gtcccgtgta agccaggagt ctgtgactat cggctcgatg tctcaggcgg ttggtacgac 1080
gccggcgacc acggtaagta cgtagtcaac gggggaatca gcgtggcaca gcttatgtcc 1140
acatatgagc gcactctcac cgcggacaac gcagaatcgg cacagctgga cgatggcgcc 1200
ctgagggtcc cggaacgtgg aaatggagtg ccggacatcc tggatgaggc acgatgggaa 1260
atggatttcc tgataaagat gcaggtccct gccggggagc cgttggcagg aatggtgcat 1320
cacaaaatgc acgacgccga gtggaccgga ctgccgatga agccgcactt ggacccgcaa 1380
cagcgtgaac ttcatgcacc ctccaccgca gccaccctca acctggcggc gacggcagca 1440
cagtgcgccc gactctatgc gccctatgac gaggacttcg ccgaccgttg tctccgagca 1500
gcagaaaccg catgggacgc agcgaaaagg cacccggatg tcttcgccga ccccaatgac 1560
ggtgtcggtg gtggtacata cgatgataat gacgtatccg acgagttcta ttgggccgcg 1620
gccgaactct tcaccaccac aggcaaggac acctatcgtc aagaggtgtt gtcgagtgat 1680
cttcacggtg atgcagatgc cgtcttcccc gcaggaggcg gcctcagctg gggtgccaca 1740
gcagggctcg gggcgctcac actggccacg gtaccgaaca acctgaccac ggaccagctc 1800
gatggtgtgc gggcaaccgt caccaccgca gcagatcggt atgcggcgca atcccgcgcc 1860
caggcatatg gcctcccgta cgcaccgcgc ggaacggatt acgtatgggg tagcaactcc 1920
caggtactca ataacatggt ggtcctcgcc gtagcacacg acctgaccgg agaagcggca 1980
tatcaggacg cggtactccg gggtgcagac tacttgttcg ggcgcaatcc gctgaatcag 2040
tcgtatgtca cgggatacgg cgagcgagac tctcacaacc agcaccacag gttctgggca 2100
catcaatatg atagcagttt gcctaatccc gcaccaggtt ccgtagcagg tggcccgaac 2160
ctcacggcag caggaagtgg tgaccccgtc gcggccgaaa agctgtcggg ctgcgccccg 2220
gcaatgtgct acatcgacga catcgggagt tggagcacca acgagattac agtaaattgg 2280
aacgcgccgc tcgcattcat tgcctcgtac cttgacgacg ccggagatgg tggccagacc 2340
acagcgtcac gtacatgcga agtcacgtat agctcgcacc cgtggagcgg gggaagtacc 2400
gtctcggtgc gagtagagaa tacaggttcg gccccagtgg aaccctggtc actgacgtgg 2460
ttgctgccgg gcgagcagaa gctctcccac acctggtcag ccgaattcga gcaacacggg 2520
cgcaccgtgt cagcaaggcc gctggcgtgg aaccggaccc ttgcaccggg agccgcagta 2580
gacttcggct tcaatacgag cgcgacagga gcagcggccg atccaggcac gttcaagttg 2640
aacggtcgcg cctgtgcatc gggctga 2667

<210> SEQ ID NO 27
<211> LENGTH: 2133
<212> TYPE: DNA
<213> ORGANISM: Streptomyces LaPpAH-95

<400> SEQUENCE: 27
atgtcaaccc gtggaaccat aaaacagggt ctgcgccgta gactcgcagc agcaagtgca 60
ctggcaatgg gagcggcact cgcagtagca atcccgacaa ccgcagacgc cgcagccgcc 120
cgagtcgata atccatatgt cggtgcaaag gcatacgtga acccagactg gagtgcaaaa 180
gcagcggccg aaccgggcgg agcagcgatt gccgatacac cggcgttcgt gtggatggac 240

-continued cgcatcgcag caatcggtgg tacaccgggt gccatgtcgc tcagggaaca cctggacacg 300
gcactggatc agggtgcaaa tctcttccaa gtcgtcatct acgacctccc gggtcgtgac 360
tgcgcagccc ttgcaagtaa tggggagctg ggaccgacgg agctcgatag gtataagtcc 420
gaatacatcg acccgatcag tgagatcctc gcggacccgg catacgcgaa tctgcggata 480
gtcacaatca tcgagcccga ctcgctgccg aatattgtga cgaatgcggg tggcaccgca 540
ggatcgacag acgcgtgtgc aacaatgaag gccaacggta attatgagaa aggcgtcggt 600
tatgcactcc acaccctcgg tgccatcccg aatgtatata actacgtgga cgcagcccac 660
cacggctggt tggggtggga tagcaacatg gtgccggccg gggtggagtt caagaaggca 720
gcaacaagtg agggagcaac cgtggacgat gtcgcaggat tcatagtaaa tacggcgaac 780
tactccgcac ttaaggagcc caatttcaaa ataaccgact cagtgaacgg cactacggtg 840
cgtcagagta agtgggtcga ttggaactac tatactgacg agctcagttt cgcgcaggcc 900
ctgcgcaccc agctggtagg ccagggattc aactctaaca tcggtatgct cattgacacg 960
gcacgcaatg gatggggagg ctcggatcgt ccgacatcag cagggccgct gacgtcggtc 1020
gacgactacg tcaacggtgg ccgggtcgat cgccggatcc atgcgggaaa ctggtgcaat 1080
cagtctggcg caggaatcgg cgagaggccg acctcagcgc ccgaagcggg aatcgacgcg 1140
tatgtatggg caaagccccc cggcgagtcg gacgggagta gtcaggcaga agataacgac 1200
gagggaaaag gtttcgatcg aatgtgtgac ccgacatatg aaggcaacgg aaggaacgga 1260
aacagcaaga cgggcgcgtt gccgaattcc ccagtagcag ggcactggtt cagtgcacag 1320
ttccaagagc ttgtccgtaa tgcatatccc ccgatcgacg gtagcggaga gaacccgggt 1380
ggcggcggag acgacgatac ccaggcgccg acggcaccga cagggctcac atcctcggcg 1440
aagaccagtt caagcgtcag tctctcatgg accgcctcct cggacaataa agcagtgacc 1500
ggttacgatg tctaccgggg aggaacgaag gtaggcagca cgaccacgac atcgtacacg 1560
gacacgggac tgagcgcctc gacggcatat tcatacaccg tgaaggcgaa agatgccgcc 1620
gggaacgtgt cggcagcatc gtcagcactg agcgtcacaa cgtcagccgg gggaggcaca 1680
ggaacgggaa gcctgaaggt ccaatataaa aataacgaca acagtccgac agacaaccag 1740
atcaggttcg gtctgcaact cgtgaatacg ggatcctcgg ccgtggacct gagtaccgtc 1800
aagctccgct actggttcac cccagaatcc ggcagctcca cgttcgggac agcctgcgat 1860
tatgcagtac tgggatgtgg taagctgtcc cttgccgtac aatcaggcgg aagtgcggca 1920
ggagcaagtc actacctcga ggtcagcttc gggtcgggga gccttgcggc aggtgcatcc 1980
acgggggaaa tgcagctgcg actgaacaag agcgattggt cgaacttcaa tgaggcggac 2040
gactatagtc atgggaccgg aacctcgttc gccgacgcat ccaaaatagg agtgtatacc 2100
gccggcgcgt tgtcctgggg tacagcccct tga 2133

<210> SEQ ID NO 28
<211> LENGTH: 1104
<212> TYPE: DNA
<213> ORGANISM: Streptomyces LaPpAH-95

<400> SEQUENCE: 28
atggcgcgca ggcgcacaca gctggcaagc cttgcggccg tcctggccac cctcctcggt 60
ggcatcgcct tcactctgct gggacagggt tcggcacaag cccacggcgt gaccatgtcc 120
ccgggatccc gtacatacct ctgctggttg gacgcaaaga catcgaccgg ttcactggat 180
ccgaccaatc cggcatgtaa ggcagcactt gccgagtccg gcgcgtcctc gctgtataac 240

-continued

```
tggttcgccg tgctcgacag taacgcaggt ggacgaggcg caggatacgt acccgacggc    300

accctttgta gcgctggaga caggtcgccg tacaatttca caggctataa cgcagcccgg    360

ggggattggc ccaggactca tctgaccagc ggcgcgaaaa tcgaggtaga ccactcaaat    420

tgggcagcgc acccgggaga gttccgtgtg tatatgagca agccgggata ctcgccgacc    480

acggaactcg gttgggatga cctcgacctc atccagaccg tctctaatcc gccccaagtg    540

gggtccccgg gaacggacgg tggccattat tattgggatc tgactttgcc ctcgggcagg    600

tcaggagatg ccgttatgtt catccaatgg gtaaggagcg acagtcagga gaacttcttc    660

agctgcagtg acatcgtctt cgatggcggc aatggtgaag taaccggaat ccgcggaagt    720

ggctcgaccc cagacccgga cccaaccgac ccgaccccgg acccgacaga ccctaccgat    780

ccgacagacc cccacacagg atgcatggca gtgtacaatg tgacgaatag ctggtcaggt    840

ggattccagg gtagcgttga agtaatgaac cataatacca cggcgctcga cggttgggcg    900

gtgcagtgga aaccgggtac cggtacgaca gtctccagcg tatggtcggg cgtattgtcg    960

acgggaagtg atggtaccct cacggtgaag aacgcagact ataatcgcag catcccaccg   1020

gacggctcgg tcaccttcgg tttcacggcg acctcgacgg ggaacgattt cccggtgggg   1080

tccataggtt gtgtctcccc gtga                                          1104
```

<210> SEQ ID NO 29
<211> LENGTH: 2763
<212> TYPE: DNA
<213> ORGANISM: Streptomyces LaPpAH-95

<400> SEQUENCE: 29

```
atgctggcag tcggcctcgc acagggtacc gcaatcgcga ggccagcaag tgcccaggca     60

ggcacgggtg cacgtgcggc cgcagcggga gacgatccct acacccaggc cttcctgacg    120

cagtacggta agctgaagga cgctgcaaac ggctattttt caccggatgg cttgccgtac    180

cattcggtag aaaccttgat ggtggaggca cctgatcatg gccaccagac gacctctgaa    240

gccgtctcct tctggatgtg gttggaggcc gcatacggtc gagtaacggg cgactgggcc    300

ccgttcaatg cagcgtgggc agtcgcagaa aagaccatta tcccccagca tgcggaccag    360

tcgacatccg actcgtataa cccgtccgca ccggccacgt atgcaccgga gcaccctctg    420

ccgagcggct acccgtcggc attggatggt accgtcccgg tcggtacaga ccctctcagc    480

gcagaattgg cgagttcgta tggaaccatg gacgtgtatg gtatgcattg gctcatggat    540

ctggacaacg tgtatggtta cggtaacaag ccgggtacgg gtggagagag cggtcccggc    600

gcaggagcgt cgttcataaa tacctatcaa cgtggtgcac aggagagcgt gtgggagacg    660

gtaccgcaac cgacgacgga tctcttcaag tacggagggc cgaacggata cctggacttg    720

ttcgtgggtg actccagcta cgcgaaacaa tggaagtaca ccaacgcacc ggacgccgat    780

gcacgcgccg tccaggcggc atactgggca tatcggtggg caagtgagca aggcaaggaa    840

tcgcaggtgg cagcatcggt ggcgaaagcc gcaaaaatgg gtgactacct ccgctatgcc    900

atgttcgaca agtatttcaa gcgagtcgga gattgtacgg acccaaatag ctgccccgca    960

gcgtcgggtc gcgacagcca gcactacctg ttgtcgtggt actatgcctg ggtggcgca   1020

gcggcaggta gtggaggcgg atgggcctgg cgtatcggtg acggggcatc gcaccaggga   1080

tatcagaacc cgcttgcagc atgggccctg agcaacgtcc cgtcgctgac cccgaagagt   1140

gcaacggccc gatcggattg gtccaagtcg ctgacccgcc aactcgagtt cttgacatgg   1200
```

-continued

```
ctgcagtcaa gcgagggcgc cctggcaggg ggttgcacca actcatggga aggcagctac   1260
tcaacacccc cggccggaac gcccactttc tatggtatgg catacgactg gcagccggtg   1320
tatcatgacc cggcgtcgaa taattggttc ggcttccaag cctggggtat ggaaagggtg   1380
gcggcatact actatgtaac ggggaacgca acagcagagg cagtgctttc gaagtgggtc   1440
gcctgggcat catcggaaac cactattgga tcggacggta gcttccgttt cccttcgacg   1500
ctgaattgga ccggggaacc agacacctgg aacgcagcat ccccgggtga taacgccgga   1560
ctgcatgtgt cagtcgtaga ctatgcaaat gacgtcggag tcggtgcggc gtatgtgaag   1620
acactcacct actacgcagc gaagagcgga gacgaagatg cagccgcatt ggcaaaggcc   1680
ctgctcgacg caatggcact caacacaacc gacaagggaa tcagtgtccc ggaaacgcgc   1740
ctcgactaca atcgtttcga tgacgaggtc tacatcccgt cgggctggtc tggtacaatg   1800
ccgaacggtg accccgtccg tccgggaagt actttcattt ccatacggag ctggtataaa   1860
gatgacccag actggcctaa agtacaggca tacctcgacg gcggggatgc gccggtattc   1920
acctaccacc ggttctgggc ccaagccgcc ctggcattgg cattcgcaat ttatgcggaa   1980
cttctggtag agggaggagg tggggaacct ggtggtgaca cggagccgcc gaccgcaccg   2040
ggcggactca ccgtaacagc tacaacgaag gatagcgtct ccctcagctg gtcggcatca   2100
accgacaaca cagcagtgac cgggtatgac gtgtaccgta atggagtact ggccggaaac   2160
gcaacaggcc gcacattcac ggatagcggc ctcgcagcca atacggaata tacatatgcg   2220
gtcgcagcca gggacgcagg tgggaataca tctgcgctga gcgatgccgt cctggcaaag   2280
acaaaaacag gtgggagcac gggtaccggc gcagtaaagg tccagtataa gtcgaccgat   2340
agctcggcaa ctgacaacca aatccgtatg ggactgcaag tagtcaacac cggctcggca   2400
ccggtagatc tgtcgacagt gaaggtgcgc tattggttca cagccgacgg tggaccctcc   2460
accttcggaa catactgcga ctatgccgca ttggggagct cgacgattac ccacactgtc   2520
gtcgccgtaa gctcgccgaa gacaggagca gaccgatacc tggaggtcgg gtttaccggt   2580
ggtgcgggca cactcgcagc aggtgcgtcc acgggggaga tccaattgcg actgaacaag   2640
tcggattggt caaatttcaa cgaggccgat gactacagcc gtgcaaccaa tacagcctat   2700
gcagattcgt ctaaggtagg ggcctacgtc gcaggagcac tcgcatgggg agtcgaaccc   2760
taa                                                                 2763
```

<210> SEQ ID NO 30
<211> LENGTH: 1803
<212> TYPE: DNA
<213> ORGANISM: Streptomyces LaPpAH-95

<400> SEQUENCE: 30

```
atgctgcacc cccttcgcac attccgtcgg gcagcacgaa ccgtcgcggt agccaccgca     60
gcgctcctcc ttccgctcgc cggagcacat ccggccagtg cagacgccgc acgtgcggca    120
gccgcaggtt cgggatattg gcacacgtca ggtcgccaga tcctggatgc agcaaaccag    180
cccgtgcgca tcgcaggaat caattggttc ggattcgaaa ccgcaaacta tgtcccgcat    240
ggcctctgga gccgtgacta taagtcgatg atcgaccaaa tgaggtccct gggttataac    300
acgatccgtc tgccgtactc agatgacata ttcgcaggaa ccgagccggc aagcatcaat    360
tattcggcgg gtatgaatac ggatctcgca ggtctgaact cgctccaggt gatggaccgt    420
atcgtcgacc acgccggcag tttcggaatg aaagtaatct tggataggca ccgtcccgac    480
tccgcaggtc agtcggcact gtggtatacc tccgcggtac cggagagcac gtggctggca    540
```

```
catctcaagt cacttgcggc ccgctacgcg ggcaatgacg ccgtggtagg tatcgacctc    600
cacaacgagc cgcacgaccc ggcatgttgg ggctgtggag ataccacgaa ggactggcgt    660
ctcgccgcgc agcgcggtgg aaacgccgca ttgagcgcca atccggacct tctgatattc    720
gtcgaggggg tgcagacggt agatggagtc tcgggctggt ggggtggtaa cctgatggga    780
gtgggacagt atcccgtgga actgtctgtg ccgcacaagg tggtgtacag cgcacacgat    840
tacgcaacca gtgtggcaca acagccttgg ttcacggaca gttccttccc ggacaatatg    900
cccggtgtct gggataagta ttggggctac atcttcaaac agaacattgc ccccgtatgg    960
gtaggtgaat tcggaaccac actgcagagt accaccgacc agaaatggct caaggccctg   1020
gcggactatc tgcgaccgac aagccagtac ggagcagact cgttcagctg gacgttctgg   1080
tcttggaatc ccaactcggg tgatacagga ggtatcctca aggacgattg gacgagtgtc   1140
gacacagtca aggacggata cctggcgagt atcaaggcgc cggacttcgg taatggtggt   1200
ggaagtggtg gcgatgacga cacacaggcc ccgacggcac caacaggact cgccgtaaca   1260
gggacaaccg gtaccagtgt ctcgctgagt tggaaggcag catcggacga cacgggggtg   1320
acagcgtatg acgtctaccg cggtagcacg aaggcaggaa ccgcgacagg tacgacgttc   1380
acagacacgg gtgtaacctc gggtacgagt tatacctata cagtccgcgc acgagacgcg   1440
gcaggaaaca cgtccgcccc ctcggcatcg gtaaccgcaa ccacgacagg gtccggagga   1500
aataccggtt gtaaagccgt gtacacggtc aacggagact gggggtcggg attcggggta   1560
gacatcaccg tgacgaacac aggcaccgcc ccggcaacga gctggaagtt gacatggacc   1620
tacggtggct cgcagaaaat aacgaatatg tggaacgcaa gctataccca gtcaggcgcc   1680
tccgtgaccg taacatctac agactacaat ggaggactcg cggcaggggc acacaccggc   1740
ttcggtttcc agggaacacc cgcggcgggc gcagtcccaa ccgtgtcctg tacgctgagt   1800
taa                                                                 1803
```

<210> SEQ ID NO 31
<211> LENGTH: 2373
<212> TYPE: DNA
<213> ORGANISM: Streptomyces LaPpAH-95

<400> SEQUENCE: 31

```
atgcgaagtt tccccctgcc cgcgctgagg agacggagtc ggcggcccgg acgtcccctc     60
ggagcagtcg ccttggccct ggcagtcggc gccggtctgc tgctcccgtt gtcgctgccg    120
gccggagcag cagcggcacc ggccttcgac tatggagaag ccttgcagaa gtcggtactg    180
ttctacgagg cccagcaatc aggaaagttg ccggatacga acagggtgag ctggcgcggc    240
gacagcgcac tcgacgatgg taaagacgcc ggactggacc tcaccggagg ttggtatgac    300
gccggcgacc acgtaaagtt cgggctgcca atggcatact cagcaacgat gctggcatgg    360
ggtggcaccg aacaacgcgc cgcgtacgaa gcaagcggac agctgcccca tctgcgcaat    420
aacttgcgtt tcgtagacga ctatctgctg aaggcgcacc cgtcaccgaa tgtcttgtac    480
ggacaagtcg gaaatggagg tgacgatcat aagtggtggg gaccggcaga agtaatgccg    540
atgaagcggc cggcgtataa aatagacgca tcctgcccgg gtagcgacct ggcgggtcag    600
accgccgcag cgctcgcaag ttcgtccatg gtgttctcgg acagtgaccc cgcctacgcc    660
gcaaaattga ttacacacgc aaagcaactg tacaccttcg cggacacgta tcgcggcaag    720
tactcggact gtatcacgga cgcacagtcg tactacaact cctggagcgg ctataatgat    780
```

```
gagttggtat ggggcgcgat ctggctttac aaagcaaccg gagacaccgc ctacctggca    840

aaggccgagt cctattacga caacctctcg accgaaccgc agacaacgac gcgatcatat    900

cgctggacct tgtcgtggga tgacacctcc tacggcgcgt atgtccttct cgcacaactc    960

acgggaaaac agaagtacat tgacgacgca aatcggtggt tggactggtg gaccgtggga   1020

gtcaacggac agcgcgtgcc ctatagcccg ggtggtcagg cagtactgga tagctggggt   1080

agtctgcggt acgccgccaa caccgcgttc gtagcactca gctactccga ctggctgaca   1140

ggtgacgcaa cgcgtaaggc ccggtaccac gatttcgccg tgcgccagat cgactatgca   1200

ctcggagata atccgcgagg atcgtcctat gtcgtcggtt tcggcgagaa cccacccacc   1260

aaaccgcacc atcgtacggc gcacggttcg tggaccgacc aaatgaccaa tccggtggag   1320

acgcgccaca cgctgtacgg agcactggta ggcggaccct cagccccaga cgatacctat   1380

acagacgacc gagggaacta cgtcaataac gaggtggcaa ccgactacaa cgcggccttc   1440

actggagcgt tggcacgact gtatgcggag tacggaggtt cgcccctcac cgacttccct   1500

cagccggaag agcccgacgg accggaaatg agcgtccagg catctgtaaa tgcagcggga   1560

gccaacttca cagaggtgaa ggcgtatctt attaaccgaa gtgcctggcc agcacgcgca   1620

ctcacagatg caagcgtccg atattacttc accctggaac cgggagtcgc cccgggagac   1680

attagtttca cgacaaacta taatcaatgc ggcgaggtca ccggccctac gcacctgaca   1740

ggagatgtct actatgcaac cgtcgactgt tcagacacag acatcgcccc ggccggccag   1800

agcgcatacc gtaaagaagt gcagttccgc atctccagcg caggtgcatg ggatccttcc   1860

aacgactggt cgtatccgag cacggcaact acccccggag gtacgccggt cgacgccccc   1920

catatggtac tccttgaggg ttcggcgccg cagtggggga cggcccctga tggaaccgac   1980

ccgggaccag gtccggaccc taccacaacg ccggaaccat ccccgacgcc agacccaacc   2040

gatacacccg acccggaacc tggagcatgc gatgtcacct accgagtgtc gcaggcatgg   2100

ggtacagggt tcaccgcgga cgtcacagtc aagaatacgg gaccgacccc cctcgacgga   2160

tggcagcttg cattcgactt ccagggagcc gagagtgtat cgaacgcgtg gaacgccacc   2220

gcgacgcaga gtggaactag ggtgaccctc aagaacgcag gtcacaacgg ctcggtgccg   2280

gcaggtggtt ccgcctcgtt cggcttccag gcgaacgggg cccccggagc agacccgcat   2340

agtttcacat tgaacggaaa ggaatgtggt tga                                2373
```

<210> SEQ ID NO 32
<211> LENGTH: 1287
<212> TYPE: DNA
<213> ORGANISM: Streptomyces LaPpAH-95

<400> SEQUENCE: 32

```
atgacaggcc ggccgctgcc ggcattggca ggagcggcag ccgcactggt cctggcggcg     60

gcaagcatgc tgaccggagc gagctccgca agcgcgtcgc cggtgaccga ttgtacaccg    120

tggggtacaa cggagctcct cggtggggag tacttgtatc agcagaacga gtggaactcg    180

gacagcgaac aatgtgtcgg agtggacccg gacaccggag cctggagcgt aacaacaagc    240

agcttcaatc ttcccacaaa cggcgcacca gccacgtacc cgagcagcta taagggatgc    300

cactgggggg catgtacctc ggattctgga ctgccgctcc gcgtggacga gttgggatca    360

gtacatacag actggtcgac cacacaggta ggctccggtg cctataatgt gagtatggac    420

gtctggttta acagtgcacc tgtaacggat gaccagccgg acggcacgga actgatgatc    480

tggatgaacc accgcggtgg agtgcagccc attggaagcc gtacggccac agtccagctc    540
```

-continued

```
gatggtcgca cgtgggacgt atggaccgga cccggcgcat cgggatggaa ggtcatcagt    600

tacgtcttgc agggcggagc gaccgagctc acagggttcg atgtgaagtc gttgatcgac    660

gacggagtgg gtcgtggcca aatagacccg gcccattatc tcatcgacgc agaggccgga    720

ttcgagatct ggcagggtgg ccaggggctg ggtatgaaag agttcagctt cgaggccagc    780

gcaggaaccg acggtggcga tgacggaggc gacggcgatc cgggcggcgg aggcaccaca    840

ggagcactca aggcccagta caaaaataac gattccagcg cgacggacaa tcagatacgc    900

ccaggcctgc agctcgtgaa taccggatcc acagctgtcg acctgtctac tgtgaagctg    960

cggtactggt tcacccccga aagtggcgcg gcgggtttcg gcacggcctg tgattatgca   1020

gtcgtcggtt gtggaaacgt cacgcacacg gtaaagcaag cagggacggc agccggcgca   1080

tcacactact tggaggtggg tttcacgggc ggatcgctgg ccccgggtgc atcgaccggt   1140

gaaattcagc tgcgattcaa caagtcggat tggtcggcgt tcgacgaagc cgacgactac   1200

agtcgtgcag cgaacacggc gttcaccgac gcatcgaagg tgggtgtcta cgtgaatgga   1260

gcattgtcaa gcggtacagc gccgtga                                       1287


<210> SEQ ID NO 33
<211> LENGTH: 41
<212> TYPE: DNA
<213> ORGANISM: Artificial Sequence
<220> FEATURE:
<223> OTHER INFORMATION: synthetic

<400> SEQUENCE: 33

tgtgcgggct ctaacacgtc ctagtatggt aggatgagca a                         41


<210> SEQ ID NO 34
<211> LENGTH: 26
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (13)..(13)
<223> OTHER INFORMATION: n is a, c, g, or t

<400> SEQUENCE: 34

tctagtcgag cancggaggt acggac                                          26


<210> SEQ ID NO 35
<211> LENGTH: 39
<212> TYPE: DNA
<213> ORGANISM: Artificial Sequence
<220> FEATURE:
<223> OTHER INFORMATION: synthetic

<400> SEQUENCE: 35

aaaaaaaaac cccgccccug acagggcggg guuuuuuuu                            39
```